US007582807B2

(12) United States Patent
Hannoufa et al.

(10) Patent No.: US 7,582,807 B2
(45) Date of Patent: Sep. 1, 2009

(54) REGULATION OF GENE EXPRESSION USING CHROMATIN REMODELLING FACTORS

(75) Inventors: Abdelali Hannoufa, Saskatoon (CA); Derek J. Lydiate, Saskatoon (CA); Ming-Jun Gao, Saskatoon (CA)

(73) Assignee: Her Majesty the Queen in right of Canada, as represented by the Minister of Agriculture and Agri-Food, Saskatoon (CA)

( * ) Notice: Subject to any disclaimer, the term of this patent is extended or adjusted under 35 U.S.C. 154(b) by 142 days.

(21) Appl. No.: 10/516,753

(22) PCT Filed: Jun. 6, 2003

(86) PCT No.: PCT/CA03/00822

§ 371 (c)(1),
(2), (4) Date: Aug. 18, 2005

(87) PCT Pub. No.: WO03/104462

PCT Pub. Date: Dec. 18, 2003

(65) Prior Publication Data

US 2006/0123506 A1    Jun. 8, 2006

Related U.S. Application Data

(60) Provisional application No. 60/387,088, filed on Jun. 6, 2002.

(51) Int. Cl.
*C12N 15/82* (2006.01)
*C12N 15/63* (2006.01)
*C12N 15/10* (2006.01)
*A01H 5/00* (2006.01)

(52) U.S. Cl. ............ 800/278; 800/298; 435/320.1; 435/468; 536/23.1; 536/23.6; 536/24.1

(58) Field of Classification Search ............ None
See application file for complete search history.

(56) References Cited

U.S. PATENT DOCUMENTS

| 5,428,147 | A | 6/1995 | Barker et al. | |
|---|---|---|---|---|
| 2003/0143712 | A1* | 7/2003 | Verdin et al. | ............ 435/196 |
| 2006/0123506 | A1 | 6/2006 | Hannoufa et al. | |

FOREIGN PATENT DOCUMENTS

| CA | 2407460 | * | 4/2001 |
|---|---|---|---|
| CA | 2 407 460 | | 11/2001 |
| EP | 1 094 112 | | 4/2001 |
| WO | 97/35990 | | 10/1997 |
| WO | 98/37184 | | 8/1998 |
| WO | 00/37660 | | 6/2000 |

OTHER PUBLICATIONS

Ma et al 1995 Plant Physiology 109:341-346 provided in Applicant IDS.*

Jenster et al 1997 PNAS 94:7879-7884, provided in Applicant IDS.*
Ahmad et al., "WD Repeats of the p48 Subunit of Chicken Chromatin Assembly Factor-1 Required for in Vitro Interaction with Chicken Histone Deacetylase-2", Journal of Biological Chemistry (1999); vol. 274, No. 23: 16646-16653.
Altschul et al.,"Gapped Blast and Psi-Blast: a new generation of protein database search programs", Nucleic Acids Research (1997); vol. 25, No. 17: 3389-3402.
An et al., "Strong, constitutive expression of the *Arabidopsis ACT2/ACT8* actin subclass in vegetative tissues", The Plant Journal (1996); vol. 10, No. 1: 107-121.
Archdeacon et al., "A single amino acid substitution beyond the C2H2-zinc finger in Ros derepresses virulence and T-DNA genes in *Agrobacterium tumefaciens*", FEMS Microbiology Letters (2000); 187: 175-178.
Bannister et al., "The CBP co-activator is a histone acetyltransferase", Nature (1996); vol. 384: 641-643.
Beetham et al., "A tool for functional plant genomics: Chimeric RNA/DNA oligonucleotides cause in vivo gene-specific mutations", Proceedings of the National Academy of Sciences of USA (1999); vol. 96: 8774-8778.
Berleth et al., "Plant morphogenesis: long-distance coordination and local patterning", Current Opinion in Plant Biology (2001); vol. 4: 57-62.
Bittinger et al., "*rosR*, a Determinant of Nodulation Competitiveness in *Rhizobium etli*", Molecular Plant-Microbe Interations (1997); vol. 10, No. 2: 180-186.
Boyle et al., "Repression of the Defense Gene *PR-10a* by the Single-Stranded DNA Binding Protein SEBF", The Plant Cell (2001); vol. 13: 2525-2537.
Brandstatter et al., "Two Genes with Similarity to Bacterial Response Regulators Are Rapidly and Specifically Induced by Cytokinin in *Arabidopsis*", The Plant Cell (1998); vol. 10: 1009-1019.
Brightwell et al., "Pleiotropic Effects of Regulatory *ros* Mutants of *Agrobacterium radiobacter* and Their Interaction with Fe and Glucose", Molecular Plant-Microbe Interactions (1995); vol. 8, No. 5: 747-754.

(Continued)

*Primary Examiner*—Phuong T Bui
*Assistant Examiner*—Brent Page
(74) *Attorney, Agent, or Firm*—Merchant & Gould P.C.

(57) ABSTRACT

The invention provides a method to regulate expression of a gene of interest in a plant comprising, introducing into the plant a first nucleotide sequence comprising, the gene of interest operatively linked to a first regulatory region, and an operator sequence capable of binding a fusion protein, and a second nucleotide sequence comprising a second regulatory region in operative association with a nucleotide sequence encoding the fusion protein. The fusion protein comprising, a DNA binding protein, or a portion thereof, capable of binding the operator sequence, and a recruitment factor protein, or a portion thereof, capable of binding a chromatin remodelling protein. In this manner, expression of the second nucleotide sequence produces the fusion protein that regulates expression of the gene of interest.

13 Claims, 36 Drawing Sheets

OTHER PUBLICATIONS

Burge et al., "Prediction of Complete Gene Structures in Human Genomic DNA", Journal of Molecular Biology (1997); vol. 268: 78-94.

Caddick et al., "An ethanol inducible gene switch for plants used to manipulate carbon metabolism", Nature Biotechnology (1998); vol. 16: 177-180.

Carrington et al., "Bipartite Signal Sequence Mediates Nuclear Translocation of the Plant Potyviral Nla Protein", The Plant Cell (1991); vol. 3: 953-962.

Chou et al., "*Agrobacterium* transcriptional regulator Ros is a prokaryotic zinc finger protein that regulates the plant oncogene *ipt*" Proceedings of the National Academy of Sciences of USA (1998); vol. 95: 5293-5298.

Chrivia et al., "Phosphorylated CREB binds specifically to the nuclear protein CBP", Nature (1993); vol. 365: 855-859.

Clough et al., "Floral dip: a simplified method for *Agrobacterium*-mediated transformation of *Arabidopsis thaliana*" The Plant Journal (1998); vol. 16, No. 6: 735-743.

Cooley et al., "The *virC* and *virD* Operons of the *Agrobacterium* Ti Plasmid Are Regulated by the *ros* Chromosomal Gene: Analysis of the Cloned *ros* Gene" Journal of Bacteriology (1991); vol. 173, No. 8: 2608- 2616.

D'Souza-Ault et al., "Analysis of the Ros Repressor of *Agrobacterium virC* and *virD* Operons: Molecular Intercommunication between Plasmid and Chromosomal Genes" Journal of Bateriology (1993); vol. 175, No. 11: 3486-3490.

Eisner et al., "Analysis of *Arabidopsis thaliana* transgenic plants transformed with *CER2* and *CER3* genes in sense and antisense orientations" Theoretical and Applied Genetics (1998); vol. 97: 801-809.

Emiliani et al., "Characterization of a human *RPD3* ortholog, HDAC3", Proceedings of the National Academy of Sciences of USA (1998); vol. 95: 2795-2800.

Fischle et al., "A New Family of Human Histone Deacetylases Related to *Saccharomyces cerevisiae* HDA1p" The Journal of Biological Chemistry (1999); vol. 274, No. 17: 11713-11720.

Fukaki et al., "Genetic evidence that the endodermis is essential for shoot gravitropism in *Arabidopsis thaliana*" The Plant Journal (1998); vol. 14, no. 4: 425-430.

Gao et al., "Regulation and characterization of four *CBF* transcription factors from *Brassica napus*", Plant Molecular Biology (2002); vol. 49, 459-471.

Gao et al., "Expression of the extrinsic 23-kDa protein of photosystem II in response to salt stress is associated with the K+/Na+ discrimination locus *Kna1* in wheat", Plant Cell Reports (2001); vol. 20: 774-778.

Gao et al., "A novel protein from *Brassica napus* has a putative Kid domain and responds to low temperature", The Plant Journal (2003); vol. 33: 1073-1086.

Gatz, Christiane, "Chemical Control of Gene Expression", Annual Review Plant Physiology and Plant Molecular Biology (1997); vol. 48: 89-108.

Gatz et al., "Promoters that respond to chemical inducers", Trends in Plant Science (1998); vol. 3, No. 9: 352-358.

Gelmetti et al., "Aberrant Recruitment of the Nuclear Receptor Corepressor-Histone Deacetylase Complex by the Acute Myeloid Leukemia Fusion Partner ETO" Molecular and Cellular Biology (1998); vol. 18, No. 12: 7185-7191.

Gonzalez et al., "Characterization of Motifs Which Are Critical for Activity of the Cyclic AMP-Responsive Transcription Factor CREB", Molecular and Cellular Biology (1991); vol. 11, No. 3: 1306-1312.

Gonzalez et al., "Cyclic AMP Stimulates Somatostatin Gene Transcription by Phosphorylation of CREB at Serine 133" Cell (1989); vol. 59: 675-680.

Grustein, Michael, "Histone acetylation in chromatin structure and transcription", Nature (1997): vol. 389: 349-352.

Hart et al., "A 61 bp enhancer element of the tobacco β-1,3-glucanase B gene interacts with one or more regulated nuclear proteins", Plant Molecular Biology (1993); vol. 21: 121-131.

Hassig et al., "Histone Deacetylase Activity Is Required for Full Transcriptional Repression by mSin3A", Cell (1997); vol. 89: 341-347.

Hassig et al., "Nuclear histone acetylases and deacetylases and transcriptional regulation: Hats off to HDAC's", Current Opinion in Chemical Biology (1997); vol. 1: 300-308.

Hassig et al., "A role for histone deacetylase activity in HDAC1-mediated transcriptional repression", Proceedings of the National Academy of Sciences of USA (1998); vol. 95: 3519-3524.

Helarlutta et al., "The *Short-Root* Gene Controls Radial Patterning of the *Arabidopsis* Root through Radial Signaling", Cell (2000); vol. 101: 555-567.

Holtorf et al., "Comparison of different constitutive and inducible promoters for the overexpression of transgenes in *Arabidopsis thaliana*", Plant Molecular Biology (1995); vol. 29, 637-646.

Hurley et al., "Regulation of Changes in Cytosolic $Ca^{2+}$ and $Na^+$ Concentrations in Rat Submandibular Gland Acini Exposed to Carbachol and ATP", Journal of Cellular Physiology (1996); vol. 168: 229-238.

Jofuku et al., "Control of *Arabidopsis* Flower and Seed Development by the Homeotic Gene *APETALA2*", The Plant Cell (1994); vol. 6: 1211-1225.

Johnson et al., "Histone deacetylases: complex transducers of nuclear signals", Cell & Development Biology (1999); vol. 10: 179-188.

Johnson et al., "Activation domains of transcriptional regulatory proteins", Journal of Nutritional Biochemistry (1993); vol. 4: 386-398.

Kadosh et al., "Repression by Une6 Involves Recruitment of a Complex Containing Sin3 Corepressor and Rpd3 Histone Deacetylase to Target Promoters", Cell (1997); vol. 89: 365-371.

Kakimoto, Tatsuo, "CKI1, a Histidine Kinase Homolog Implicated in Cytokinin Signal Transduction", Science (1996); vol. 274: 982-985.

Kapila et al., "An *Agrobacterium*-mediated transient gene expression system for intact leaves", Plant Science (1997); vol. 122: 101-108.

Kaya et al., "*FASCIATA* Genes for Chromatin Assembly Factor-1 in *Arabidopsis* Maintain the Cellular Organization of Apical Meristems", Cell (2001); vol. 104: 131-142.

Keller et al., "Molecular Analysis of the *Rhizobium meliloti mucR* Gene Regulating the Biosynthesis of the Exopolysaccharides Succinoglycan and Galactoglucan", Molecular Plant-Microbe Interactions (1995); vol. 8, No. 2: 267-277.

Khochbin et al., "The origin and utility of histone deacetylases", FEBS Letters (1997); vol. 419: 157-160.

Knight et al., "Cold Calcium Signaling in *Arabidopsis* Involves Two Cellular Pools and a Change in Calcium Signature after Acclimation", The Plant Cell (1996); vol. 8: 489-503.

Kohno-Murase et al., "Effects of an antisense napin gene on seed storage compounds in transgenic *Brassica napus* seeds", Plant Molecular Biology (1994); vol. 26: 1115-1124.

Kölle et al., "Substrate and sequential site specificity of cytoplasmic histone acetyltransferases of maize and rat liver", FEBS Letters (1998); vol. 421: 109-114.

Kuo et al., "Roles of histone acetyltransferases and deacetylases in gene regulation", BioEssays (1998); vol. 20: 615-626.

Laurenzio et al., "The Scarecrow Gene Regulates an Asymmetric Cell Division That is Essential for Generating the Radial Organization of the Arabidopsis Root", Cell (1996); vol. 86: 423-433.

Liscum et al., "Phototropism: A "Simple" Physiological Response Modulated by Multiple Interacting Photosensory-response Pathways", Photochemistry and Photobiology (2000); vol. 72, No. 3:273-282.

Lotan et al., "*Arabidopsis* Leafy Cotyledon1 Is Sufficient to Induce Embryo Development in Vegetative Cells", Cell (1998); vol. 93: 1195-1205.

Lusser et al., "Histone acetylation: lessons from the plant kingdom", Trends in Plant Science (2001); vol. 6, No. 2: 59-65.

Mandel et al., "Definition of constitutive gene expression in plants: the translation initiation factor 4A gene as a model", Plant Molecular Biology (1995); vol. 29: 995-1004.

Meyer et al., "The Promoter of the Gene Encoding 3',5'-Cyclic Adenosine Monophosphate (cAMP) Response Element Binding Protein Contains cAMP Response Elements: Evidence for Positive Autoregulation of Gene Transcription", Endocrinology (1993); vol. 132, No. 2: 770-780.

Miki et al., "Fundamentals of gene transfer in plants", In Plant Metabolism, 2nd edition (1997); DT Dennis, DH Turpin, DD Lefebrve, DB Layzell (eds), Addison Wesly, Langmans Ltd., London: 561-579.

Monroy et al., "Low-Temperature Signal Transduction: Induction of Cold Acclimation-Specific Genes of Alfalfa by Calcium at 25°C", The Plant Cell (1995); vol. 7: 321-331.

Montminy, Marc, "Transcriptional Regulation by Cyclic AMP", Annual Review of Biochemistry (1997); vol. 66: 807-822.

Murashige et al., "A Revised Medium for Rapid Growth and Bio Assays with Tobacco Tissue Cultures", Physiologia Plantarum (1962); vol. 15: 473-497.

Murfett et al., "Identification of *Arabidopsis* Histone Deacetylase HDA6 Mutants That Affect Transgene Expression", The Plant Cell (2001); vol. 13: 1047-1061.

Murray et al., "Codon usage in plant genes", Nucleic Acids Research (1989); vol. 17, No. 2: 477-498.

Nakai et al., "A Knowledge Base for Predicting Protein Localization Sites in Eukaryotic Cells", Genomics (1992); vol. 14: 897-911.

Nakajima et al., "Intercellular movement of the putative transcription factor SHR in root patterning", Nature (2001); vol. 413: 307-311.

Odell et al., "Identification of DNA sequences required for activity of the cauliflower mosaic virus 35S promoter", Nature (1985); vol. 313: 810-812.

Ogas et al., "Cellular Differentiation Regulated by Gibberellin in the *Arabidopsis thaliana pickle* Mutant", Science (1997); vol. 277: 91-94.

Ogryzko et al., "The Transcriptional Coactivators p300 and CBP Are Histone Acetyltransferases", Cell (1996); vol. 87: 953-959.

Pazin et al., "What's up and Down with Histone Deacetylation and Transcription?", Cell (1997); vol. 89: 325-328.

Pysh et al., "The GRAS gene family in *Arabidopsis*: sequence characterization and basic expression analysis of the *Scarecrow-Like* genes", The Plant Journal (1999); vol. 18, No. 1: 111-119.

Quinn, Patrick G., "Distinct Activation Domains within cAMP Response Element-binding Protein (CREB) Mediate Basal and cAMP-stimulated Transcription", The Journal of Biological Chemistry (1993); vol. 268, No. 23: 16999-17009.

Ridgway et al., "CAF-1 and the inheritance of chromatin states: at the crossroads of DNA replication and repair", Journal of Cell Science (2000); vol. 113: 2647-2658.

Rizzo et al., "Unique Strains of SV40 in Commercial Poliovaccines from 1955 Not Readily Indetifiable with Current Testing for SV40 Infection", Cancer Research (1999); vol. 59: 6103-6108.

Robbins et al., "Two Interdependent Basic Domains in Nucleoplasmin Nuclear Targeting Sequence: Identification of a Class of Bipartite Nuclear Targeting Sequence", Cell (1991); vol. 64: 615-623.

Rundlett et al., "HDA1 and RPD3 are members of distinct yeast histone deacetylase complexes that regulate silencing and transcription", Proceedings of the National Academy of Sciences in the USA (1996); vol. 93: 14503-14508.

Salter et al., "Characterization of the ethanol-inducible *alc* gene expression system for transgenic plants", The Plant Journal (1998); vol. 16, No. 1: 127-132.

Sardana et al., "Construction and rapid testing of synthetic and modified toxin gene sequences *CryIA (b & c)* by expression in maize endosperm culture", Plant Cell Reports (1996); vol. 15: 677-681.

Scheres et al., "Mutations affecting the radial organisation of the *Arabidopsis* root display specific defects throughout the embryonic axis", Development (1995); vol. 121: 53-62.

Schumacher et al., "The *Lateral suppressor (Ls)* gene of tomato encodes a new member of the VHIID protein family", Proceeding of the National Academy of Sciences in the USA (1999); vol. 96: 290-295.

Shaywitz et al., "Magnitude of the CREB-Dependent Transcriptional Response Is Determined by the Strength of the Interaction between the Kinase-Inducible Domain of CREB and the KIX Domain of CREB-Binding Protein", Molecular and Cellular Biology (2000); vol. 20, No. 24: 9409-9422.

Silverstone et al., "The *Arabidopsis RGA* Gene Encodes a Transcriptional Regulator Repressing the Gibberellin Signal Transduction Pathway", The Plant Cell (1998); vol. 10: 155-169.

Stockinger et al., "*Arabidopsis thaliana CBF1* encodes an AP2 domain-containing transcriptional activator that binds to the C-repeat/DRE, a cis-acting DNA regulatory element that stimulates transcription in response to low temperature and water deficit", Proceedings of the National Academy of Sciences in the USA (1997); vol. 94: 1035-1040.

Stockinger et al., "Transcriptional adaptor and histone acetyltransferase proteins in *Arabidopsis* and their interactions with CBF1, a transcriptional activator involved in cold-regulated gene expression", Nucleic Acids Research (2001), vol. 29, No. 7: 1524-1533.

Struhl, Kevin, "Histone acetylation and transcriptional regulatory mechanisms", Genes & Development (1998); vol. 12: 599-606.

Tian et al., "Blocking histone deacetylation in *Arabidopsis* induces pleiotropic effects on plant gene regulation and development", Proceedings of the National Academy of Sciences (2001); vol. 98, No. 1: 200-205.

Tian et al., "*Arabidopsis* SHY2/IAA3 Inhibits Auxin-Regulated Gene Expression", The Plant Cell (2002); vol. 14: 301-319.

Ulmasov et al., "Aux/IAA Proteins Repress Expression of Reporter Genes Containing Natural and Highly Active Synthetic Auxin Response Elements", The Plant Cell (1997); vol. 9: 1963-1971.

van der Krol et al., "The Basic Domain of Plant B-ZIP Proteins Facilitates Import of a Reporter Protein into Plant Nuclei", The Plant Cell (1991); vol. 3: 667-675.

Varagona et al., "Monocot Regulatory Protein Opaque-2 Is Localized in the Nucleus of Maize Endosperm and Transformed Tobacco Plants", The Plant Cell (1991); vol. 3: 105-113.

Varagona et al., "Nuclear Localization Signal(s) Required for Nuclear Targeting of the Maize Regulatory Protein Opaque-2", The Plant Cell (1992); vol. 4: 1213-1227.

Verbsky et al., "Chromatin remodeling in plants", Current Opinion in Plant Biology (2001); vol. 4: 494-500.

Verdel et al., "Identification of a New Family of Higher Eukaryotic Histone Deacetylases", The Journal of Biological Chemistry (1999); vol. 274, No. 4: 2440-2445.

Vidal et al., "*RPD3* Encodes a Second Factor Required To Achieve Maximum Positive and Negative Transcriptional States in *Saccharomyces cervisiae*", Molecular and Cellular Biology (1991); vol. 11, No. 12: 6317-6327.

Weissbach et al. (1999), *Methods for Plant Molecular Biology*, Academy Press, New York VIII: 421-463.

Wu et al., "Functional analysis of a *RPD3* histone deacetylase homologue in *Arabidopsis thaliana*", Plant Molecular Biology (2000); vol. 44: 167-176.

Wu et al., "Functional analysis of HD2 histone deacetylase homologues in *Arabidopsis thaliana*", The Plant Journal (2000); vol. 22, No. 1: 19-27.

Xu et al., "Rice Triosephosphate Isomerase Gene 5' Sequence Directs β-Glucuronidase Activity I Transgenic Tobacco but Requires an Intron for Expression in Rice", Plant Physiology (1994); vol. 106: 459-467.

Yanofsky et al., "The protein encoded by the *Arabidopsis* homeotic gene *agamous* resembles transcription factors", Nature (1990); vol. 346: 35-39.

Zenser et al., "Auxin modulates the degradation rate of Aux/IAA proteins", Proceedings of the National Academy of Sciences (2001); vol. 98, No. 20: 11795-11800.

Zhang et al., "Analysis of Rice *Act1* 5' Region Activity in Transgenic Rice Plants", The Plant Cell (1991); vol. 3: 1155-1165.

Zhu et al., "Targeted manipulation of maize genes in vivo using chimeric RNA/DNA oligonucleotides", Proceedings of the National Academy of Sciences in the USA (1999); vol. 96: 8768-8773.

Mehra-Chaudhary et al., "Msx3 protein recruits histone deacetylase to down-regulate the *Msx1* promoter," Biochem. J. (2001) 353: 13-22.

Jenster et al., "Steroid receptor induction of gene transcription: A two-step model," Proc. Natl. Acad. Sci. USA (1997) vol. 94: 7879-7884.

Murfett et al., "Identification of *Arabidopsis* Histone Deacetylase HDA6 Mutants That Affect Transgene Expression," The Plant Cell (2001) vol. 13: 1047-1061.

Ma et al., "Plant Antibodies for Immunotherapy," Plant Physiol. (1995) 109: 341-346.

Wade et al., "Histone acetylation: chromatin in action", Trends in Biochemical Sciences (1997); 22: 128-132.

Hampsey, "A Saga of histone acetylation and gene expression", Trends in Genetics (1997); 13: 427-429.

Brown et al., "The many Hats of transcription coactivators", Trends in Biochemical Sciences (2000); 25: 15-19.

Notice of Allowance for U.S. Appl. No. 10/995,951, filed Nov. 23, 2004.

Nagy et al., "Nuclear Receptor Repression Mediated by a Complex Containing SMRT, mSin3A, and Histone Deacetylase", Cell (1997); 89: 373-380.

Sabatini et al., "An Auxin-Dependent Distal Organizer of Pattern and Polarity in the *Arabidopsis* Root", Cell (1999); 99: 463-472.

Shetty et al., "Transciptional autorepression of Msxl gene is mediated by interactions of Msxl protein with a multi-protein transcriptional complex containing TATA-binding protein, Sp1 and cAMP-response-element binding protein-binding protein (CBP/p300)." Biochem. J. 339(1999): 751-758.

Notice of Allowance mailed Feb. 25, 2009 for co-pending U.S. Appl. No. 11/067,425.

* cited by examiner

| | | | | | | | | | | | | | | |
|---|---|---|---|---|---|---|---|---|---|---|---|---|---|---|
| M | T | E | T | A | Y | G | N | A | Q | D | L | L | V | E | WT-ROS |
| M | T | E | T | A | Y | G | N | A | Q | D | L | L | V | E | SYNROS |
| M | T | D | M | A | T | G | N | A | P | E | L | L | V | E | ROS-R |
| M | T | E | T | A | Y | G | N | A | Q | D | L | L | V | E | ROS-AR |
| M | T | E | T | S | L | G | T | S | N | E | L | L | V | E | MUC-R |
| L | T | A | D | I | V | A | A | Y | V | S | N | H | V | V | WT-ROS |
| L | T | A | D | I | V | A | A | Y | V | S | N | H | V | V | SYNROS |
| L | T | A | D | I | V | A | A | Y | V | S | N | H | V | V | ROS-R |
| L | T | A | D | I | V | A | A | Y | V | S | N | H | V | V | ROS-AR |
| L | T | A | E | I | V | A | A | Y | V | S | N | H | V | V | MUC-R |
| P | V | T | E | L | P | G | L | I | S | D | V | H | T | A | WT-ROS |
| P | V | T | E | L | P | G | L | I | S | D | V | H | T | A | SYNROS |
| P | V | S | D | L | A | N | L | I | S | D | V | H | S | A | ROS-R |
| P | V | T | E | L | P | G | L | I | S | D | V | H | T | A | ROS-AR |
| P | V | A | E | L | P | T | L | I | A | D | V | H | S | A | MUC-R |
| L | S | G | T | S | A | P | A | S | V | A | V | N | V | E | WT-ROS |
| L | S | G | T | S | A | P | A | S | V | A | V | N | V | E | SYNROS |
| L | S | N | T | S | V | P | Q | P | A | A | A | V | V | E | ROS-R |
| L | S | G | T | S | A | P | A | S | V | A | V | N | V | E | ROS-AR |
| L | N | N | T | T | A | P | A | P | V | V | V | P | V | E | MUC-R |
| K | Q | K | P | A | V | S | V | R | K | S | V | Q | D | D | WT-ROS |
| K | Q | K | P | A | V | S | V | R | K | S | V | Q | D | D | SYNROS |
| K | Q | K | P | A | V | S | V | R | K | S | V | Q | D | E | ROS-R |
| K | Q | K | P | A | V | S | V | R | K | S | V | Q | D | D | ROS-AR |
| K | P | K | P | A | V | S | V | R | K | S | V | Q | D | D | MUC-R |
| H | I | V | C | L | E | C | G | G | S | F | K | S | L | K | WT-ROS |
| H | I | V | C | L | E | C | G | G | S | F | K | S | L | K | SYNROS |
| Q | I | T | C | L | E | C | G | G | N | F | K | S | L | K | ROS-R |
| H | I | V | C | L | E | C | G | G | S | F | K | S | L | K | ROS-AR |
| Q | I | T | C | L | E | C | G | G | T | F | K | S | L | K | MUC-R |
| R | H | L | T | T | H | H | S | M | T | P | E | E | Y | R | WT-ROS |
| R | H | L | T | T | H | H | S | M | T | P | E | E | Y | R | SYNROS |
| R | H | L | M | T | H | H | S | L | S | P | E | E | Y | R | ROS-R |
| R | H | L | T | T | H | H | S | M | T | P | E | E | Y | R | ROS-AR |
| R | H | L | M | T | H | H | N | L | S | P | E | E | Y | R | MUC-R |
| E | K | W | D | L | P | V | D | Y | P | M | V | A | P | A | WT-ROS |
| E | K | W | D | L | P | V | D | Y | P | M | V | A | P | A | SYNROS |
| E | K | W | D | L | P | T | D | Y | P | M | V | A | P | A | ROS-R |
| E | K | W | D | L | Q | V | D | Y | P | M | V | A | P | A | ROS-AR |
| D | K | W | D | L | P | A | D | Y | P | M | V | A | P | A | MUC-R |
| Y | A | E | A | R | S | R | L | A | K | E | M | G | L | G | WT-ROS |
| Y | A | E | A | R | S | R | L | A | K | E | M | G | L | G | SYNROS |
| Y | A | E | A | R | S | R | L | A | K | E | M | G | L | G | ROS-R |
| Y | A | E | A | R | S | R | L | A | K | E | M | G | L | G | ROS-AR |
| Y | A | E | A | R | S | R | L | A | K | E | M | G | L | G | MUC-AR |
| Q | R | R | K | A | N | R | | | | | | | | | WT-ROS |
| Q | R | R | K | A | N | R | P | K | K | K | R | K | V | | SYNROS |
| Q | R | R | K | R | G | R | G | | | | | | | | ROS-R |
| Q | R | R | K | A | N | R | | | | | | | | | ROS-AR |
| Q | R | R | K | R | G | R | G | K | | | | | | | MUC-AR |

FIG. 1A

| | | | |
|---|---|---|---|
| GCGGATCCCC | GGGTATGACT | GAGACTGCTT | ACGGTAACGC |
| TCAGGATCTT | CTTGTTGAGC | TTACTGCTGA | TATCGTTGCT |
| GCTTACGTTT | CTAACCACGT | TGTTCCTGTT | ACTGAGCTTC |
| CTGGACTTAT | CTCTGATGTT | CATACTGCAC | TTTCTGGAAC |
| ATCTGCTCCT | GCTTCTGTTG | CTGTTAACGT | TGAGAAGCAG |
| AAGCCTGCTG | TTTCTGTTCG | TAAGTCTGTT | CAGGATGATC |
| ATATCGTTTG | TTTGGAGTGT | GGTGGTTCTT | TCAAGTCTCT |
| CAAGCGTCAC | CTTACTACTC | ATCACTCTAT | GACTCCAGAG |
| GAGTATAGAG | AGAAGTGGGA | TCTTCCTGTT | GATTACCCTA |
| TGGTTGCTCC | TGCTTACGCT | GAGGCTCGTT | CTCGTCTCGC |
| TAAGGAGATG | GGTCTCGGTC | AGCGTCGTAA | GGCTAACCGT |
| CCAAAAAAGA | AGCGTAAGGT | CTGAGAGCTC | GC |

FIG. 1B

```
  M   T   E   T   A   Y   G   N   A   Q   D   L   L   V   E
ATG ACN GAR ACN GCN TAY GGN AAY GCN CAR GAY YTN YTN GTN GAR

L   T   A   D   I   V   A   A   Y   V   S   N   H   V   V
YTN ACN GCN GAY ATH GTN GCN GCN TAY GTN WSN AAY CAY GTN GTN

P   V   T   E   L   P   G   L   I   S   D   V   H   T   A
CCN GTN ACN GAR YTN CCN GGN YTN ATH WSN GAY GTN CAY ACN GCN

L   S   G   T   S   A   P   A   S   V   A   V   N   V   E
YTN WSN GGN ACN WSN GCN CCN GCN WSN GTN GCN GTN AAY GTN GAR

K   Q   K   P   A   V   S   V   R   K   S   V   Q   D   D
AAR CAR AAR CCN GCN GTN WSN GTN MGN AAR WSN GTN CAR GAY GAY

H   I   V   C   L   E   C   G   G   S   F   K   S   L   K
CAY ATH GTN TGY YTN GAR TGY GGN GGN WSN TTY AAR WSN YTN AAR

R   H   L   T   T   H   H   S   M   T   P   E   E   Y   R
MGN CAY YTN ACN ACN CAY CAY WSN ATG ACN CCN GAR GAR TAY MGN

E   K   W   D   L   P   V   D   Y   P   M   V   A   P   A
GAR AAR TGG GAY YTN CCN GTN GAY TAY CCN ATG GTN GCN CCN GCN

Y   A   E   A   R   S   R   L   A   K   E   M   G   L   G
TAY GCN GAR GCN MGN WSN MGN YTN GCN AAR GAR ATG GGN YTN GGN

Q   R   R   K   A   N   R   P   K   K   K   R   K   V
CAR MGN MGN AAR GCN AAY MGN CCN AAR AAR AAR MGN AAR GTN
```

FIG. 1C

ROS Inverted Repeat
DNA Binding Sites(Operator sequences)

TATATTTCAA-TTTTA-TTGTAATATA   *virC/virD*
\*\*\*\* \*\* \*\* \* \*\*\* \*\*\* \*\*
TATAATTAAAATATTAACTGTCGCATT   *ipt*

FIG. 1D

Comparison of ROS DNA Binding Site (Operator) Sequences

| | |
|---|---|
| *VirC/VirD* | TATATTTCAA |
| | TATATTACAA |
| *ipt* | TATAATTAAA |
| | AATGCGACAG |
| | TATAHTtCAA |
| | a    g gaa g |
| Consensus | WATDHWKMAR |

FIG. 1E p74-315 p74-316 p74-309 p74-118 p76-507 p76-508 p75-101 p74-501

Columbia wt
pB1121
p74-501
buffer
FIG. 9

```
bnKCP    (1)    M-AGGGPTFSIELSAYG-SDLPTDKASGDIP------NEEGSGLSRVGSGIW
atKCP    (1)    MELMAKPTFSIEVSQYGTTDLPATEKASSSSSSFETTNEEG-VEESGLSRIW
atKCL1   (1)    M--------EVLVGSTFRDRSSVTTHDQAVP--------AS-LSSRIGLRRC
atKCL2   (1)    M---VGSSFGIGMAAYVRDHRGVSAQDKAVQTALFLADESGRGGSQIGIGLR bnKCP    (45)   SG----RTVDYSSESSSSIGTPGDSEEEDEESEEDNDEEEL------GLASL
atKCP    (52)   SG----QTADYSSDSSS-IGTPGDSEEDEEESENENDDVSSKELGLRGLASM
atKCL1   (36)   GR-------SPPPESSSSVGETSENEEDEDDAVSSSQGRWLN------SFS
atKCL2   (50)   MSNNNNKSPEESSDSSSSIGESSENEEEEEEDDAVSCQRGTLD------SFS
                                                                ********
bnKCP    (87)   RSLEDSLPSK-GLSSHYKGKSKSFGNLGEIG-SVKEVPKQENPLNKKRRLQI
atKCP    (99)   SSLEDSLPSKRGLSNHYKGKSKSFGNLGEIG-SVKEVAKQENPLNKRRRLQI
atKCL1   (74)   SSLEDSLPIKRGLSNHYIGKSKSFGNLMEAS-NTNDLVKVESPLNKRRRLLI
atKCL2   (96)   SSLEDSLPIKRGLSNHYVGKSKSFGNLMEAASKAKDLEKVENPFNKRRRLVI bnKCP    (137)  YNKLARKS------FYSWQNPKSMPLLPVHEDNDDEEGDDG-----------
atKCP    (150)  CNKLARKS------FYSWQNPKSMPLLPVNEDEDDDDEDDDEEDLKSGFDEN
atKCL1   (125)  ANKLRRRSSLSSFSIYTKINPNSMPLLALQESDNEDHKLNDDDDDDDS---S
atKCL2   (148)  ANKLRRR------------GRSITYEEDHHIHNDDYEDDDG-----------

◊◊◊◊
bnKCP    (172)  -DLSDEERGGDVLARRPSFKNRALKSMSCFALSDLQEEEE----EEEDE
atKCP    (196)  KSSSDEEGVKKVVVRKGSFKNRAYKSRSCFALSDLIEEED----DDDDQ
atKCL1   (174)  SDDETSKLKEKRMKMTNHRDFMVPQTKSCFSLTSFQDDDDR--------
atKCL2   (177)  ----DGDDHRKIMMMKNKKELMAQTRSCFCLSSLQEEDDGDGDDDEDE
```

FIG. 10A

```
              ••••
bnKCP    GDDGDLSDEERGGDVLARRPSFKNRALKSMSCFALSDLQEEE
ATF-1    DSSDSIGSSQQAHGILARRPSYRKILKDLSSEDTRGRKGDGE
hyCREB   ESVDSVTDSQKRREILSRRPSYRKILNDLSSDAPGVPRIEEE
CREB     ESVDSVTDSQKRREILSRRPSYRKILNDLSSDAPGVPRIEEE
CREM     SADSEVIDSHKRREILSRRPSYRKILNELSSDVPGIPKIEEE
cCREM    AESEGVIDSHKRREILSRRPSYRKILNELSSDVPGVPKIEEE
```

Fig. 13A
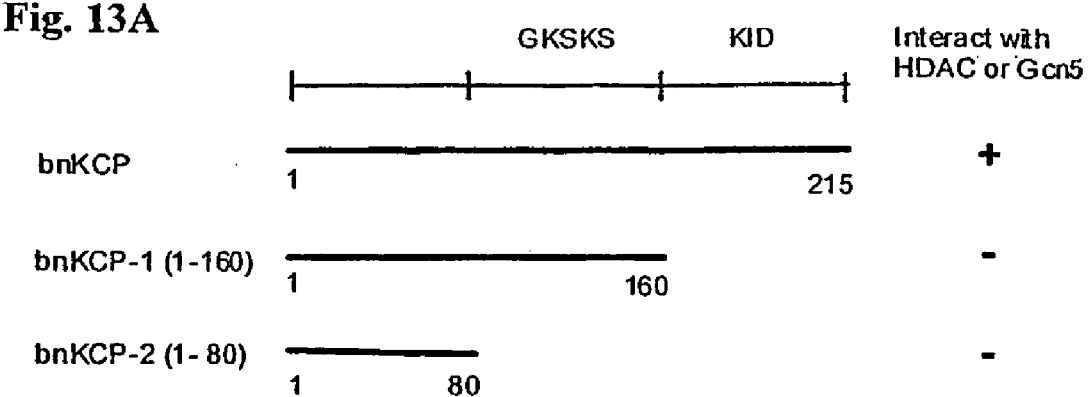
Fig. 13B
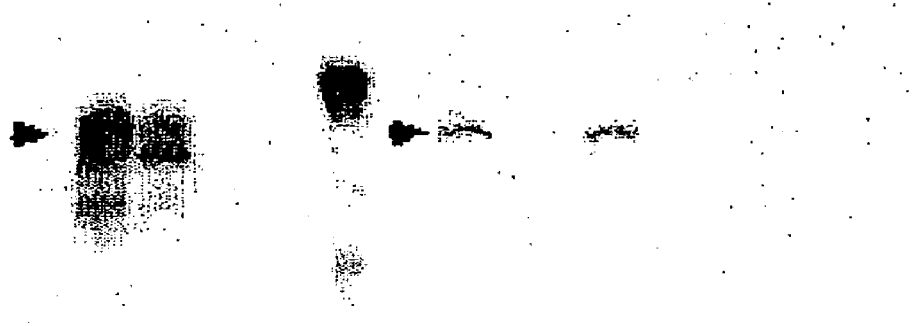
FIG. 13

Fig. 13C-1
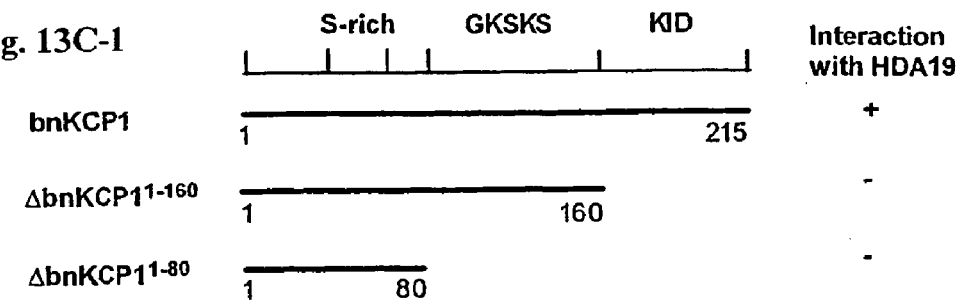
Fig. 13C-2
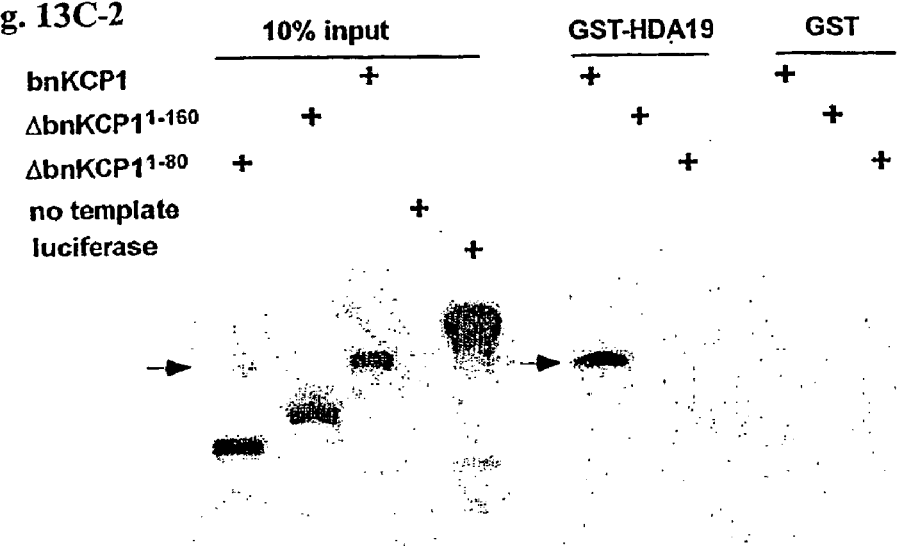
Fig. 13C-3
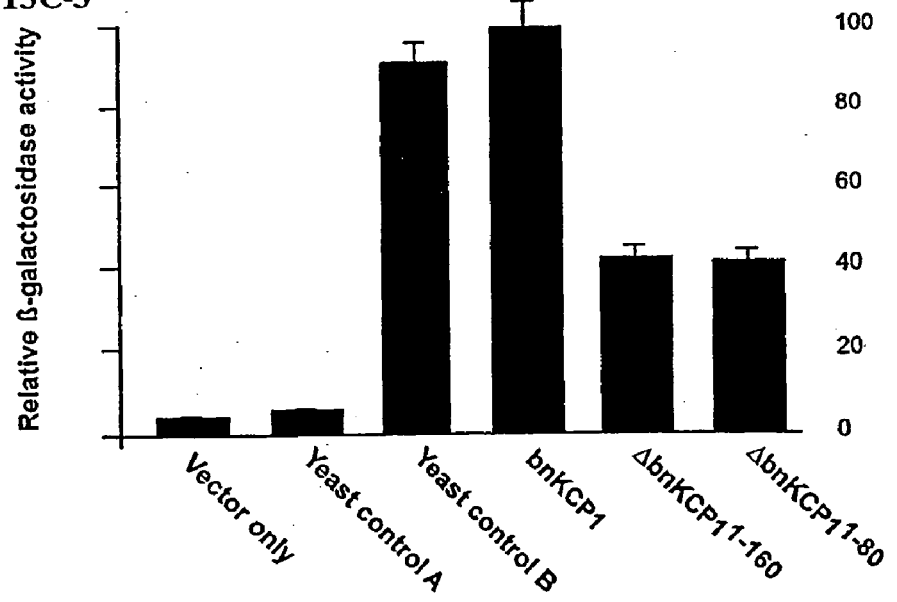
FIG. 13 cont'd Wild type KID   GDDGDLSDEERGGDVLARRPSFKNRALKSMSCFALSDLQEEE
(RRPS$^{188}$)

Mutant KID   GDDGDLSDEERGGDVLARRPGFKNRALKSMSCFALSDLQEEE
(RRPG$^{188}$)

Fig. 16A
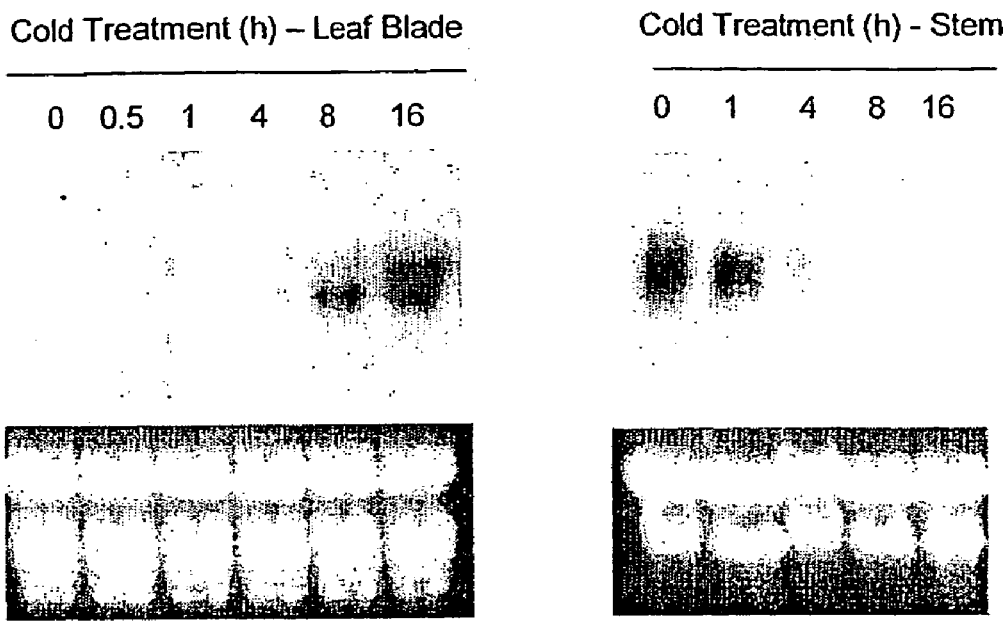
Fig. 16B
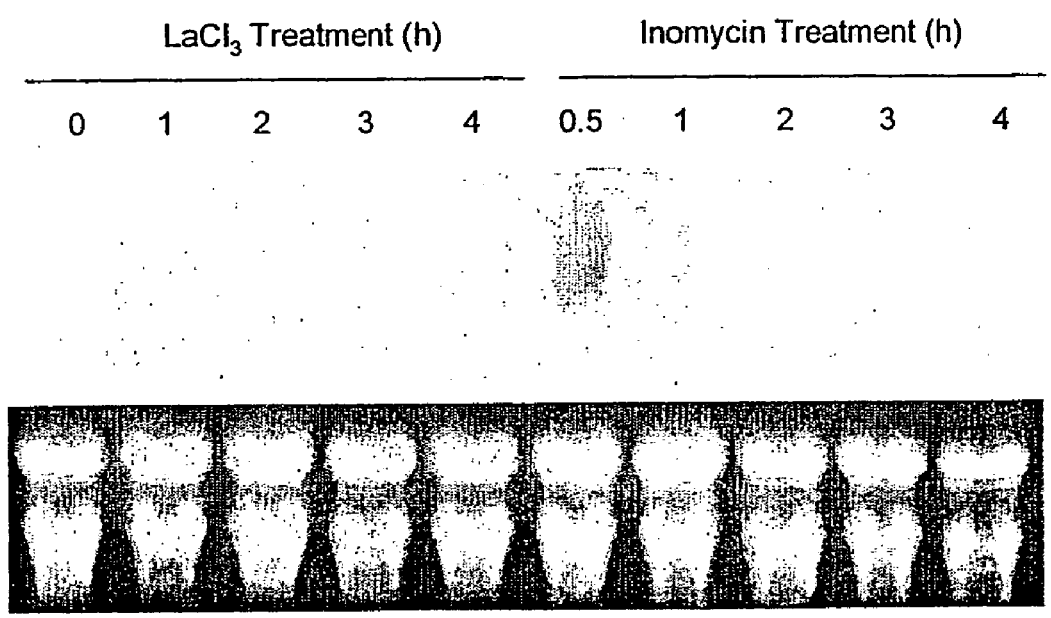
FIG. 16

Fig. 17A
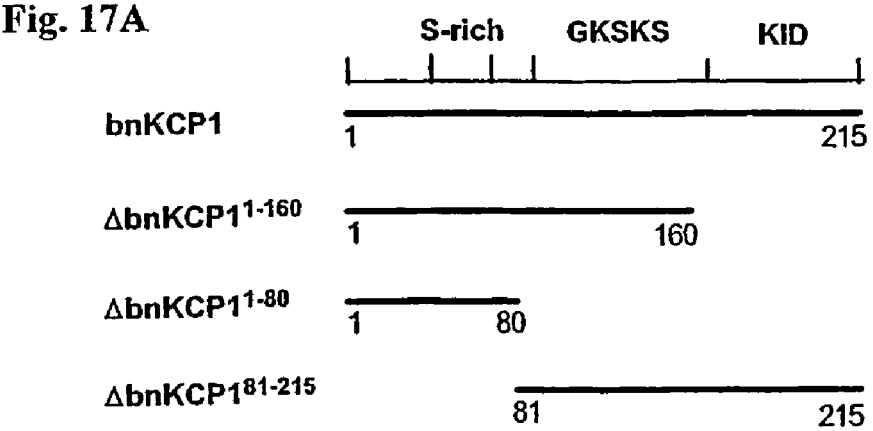
Fig. 17B
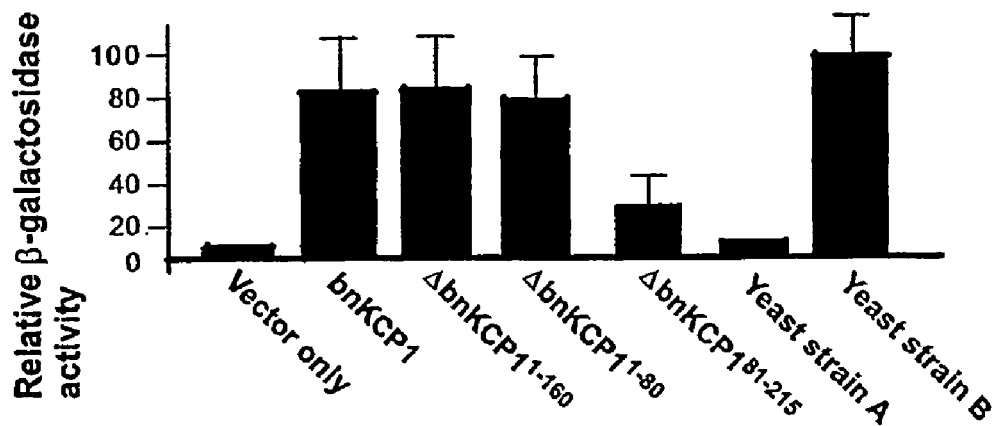
FIG. 17

Fig. 18A
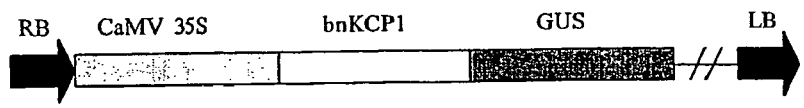
Fig. 18B
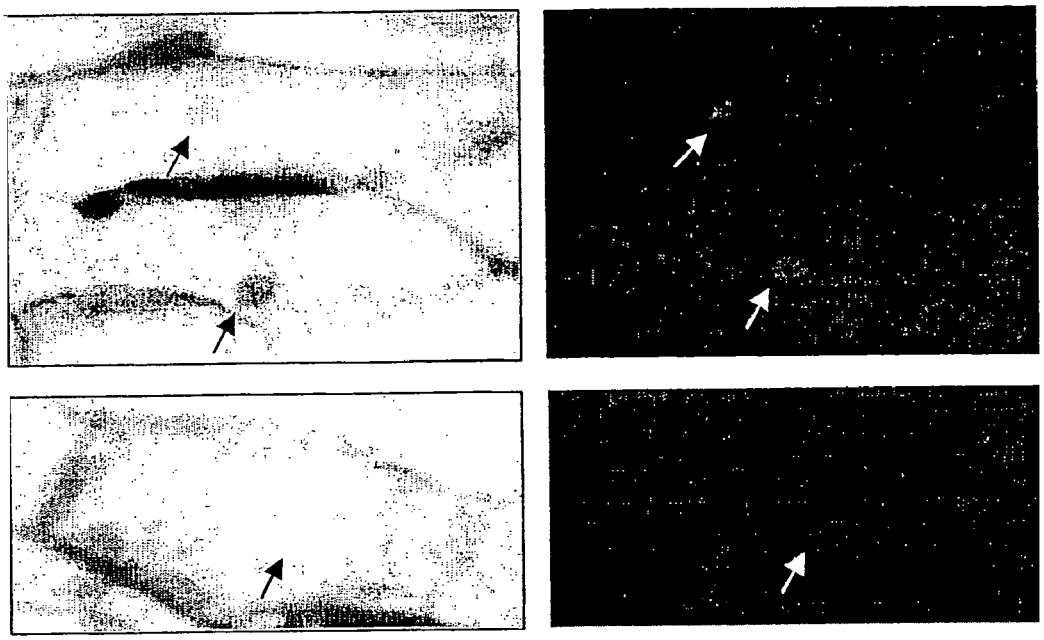
FIG. 18

```
BnSCL1    (1)    MKLQASSPQDNQ-----PSNT--------------------------------
AtSCL15   (1)    MKIPASSPQDTT-----NNNN--------------------------------
LeSCL     (1)    MKVPFSTNDNVSSKPLVNSNNSFTFPAATNGSNLCYEPKSVLELRRSPSP

BnSCL1    (17)   --------------TNNSTDSNHLSMDEHAMR-SMDWDSIMKELEVDDDSA
AtSCL15   (17)   --------------NTNSTDSNHLSMDEHVMR-SMDWDSIMKELELDDDSA
LeSCL     (51)   IVDKQIITTNPDLSALGGGEDPLQLGDHVLSNFEDWDSLMRELGLHDDSA

BnSCL1    (53)   PYDLQP---S----S----------FNLPVFPD-------IDSSDVYPGPN
AtSCL15   (53)   PNSLKTGFTTTTTDSTILPLYAVDSNLPGFPDQIQPSDFESSSDVYPGQN
LeSCL     (101)  SLSKTNPLTHSESLTQFHNLSEFSAESNQFPSPDFSFSDTNFPQFPTVN

BnSCL1    (80)   QITGYGFNSLDSVDNG----GFDYIEDLIRVVDCIESDELHLAHVVLSQL
AtSCL15   (103)  QTTGYGFNSLDSVDNG----GFDFIEDLIRVVDCVESDELQLAGVVLSRL
LeSCL     (151)  QASFINALELSGDIHQNWSVGFDYVDELIRFAECEETNAKQLAHVILARL
                                                        LHRI
                                                                  * * * * *
BnSCL1    (126)  NQRLQTSAGRPLQRAAFYFKEALGSLLTGTNRN--QLFSWSDIVQKIRAT
AtSCL15   (149)  NQRLRSPAGRPLQRAAFYFKEALGSFLTGSNRNPIRLSSWSEIVQRIRAT
LeSCL     (201)  NQRLRSAAGKPLQRAAFYFKEALQAQLAGSAROT-RSSSSSDVIQEIKSY

BnSCL1    (174)  KEFSGISPIPLFSHFTANQAILDSLSSQSSSPFVHVVDFEIGFGGQYASL
AtSCL15   (199)  KEYSGISPIPLFSHFTANQAILDSLSSQSSSPFVHVVDFEIGFGGQYASL
LeSCL     (250)  KILSNISPIPMFSSFTANQAVLEAVDG---SMEVHVIDFDIGFGGHWASL
                                  VHIID

BnSCL1    (224)  MREIAEKS----ANGGFLRVTAVVAEDCAVETRLVKENLTQFAAEMKIRE
AtSCL15   (249)  MREITEKS----VSGGFLRVTAVVAEECAVETRLVKENLTQFAAEMKIRE
LeSCL     (297)  MKELADKAECRKANAPILRITALVPEEYAVESRLIRENLTQFARELNIGF
                                                          LHRII

BnSCL1    (270)  QIEFVLMKTFEILSFKAIREVDGERTVVLISPAIFRRVIGIAEFVNNLGF
AtSCL15   (295)  QIEFVLMKTFEMLSFKAIREVEGERTVVLISPAIFRRLSGITDFVNNLRF
LeSCL     (347)  EIDFVLIRTFELLSFKAIKFMEGEKTFVLLSPAIFRRVG--SEFVNFLRF
                                                  ■■■■■■■■■■■■■■■■■■■■■■■

BnSCL1    (320)  VSPNVVVFVDSEGCTETAGSGSFRREFVSAEEFYTMVLESIDAAAPPG--
AtSCL15   (345)  VSPKVVVFVDSEGWTEIAGSGSFRREFVSALEFYTMVLESIDAAAPPG--
LeSCL     (395)  ISPNVVVFVDSEGLMGYG-AMSFRQTVIDGLEFYSTLLESIEAANIGGGN
                            PFYRE              ■■■■■■■■■■■■■■■■■■■■■

BnSCL1    (368)  -DLVKKIVETFLLRPKISAAVETAANRRSAGQMTWREMLCAAGMRPVQLS
AtSCL15   (393)  -DLVKKIVEAFVLRPKISAAVETAADRRHTGEMTWREALCAAGMRPIQQS
LeSCL     (444)  CEDWMRKIENFVLFPKIVDMIGAVG--RRGGGSWRDAMVDAGFRPVGTS
                                                                SAW
                                                           * * * * *
BnSCL1    (417)  QFADFQAECLLEKAQVRGFHVAKRQGELVLCWHGRALVATSAWRF
AtSCL15   (442)  QFADFQAECLLEKAQVRGFHVAKRQGELVLCWHGRALVATSAWRF
LeSCL     (492)  QFADFQADCLLGRMQVRGFHVAKRQAEMLLCWHERALVATSAWRC
```

FIG. 20

Fig. 23A
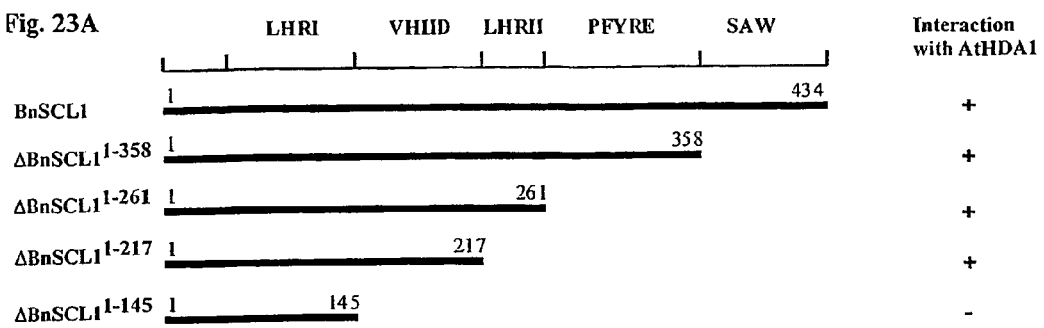
Fig. 23B
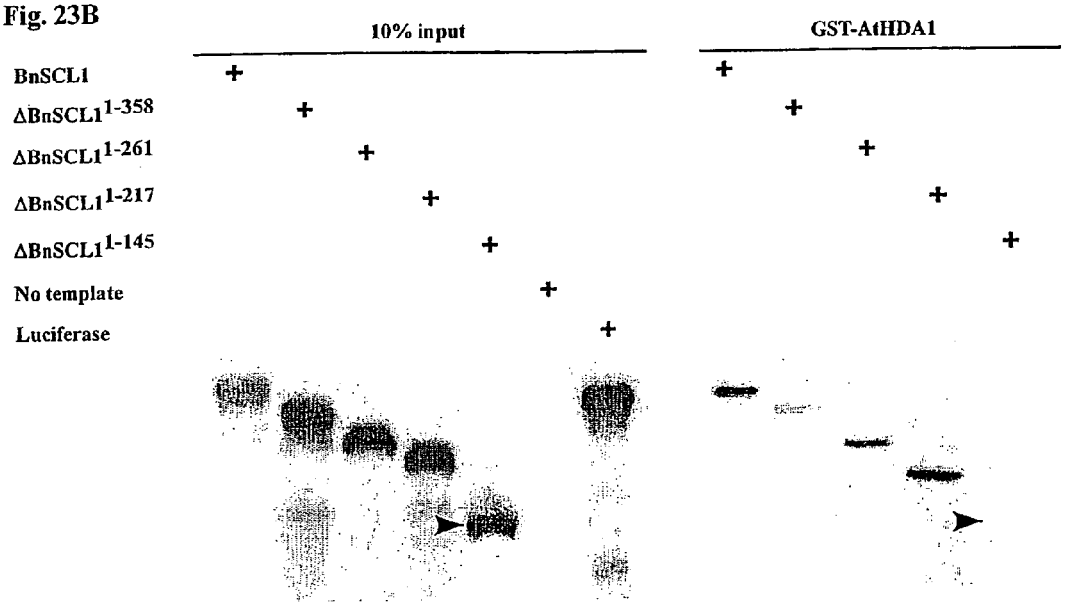
FIG. 23

Fig. 24A
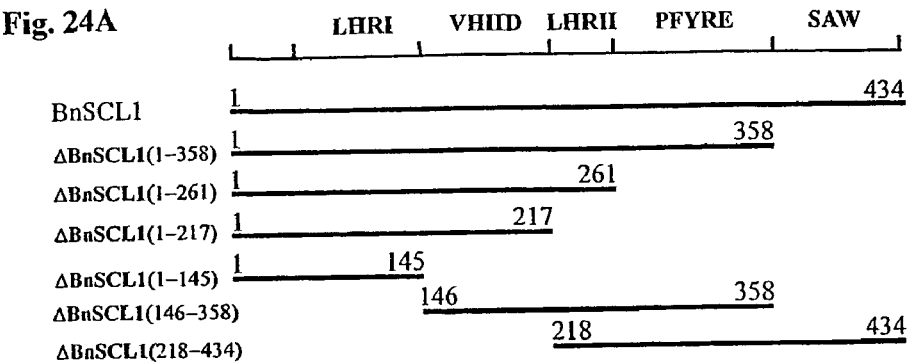
Fig. 24B
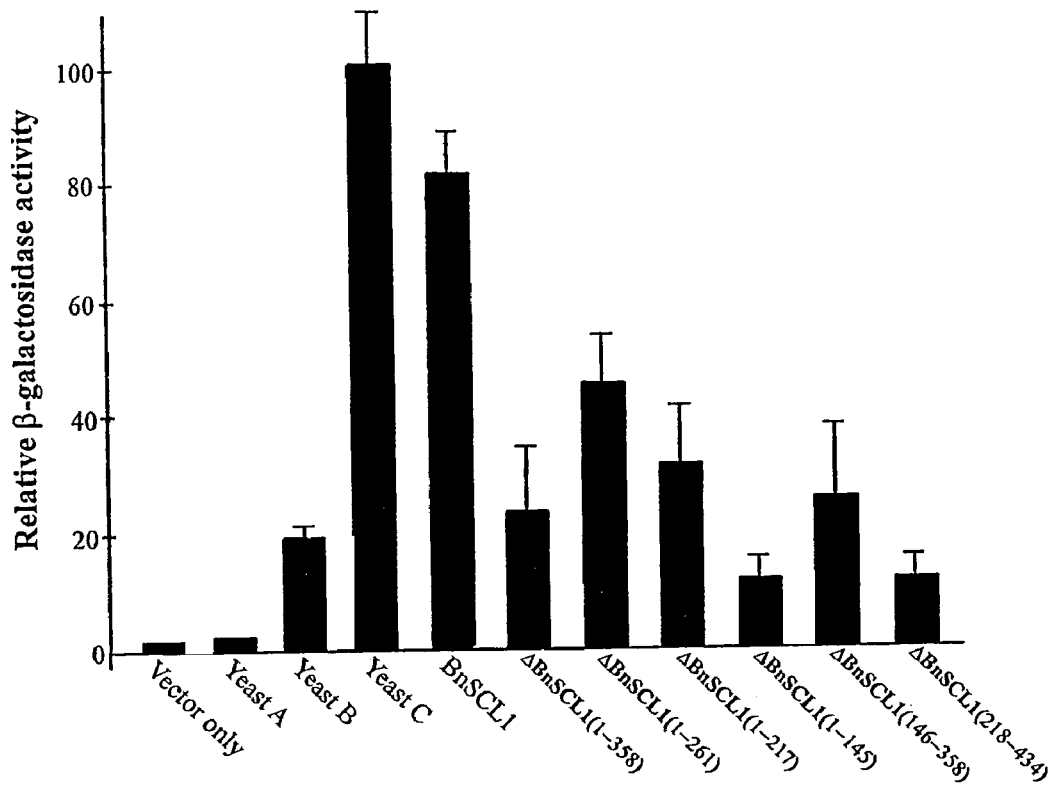
FIG. 24

Fig. 25A
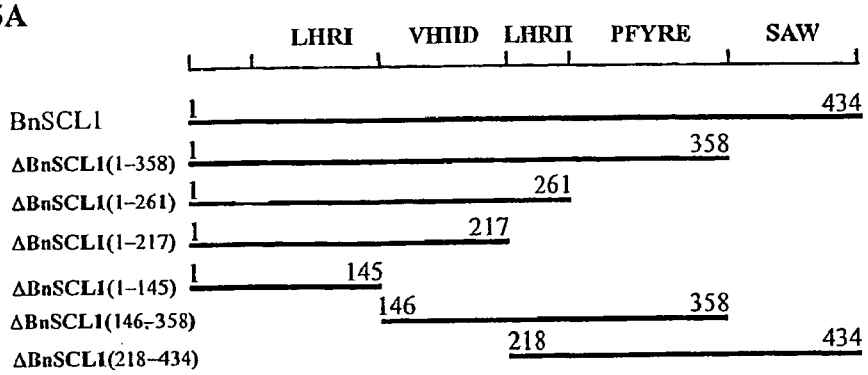
Fig. 25B
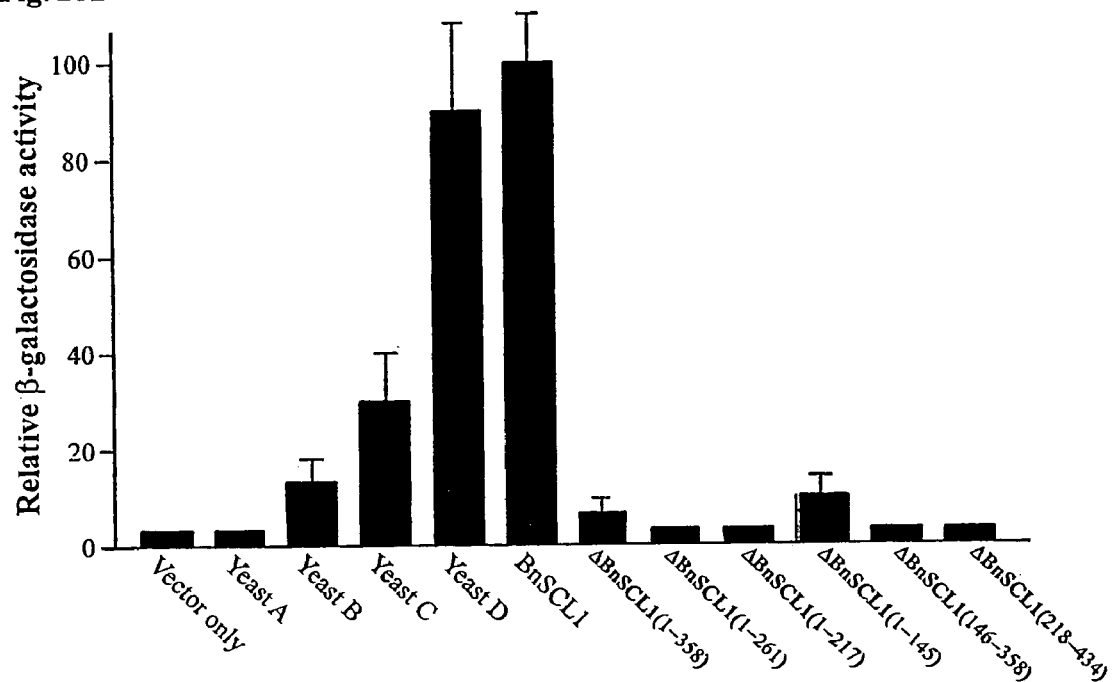
FIG. 25

Fig. 26A
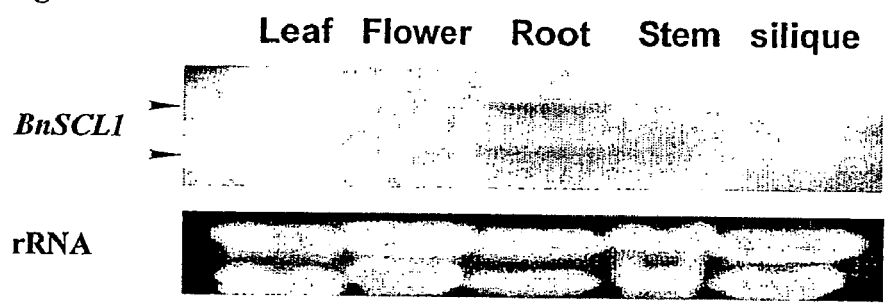
Fig. 26B
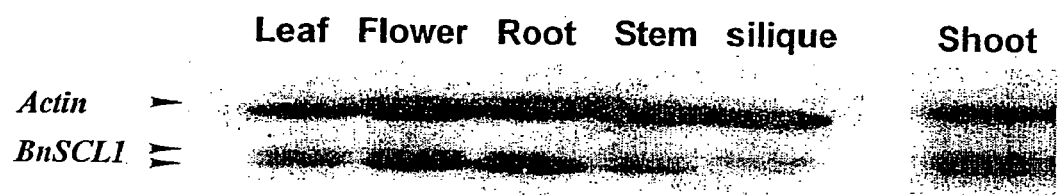
FIG. 26

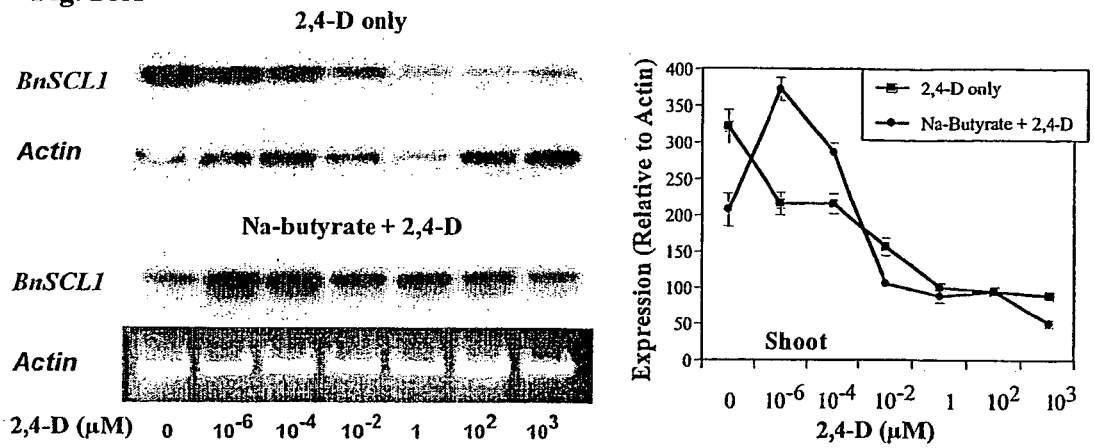
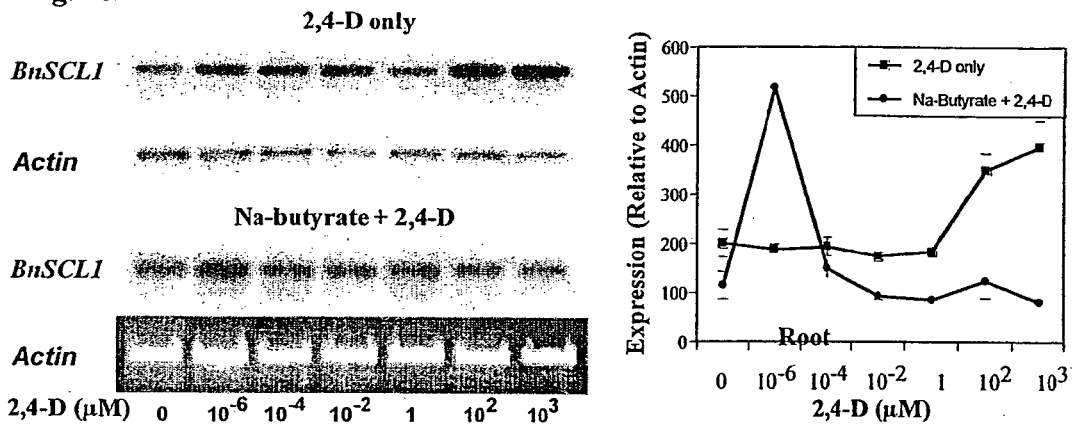
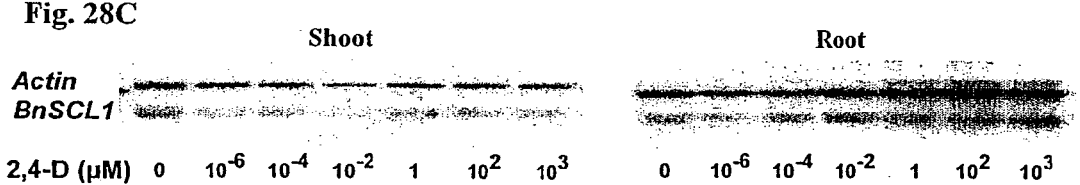
FIG. 28

Fig. 29A
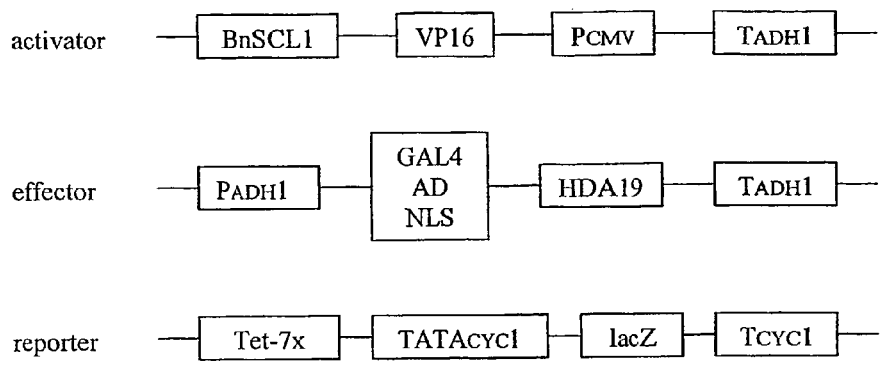
Fig. 29B
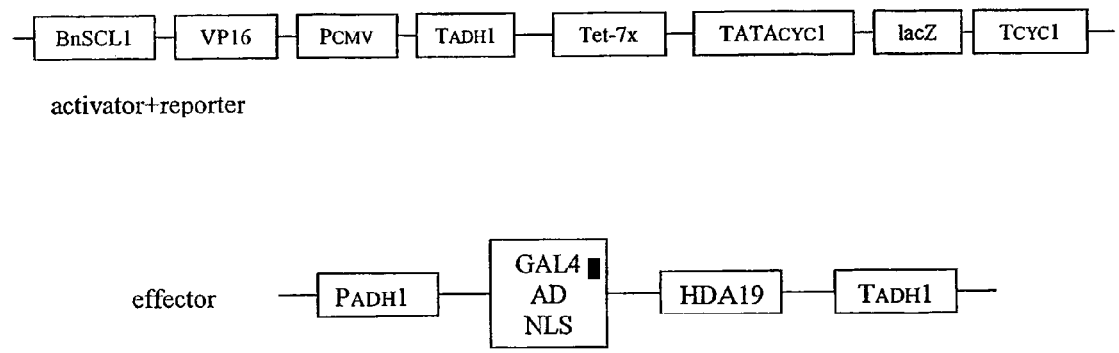
FIG. 29

REGULATION OF GENE EXPRESSION USING CHROMATIN REMODELLING FACTORS

The present invention relates to the regulation of gene expression. More particularly, the present invention relates to the control of gene expression of one or more nucleotide sequences of interest in transgenic plants using chromatin remodelling factors.

BACKGROUND OF THE INVENTION

Transgenic plants have been an integral component of advances made in agricultural biotechnology. They are necessary tools for the production of plants exhibiting desirable traits (e.g. herbicide and insect resistance, drought and cold tolerance), or producing products of nutritional or pharmaceutical importance. As the applications of transgenic plants become ever more sophisticated, it is becoming increasingly necessary to develop strategies to fine-tune the expression of introduced genes. The ability to tightly regulate the expression of transgenes is important to address many safety, regulatory and practical issues. To this end, it is necessary to develop tools and strategies to regulate the expression of transgenes in a predictable manner.

Several strategies have so far been employed to control plant gene/transgene expression. These include the use of regulated promoters, such as inducible or developmental promoters, whereby the expression of genes of interest is driven by promoters responsive to various regulatory factors (Gatz, 1997). Other strategies involve co-suppression (Eisner et al., 1998) or anti-sense technology (Kohno-Murase et al., 1994), whereby plants are transformed with genes, or fragments thereof, that are homologous to genes either in the sense or antisense orientations. Chimeric RNA-DNA oligonucleotides have also been used to block the expression of target genes in plants (Beetham et al., 1999; Zhu et al., 1999).

Posttranslational modifications of histones in chromatin are important mechanisms in the regulation of gene expression. Protein-protein interactions between histones H3, H4, H2A and H2B form an octomeric core which is wrapped with DNA. N-terminal tails of histones protrude from the octamer and are subject to posttranslational modification involving acetylation and deacetylation of conserved lysine residues. A nucleosome comprises 26 lysine residues that may be subject to acetylation. Acetylation of core histones, including H4 and H3 via histone acetyltransferase (HAT), is correlated with transcriptionally active chromatin of eukaryotic cells. Acetylation is thought to weaken the interactions of histones with DNA and induce alterations in nucleosome structure. These alterations enhance the accessibility of promoters to components of the transcription machinery, and increase transcription. HATs have been identified in yeast, insects, plants and mammals (e.g. Kolle et al. 1998), and are typically components of multiprotein complexes including components of RNA polymerase II complex, TFIID, TFIIC and recruitment factors (e.g. see Lusser et al. 2001 for review).

Histone deacetylation, via histone deacetylase (HD, HDA, HDAC), is thought to lead to a less accessible chromatin conformation, resulting in the repression of transcription (e.g. Pazin and Kadonaga, 1997; Struhl, 1998; Lusser et al., 2001). The role of the yeast histone deacetylase, RPD3, in transcriptional repression was first discovered through a genetic screen for transcriptional repressors in *S. cerevisiae* (Vidal and Gaber, 1991). Since then, a number of yeast and mammalian HDAC genes have been cloned (Rundlett et al., 1996; Emiliani et al., 1998; Hassig. et al., 1998; Verdel and Khochbin, 1999). Most eukaryotic histone deacetylases show some sequence homology to yeast RPD3, suggesting that these proteins are all members derived from a single gene family (Khochbin and Wolffe, 1997; Verdel and Khochbin, 1999). In yeast and mammalian cells, the RPD3/HDACs mediate transcriptional repression by interacting with specific DNA-binding proteins or associated corepressors and by recruitment to target promoters (Kadosh and Struhl, 1997; Hassig et al., 1997; Nagy et al., 1997; Gelmetti et al., 1998). Recently, a second family of histone deacetylases, HDA19 and related proteins, were identified in yeast and mammalian cells (Rundlett et al., 1996; Fischle et al., 1999; Verdel and Khochbin, 1999). The deacetylase domain of HDA19-related proteins is homologous to but significantly different from that of RPD3 (Fischle et al., 1999; Verdel and Khochbin, 1999). These proteins also appear to be functionally different from RPD-like proteins in yeast cells (Rundlett et al., 1996). WO 97/35990 discloses mammalian-derived histone deacetylase (HDx) gene sequences, gene products, and uses for these sequences and products. The down regulation of gene expression in plants using histone deacetylase, fused to a DNA binding domain that targeted the fusion protein to a specific gene, has been demonstrated (Wu et al., 2000a; Wu et al., 2000b).

The present invention embraces the use of fusion proteins comprising a DNA binding domain fused to a recruitment factor, that is capable of recruiting chromatin remodelling proteins such as HDAC and HAT, to specific DNA sites to regulate expression of a gene of interest. Also disclosed is the use of fusion proteins comprising a DNA binding portion fused to histone acetyltransferase (HAT) to regulate transcription of a gene of interest.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the regulation of gene expression. More particularly, the present invention relates to the control of gene expression of one or more nucleotide sequences of interest in transgenic plants using chromatin remodelling factors.

According to an aspect of an embodiment of the present invention, there is provided a method to regulate the expression of a gene of interest in a plant comprising:
  i) introducing to the plant:
    1) a first nucleotide sequence comprising,
      a) the gene of interest operatively linked to a first regulatory region,
      b) an operator sequence capable of binding a fusion protein, and;
    2) a second nucleotide sequence comprising a second regulatory region in operative association with a nucleotide sequence encoding a fusion protein, the fusion protein comprising,
      a) a DNA binding protein, or a portion of a DNA binding protein capable of binding the operator sequence, and;
      b) a recruitment factor protein, or a portion thereof, capable of binding a chromatin remodelling protein,
  ii) growing the plant, wherein expression of the second nucleotide sequence produces the fusion protein and regulates expression of the gene of interest.

The present invention also embraces the methods as defined above, wherein the first and second regulatory regions are either the same or different and are selected from the group consisting of a constitutive promoter, an inducible promoter, a tissue specific promoter, and a developmental promoter.

The present invention also relates to a method of enhancing the expression of a gene of interest or enhancing the transcription of a gene of interest in a plant comprising:
  i) introducing to the plant:
    1) a first nucleotide sequence comprising,
      a) the gene of interest operatively linked to a first regulatory region, and;
      b) an operator sequence that interacts with a fusion protein;
    2) a second nucleotide sequence comprising a second regulatory region in operative association with a nucleotide sequence encoding a fusion protein comprising,
      a) a DNA binding protein, or a portion thereof, capable of binding the operator sequence, and;
      b) a histone acetyltransferase (HAT) protein, or portion thereof, capable of increasing histone acetylation;
  ii) growing the plant, wherein expression of the second nucleotide sequence produces the fusion protein and increases transcription of the gene of interest.

The present invention pertains to a method of regulating the expression of a gene of interest or enhancing the transcription of a gene of interest in a plant comprising:
  i) introducing to the plant:
    1) a first nucleotide sequence comprising,
      a) the gene of interest operatively linked to a first regulatory region, and;
      b) an operator sequence that interacts with a fusion protein;
    2) a second nucleotide sequence comprising a second regulatory region in operative association with a nucleotide sequence encoding a fusion protein comprising,
      a) a DNA binding protein, or a portion thereof, capable of binding the operator sequence, and;
      b) a chromatin remodelling factor, or portion thereof, capable of increasing histone acetylation;
  ii) growing the plant, wherein expression of the second nucleotide sequence produces the fusion protein and regulates the transcription of the gene of interest.

The present invention also embraces the methods as defined above, wherein the first and second regulatory regions are either the same or different and are selected from the group consisting of a constitutive promoter, an inducible promoter, a tissue specific promoter, and a developmental promoter.

The first and second nucleotide sequences may be placed within the same or within different vectors, genetic constructs, or nucleic acid molecules. Preferably, the first nucleotide sequence and the second nucleotide sequence are chromosomally integrated into a plant or plant cell. The two nucleotide sequences may be integrated into two different genetic loci of a plant or plant cell, or the two nucleotide sequences may be integrated into a singular genetic locus of a plant or plant cell. However, the second nucleotide sequence may be integrated into the DNA of the plant or it may be present as an extra-chromosomal element, for example, but not wishing to be limiting a plasmid.

Also, according to the present invention there is provided a method for selectively controlling the transcription of a gene of interest, comprising:
  i) producing a first plant comprising a first genetic construct, the first genetic construct comprising a first regulatory region operatively linked to the gene of interest and at least one operator sequence capable of binding a fusion protein;
  ii) producing a second plant comprising a second genetic construct, the second genetic construct comprising a second regulatory region in operative association with a nucleic sequence encoding the fusion protein, the fusion protein comprising,
    a) a DNA binding protein, or a portion thereof, capable of binding the operator sequence, and;
    b) a recruitment factor protein, or a portion thereof, capable of binding a chromatin remodelling protein;
  iii) crossing the first plant and the second plant to obtain progeny comprising both the first genetic construct and the second genetic construct, the progeny characterized in that the expression of the fusion protein regulates expression of the gene of interest.

The present invention also embraces the methods as defined above, wherein the first and second regulatory regions are either the same or different and are selected from the group consisting of a constitutive promoter, an inducible promoter, a tissue specific promoter, and a developmental promoter.

The present invention also pertains to the method as just defined, wherein the nucleic acid sequence encoding the fusion protein is optimised for expression in a plant, and that the nucleotide sequence encodes a nuclear localization signal.

Also, according to the present invention there is provided a method for selectively controlling the transcription of a gene of interest, comprising:
  i) producing a first plant comprising a first genetic construct, the first genetic construct comprising a first regulatory region operatively linked to the gene of interest and at least one operator sequence capable of binding a fusion protein;
  ii) producing a second plant comprising a second genetic construct, the second genetic construct comprising a second regulatory region in operative association with a nucleic sequence encoding the fusion protein comprising,
    a) a DNA binding protein, or a portion thereof, capable of binding the operator sequence, and;
    b) a HAT protein, or portion thereof, capable of histone acetylation in plants;
  iii) crossing the first plant and the second plant to obtain progeny comprising both the first genetic construct and the second genetic construct and characterized in that the expression of the fusion protein up-regulates the expression of the gene of interest.

The present invention also provides the method as just defined, wherein, the nucleic acid sequence encoding the fusion protein is optimised for expression in the plant, and that the nucleic acid sequence encodes a nuclear localization signal.

The present invention also embraces the methods as defined above, wherein the first and second regulatory regions are either the same or different and are selected from the group consisting of a constitutive promoter, an inducible promoter, a tissue specific promoter, and a developmental promoter.

Furthermore, this invention provides a method to regulate expression of an endogenous nucleic acid sequence of interest in a plant comprising:
   i) introducing into the plant a nucleotide sequence comprising, a regulatory region, operatively linked with a nucleotide sequence encoding a fusion protein, the fusion protein comprising,
      a) a DNA binding protein, or a portion thereof, capable of binding a segment of a DNA sequence of the endogenous nucleotide sequence of interest;
      b) a recruitment factor protein, or a portion thereof, capable of binding a chromatin remodelling protein; and
   ii) growing the plant, wherein expression of the nucleotide sequence produces the fusion protein that regulates expression of the endogenous nucleic acid sequence of interest.

The present invention also includes a method to regulate expression of an endogenous nucleic acid sequence of interest in a plant comprising:
   i) introducing into the plant a nucleotide sequence comprising a regulatory region, operatively linked with a nucleotide sequence encoding a recruitment factor protein, the recruitment factor protein capable of binding an endogenous DNA binding protein, the endogenous DNA binding protein characterized in binding a segment of a DNA sequence of the endogenous nucleotide sequence of interest, and;
   ii) growing the plant, wherein expression of the nucleotide sequence produces the recruitment factor thereby regulating expression of the endogenous nucleic acid sequence of interest.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows the nucleotide and deduced amino acid sequences of wild type ROS and a modified ROS of *Agrobacterium tumefaciens*. FIG. 1(A) shows the amino acid sequence alignment of known ROS repressors (wild-type ROS, SEQ ID NO:1; ROSR, SEQ ID NO:63; ROSAR, SEQ ID NO: 64; MucR, SEQ ID NO: 65), and a synthetic ROS (SEQ ID NO: 4). The amino acid sequence 'PKKKRKV' (SEQ ID NO: 6) at the carboxy end of synthetic ROS is one of several nuclear localization signals. FIG. 1(B) shows the nucleotide sequence of a synthetic ROS (SEQ ID NO:2) that had been optimised for plant codon usage containing a nuclear localization signal peptide (in italics). Optional restriction sites at the 5' end of the sequence are underlined. FIG. 1(C) shows the consensus nucleotide (SEQ ID NO:3) and predicted amino acid (SEQ ID NO:4) sequence, of a composite ROS sequence comprising all possible nucleotide sequences that encode wild type ROS repressor, and the wild type ROS amino acid sequence. The amino acid sequence 'PKKKRKV' (SEQ ID NO:6) at the carboxy end represents a nuclear localization signal. Amino acids in bold identify the zinc finger motif. Nucleotide codes are as follows: N=A or C or T or G; R=A or G; Y=C or T; M=A or C; K=T or G; S=C or G; W=A or T; H=A or T or C; B=T or C or G; D=A or T or G; V=A or C or G. FIG. 1(D) shows the nucleotide sequence of the operator sequences of the virC/virD (SEQ ID NO:27) and ipt (SEQ ID NO:8) genes. FIG. 1(E) shows a consensus operator sequence (SEQ ID NO:5) derived from the virC/virD (SEQ ID NOs:66-67) and ipt (SEQ ID NOs:68-69) operator sequences. This sequence comprises 10 amino acids, however, only the first 9 amino acids are required for binding ROS.

FIG. 5 shows schematic representations of nucleotide constructs that place the expression of a gene of interest under the control a regulatory region, in this case a CaMV35S regulatory region, modified to contain a ROS operator site.

FIG. 6 shows a schematic representation of a nucleotide construct that places the expression of a gene of interest gene under the control of a regulatory region, in this case, the tms2 regulatory region that has been modified to contain ROS operator sites.

FIG. 7 shows a schematic representation of a nucleotide construct that places the expression of a gene of interest under the control of a regulatory region, in this case actin 2 regulatory region, that has been modified to contain ROS operator sites.

FIG. 8 shows Southern analysis of transgenic *Arabidopsis* plants.

FIG. 9 shows expression of a gene of interest in plants. Upper panel shows expression of GUS under the control of 35S (pBI121; 35S:GUS). Middle panel shows GUS expression under the control of actin2 comprising ROS operator sequences (p74-501; see FIG. 7(B) for construct). Lower panel shows the lack of GUS activity in a non-transformed control.

FIG. 10(A) shows alignment of the deduced amino acid sequences of bnKCP1 (SEQ ID NO:71), atKCP (SEQ ID NO:72), atKCL1 (SEQ ID NO:73) and atKCL2 (SEQ ID NO:74) proteins. Serine (S)-rich residues and the conserved region (GKSKS domain) among the four sequences are single underlined and double underlined, respectively. The putative nuclear localization signal (NLS) and the phosphorylation site of protein kinase A are indicated by asterisks and diamonds, respectively.

FIG. 11(A) shows schematic representation of entire bnKCP1 protein. Numbers above or under the boxes refer to positions of amino acid residues. S-rich (34-58), GKSKS (88-143) and KID (161-215) domains or motifs are shown in dotted boxes, the nuclear localization signal (NLS) in black box, and the three acidic motifs (I, II, III) in gray boxes. FIG. 11(B) shows secondary structure features and hydrophilicity of bnKCP1 analyzed using DNAstar Protean program.

FIG. 13 shows in vitro interaction of wild type and mutant bnKCP1 proteins with the GST-HDA19 and GST-Gcn5 fusion proteins. FIG. 13(A) shows a schematic representation of the bnKCP1 and its deletion mutants obtained by deletion of C-terminal regions of bnKCP1. FIG. 13(B) shows binding activities of bnKCP1 and its mutants with GST-HDA19, GST-Gcn5 and GST alone (negative control), respectively, as indicated. The wild type bnKCP1, mutants bnKCP1$^{1-160}$ and bnKCP1$^{1-80}$, luciferase (as positive control) and negative control (no template) were produced using in vitro transcription/translation reactions. The translation products were incubated with GST fusion proteins or GST and their binding activities were examined as described in Example 4. FIG. 13(C) shows activation of lacZ reporter gene by bnKCP1 and its deletion mutants, ΔbnKCP1$^{1-160}$ and ΔbnKCP1$^{1-80}$, in yeast cells. MaV203 yeast cells carrying plasmid pDBLeu-HDA19 and the reporter gene were transfected with the plamid pPC86-bnKCP1, pPC86-bnKCP1$^{1-160}$, pPC86-bnKCP1$^{1-80}$ or pPC86 vector only. Yeast strains A and B were used as negative and positive controls, respectively. The β-galactosidase activity was assayed using chlorophenol red-β-D-galactopyranoside (CPRG) and was expressed as a percentage of activity conveyed by bnKCP1.

FIG. 16 shows expression of bnKCP1 gene in response to low temperature, LaCl$_3$ and inomycin treatments. Total RNA (20 µg/lane) was isolated from leaf blades of four-leaf stage Brassica napus cv Westar seedlings after exposure to different stress conditions and analyzed by northern blotting using the bnKCP1 ORF as probe. FIG. 16(A) shows bnKCP1 transcript accumulation in leaves and stems of seedlings exposed to cold (4° C.). FIG. 16(B) shows expression pattern of bnKCP1 gene after treatment with LaCl$_3$ and inomycin.

FIG. 17 shows transactivation, of the lacZ gene by bnKCP1 in yeast. The lacZ gene was driven by a promoter containing GAL4 DNA binding sites and integrated into the genome of yeast MaV203. FIG. 17(A) is a schematic representation of the bnKCP1 and its deletion mutants. FIG. 17(B) Yeast cells carrying the reporter gene were transfected with the effector plasmids pDBLeu-bnKCP1, pDBLeu-bnKCP1$^{1-160}$, pDBLeu-bnKCP1$^{1-80}$, and pDBLeu-bnKCP1$^{81-215}$ or the pDBLeu vector only. Yeast strains A and B (GibcoL BRL, Life Technologies) were used as negative and positive controls, respectively. The β-galactosidase activity was assayed using CPRG (chlorophenol red-β-D-galactopyranoside) and was expressed as a percentage of activity conveyed by the positive control (strain C). Bars indicate the standard error of three replicates.

FIG. 18 shows the nuclear localization of GUS-bnKCP1 protein in onion cells. FIG. 18(A) is a schematic diagram of the GUS-bnKCP1 fusion construct containing the CaMV 35S promoter. The bnKCP1 was fused in-frame to the GUS reporter gene. FIG. 18(B) shows transient expression of GUS-bnKCP1 fusion protein (top) and GUS alone (bottom) in onion cells. Onion tissues were simultaneously analysed using histochemical GUS assay (left) and nucleus-specific staining with DAPI (right) as described in Example 4.

FIG. 20 shows alignment of the deduced products of BnSCL1 (SEQ ID NO:81), AtSCL15 (accession number Z99708) (SEQ ID NO:82) and LsSCL (accession number AF273333) (SEQ. ID NO:83). Identical and conserved amino acids in the three proteins are shown as white letters on a black background and black letter on a gray background, respectively. Amino acids with weak similarity are indicated as white letters on a gray background. Amino acids with no similarity are shown as black letters on a white background. The putative nuclear localization signals and LXXLL motif are indicated by asterisks and dots, respectively. The VHIID motif, two leucine heptad regions (LHRI and LHRII), PFYRE and SAW motif are underlined as indicated.

FIG. 23 shows in vitro interaction of wild type and mutant BnSCL1 proteins with the GST-HDA19 fusion protein. FIG. 23(A) is a schematic representation of the BnSCL1 and its deletion mutants obtained by the deletion of its C-terminal regions. FIG. 23(B) shows the binding activities of BnSCL1 and its mutants with GST-HDA19. The wild type BnSCL1, mutants $\Delta BnSCL1^{1-358}$, $\Delta BnSCL1^{1-261}$, $\Delta BnSCL1^{1-217}$ and $\Delta BnSCL1^{1-145}$, luciferase (positive control) and negative control (no template) were produced using in vitro transcription/translation reactions. The translation products were incubated with GST fusion proteins or GST alone (data not shown) and their binding activities were examined as described in Example 5. Arrow point to band representing the in vitro translated $\Delta BnSCL1^{1-145}$ protein that did not bind to the recombinant protein.

FIG. 24 shows in vivo interaction of wild type and mutant BnSCL1 proteins. FIG. 24(A) is a schematic representation of the BnSCL1 and its deletion mutants. FIG. 24(B) shows the activation of lacZ reporter gene by BnSCL1 and its deletion mutants in yeast cells. MaV203 yeast cells carrying plasmid pDBLeu-HDA19 and the lacZ reporter gene were transfected with the plasmid pPC86-BnSCL1, pPC86-BnSCL1$^{1-358}$, pPC86-BnSCL1$^{1-261}$, pPC86-BnSCL1$^{1-217}$, pPC86-BnSCL1$^{1-145}$, pPC86-BnSCL1$^{146-358}$, pPC86-BnSCL1$^{218-438}$ or pPC86 vector only. The negative control yeast strain A, and the positive controls yeast strains B and C (GIBCOL BRL, Life Technologies) were also used. The β-Galactosidase activity was assayed using CPRG (chlorophenol red-β-D-galactopyranoside) and was expressed as a percentage of activity conveyed by yeast strain C. Bars indicate the standard error of three replicates.

FIG. 25 shows transactivation of the lacZ gene by BnSCL1 protein in yeast. FIG. 25(A) is a schematic representation of the BnSCL1 and its deletion mutants. FIG. 25(B) shows the activation of lacZ reporter gene by BnSCL1 and its deletion mutants in yeast cells. The lacZ reporter gene was driven by a promoter containing GAL4 DNA binding sites and integrated into the genome of yeast MaV203 cell. Yeast cells carrying the reporter gene were transfected with the effector plasmids pDBLeu-BnSCL1, pDBLeu-BnSCL1$^{1-358}$, pDBLeu-BnSCL1$^{1-261}$, pDBLeu-BnSCL1$^{1-217}$, pDBLeu-BnSCL1$^{1-145}$, pDBLeu-BnSCL1$^{146-358}$, pDBLeu-BnSCL1$^{218-438}$ or pDBLeu vector only. Yeast strains A, B, C and D (GIBCOL BRL, Life Technologies) were used as controls as described in Example 5. The β-Galactosidase activity was assayed using CPRG and was expressed as a percentage of activity conveyed by the wild type BnSCL1 protein. Bars indicate the standard error of three replicates.

FIG. 26 shows expression patterns of BnSCL1 mRNA in different tissues. FIG. 26(A) is a RNA gel blot analysis of total RNA (20 μg/lane) isolated from leaves, flowers, roots, stems and siliques, electrophoresed through a 1.2% agarose gel containing formaldehyde and probed with the ORF of BnSCL1 as described in Example 5. EtBr stained total RNA is shown to indicate even loading. FIG. 26(B) is a quantitative one-step RT-PCR analysis of total RNA extracted from leaves, flowers, roots, stems, siliques and shoots. Quantitative RT-PCR products were electrophoresed through a 1% agarose gel and hybridized with $^{32}$P-labelled 5'-end fragment (435 bp) of BnSCL1 ORF. A 960 bp fragment of the *Brassica napus* actin gene co-amplified with BnSCL1 was used as an internal standard as described in Example 5.

FIG. 28 shows kinetics of BnSCL1 mRNA accumulation in response to auxin in the presence and absence of histone deacetylase inhibitor sodium butyrate. Nine-day-old light-grown seedlings were treated with 10 mM sodium butyrate for 24 h followed by exogenous 2,4-D application at variable concentrations as indicated. Quantitative one-step RT-PCR was used to analyze total RNA extracted from shoots (FIG. 28A) and roots (FIG. 28B) (see legend to FIG. 27 Expression of BnSCL1 in response to 2,4-D was also analyzed using quantitative RT-PCR of total RNA isolated from shoots and roots of 10 dpg seedlings in the presence of 50 μM NPA, an auxin transport inhibitor, for 24 h before the exogenous application of 2,4-D (FIG. 28C).

FIG. 29 shows in a diagrammatic form several constructs that may be used to regulate gene expression as described in Example 6.

DESCRIPTION OF PREFERRED EMBODIMENT

Figure 2A:
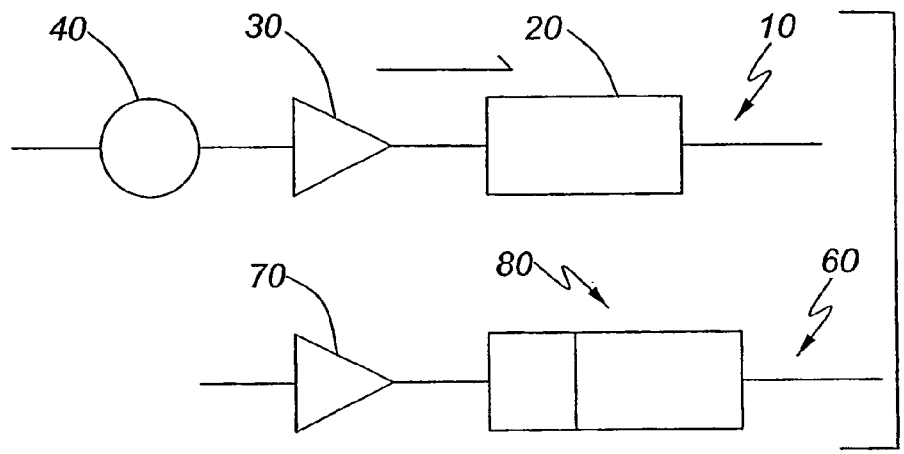
FIG. 2-4 shows in a diagrammatic form several variations of regulating gene expression using the methods of the present invention.

The present invention relates to the regulation of gene expression. More particularly, the present invention relates to the control of gene expression of one or more nucleotide sequences of interest in transgenic plants using chromatin remodelling factors.

The following description is of a preferred embodiment by way of example only and without limitation to the combination of features necessary for carrying the invention into effect.

Gene regulation can be used in applications such as metabolic engineering to produce plants that accumulate large amounts of certain intermediate compounds. Regulation of gene expression can also be used for control of transgenes across generations, or production of F1 hybrid plants with seed characteristics that would be undesirable in the parental line, for example but not limited to, hyper-high oil, reduced fiber content, low glucosinolate levels, reduced levels of phytotoxins, and the like. In the latter examples, low glucosinolate levels, or other phytotoxins, may be desired in seeds while higher concentrations of these compounds may be required elsewhere, for example in the case of glucosinolates, within cotyledons, due to their role in plant defence. Another non-limiting example for the controlled regulation of a gene of interest during plant development is seed specific down regulation of sinapine biosynthesis, as for example in seeds of *Brassica napus*. In many instances, transgene expression needs to be regulated only in certain plant organs/tissues or at certain stages of development. The methods as described herein may also be used to control the expression of a gene of interest that encodes a protein used to for plant selection purposes. For example, which is to be considered non-limiting, a gene of interest may encode a protein that is capable of metabolizing a compound from a non-toxic form to a toxic form thereby selectively removing plants that express the gene of interest.

The present invention provides a method to regulate the expression of a gene of interest by transforming a plant with one or more constructs comprising:

1) a first nucleotide sequence comprising,
   a) a nucleic acid sequence of interest operatively linked to a regulatory region, b) an operator sequence capable of binding a fusion protein, and;
2) a second nucleotide sequence comprising a regulatory region in operative association with a nucleotide sequence encoding a fusion protein, the fusion protein comprising,
a) a DNA binding protein, or a portion of a DNA binding protein capable of binding the operator sequence, and;
b) a recruitment factor protein, or a portion of a recruitment factor protein capable of binding a chromatin remodelling protein, wherein binding of the fusion protein to the operator sequence of the first nucleotide sequence regulates expression of the nucleic acid sequence of interest from the first nucleotide sequence. The operator sequence of the first nucleotide sequence may be positioned upstream of the ORF of the nucleic acid sequence of interest.

These first and second nucleotide sequences may be placed within the same or within different vectors, genetic constructs, or nucleic acid molecules. Preferably, the first nucleotide sequence and the second nucleotide sequence are chromosomally integrated into a plant or plant cell. The two nucleotide sequences may be integrated into two different genetic loci of a plant or plant cell, or the two nucleotide sequences may be integrated into a singular genetic locus of a plant or plant cell. However, the second nucleotide sequence may be integrated into the DNA of the plant or it may be present as an extra-chromosomal element, for example, but not wishing to be limiting a plasmid.

By "operatively linked" it is meant that the particular sequences interact either directly or indirectly to carry out their intended function, such as mediation or modulation of gene expression. The interaction of operatively linked sequences may, for example, be mediated by proteins that in turn interact with the sequences. A transcriptional regulatory region and a sequence of interest are "operably linked" when the sequences are functionally connected so as to permit transcription of the sequence of interest to be mediated or modulated by the transcriptional regulatory region.

By the term "regulate the expression" it is meant reducing or increasing the level of mRNA, protein, or both mRNA and protein, encoded by a gene or nucleotide sequence of interest in the presence of the fusion protein encoded by the second nucleotide sequence, relative to the level of mRNA, protein or both mRNA and protein encoded by the nucleic acid sequence of interest in the absence of the fusion protein encoded by the second nucleotide sequence.

By the term "fusion protein" it is meant a protein comprising two or more amino acid portions which are not normally found together within the same protein in nature and that are encoded by a single gene. Fusion proteins may be prepared by standard techniques in molecular biology known to those skilled in the art (see for example FIG. 17). In the context of the present invention, at least one of the amino acid portions is capable of binding an operator sequence as defined herein.

By the term "binding" it is meant reversible or non-reversible association of two components, for example the operator sequence and the DNA binding domain of a protein, including a fusion protein, or the recruitment factor protein and chromatin remodelling protein as described herein. Preferably, the two components have a tendency to remain associated, but are capable of dissociation under appropriate conditions. Conditions may include, but are not limited to, the addition of a third component, chemical, etc which enhances dissociation of the bound components.

By the term "recruitment factor" it is meant a protein or peptide sequence capable of interacting with, or binding a chromatin remodelling protein. Preferably, the recruitment factor and the chromatin remodelling protein interact or bind in a manner such that the activity of the chromatin remodelling protein is retained. However, by binding the recruitment factor, the activity of the chromatin remodelling protein may be modified in some manner. Non-limiting examples of recruitment factors include KID, for example bnKCP1, or fragments thereof (Example 4), BnSCL1, or fragments therof (Example 5), ADA, SAGA, STAGA, PCAF, TFIID, and TFIIIC (Lusser, 2001, Table 1, which is incorporated herein by reference). A recruitment factor may be modified to include a DNA binding region, for example as outlined in FIG. 17, [or a native recruitment factor may be utilized to target proteins that interact with genes in their native context]. An example, which is not to be considered limiting in any manner, bnKCP1, or active fragments thereof (see Example 4) can target transcription factors that are known to bind DNA. Examples of such transcription factors include ERF (Hart et al., 1993), SEBF (Boyle and Brisson, 2001), or CBF (Stockinger et al., 1997). In this manner by over expressing bnKCP1, regulation of the expression of a gene that is dependant on ERF, CBP or SEBF activity may be regulated. Another non-limiting example of a recruitment factor is BnSCL1, or active fragments thereof (see Example 5). An example, which is not to be considered limiting, of a protein that interacts with bnKCP1 and BnSCL1 is the chromatin remodelling protein HDAC, for example HDA19.

By the term "chromatin remodelling protein" it is meant a protein that is capable of altering the structure of chromatin. Preferably the chromatin remodelling protein is histone acetyl transferase (HAT) or histone deacetylase (referred to either as HD, HDA, or HDAC). Any HAT protein, HDAC protein, or any derivative of any HAT protein or HDAC protein may be used in the method of the present invention provided that the HAT protein, HDAC protein or derivative thereof exhibits the respective histone acetylase, or histone deacetylase activity in plants.

By the term "HD binding domain" or "histone deacetylase binding domain", it is meant a sequence of amino acid residues which interacts with a histone deacetylase enzyme through protein-protein interactions. Such protein-protein interactions can be monitored in several ways, for example, which is not to be considered limiting, by yeast two-hybrid experiments. Non-limiting examples of proteins comprising a HD binding domain include bnKCP1 and BnSCL1.

By the term "DNA binding protein or portion of a DNA binding protein" it is meant a protein or amino acid sequence capable of binding to a specific operator sequence. By "operator sequence" it is meant a sequence of DNA that is capable of binding to the DNA binding protein or portion of the DNA binding protein. Examples of a DNA binding proteins capable of binding specific operator sequences include, but are not limited to, the ROS repressor, TET repressor, Sin3, VP16, GAL4, LexA, UMe6, ERF, SEBF and CBF. Any DNA binding protein or portion of any DNA binding protein may be employed in the method of the present invention provided that the protein or portion thereof is capable of binding to an operator sequence. As an example, but not to be considered limiting in any manner, the ROS repressor may be employed in the method of the present invention. By ROS repressor it is meant any ROS repressor, analog or derivative thereof as known within the art which is capable of binding to an operator sequence. These include ROS repressors as described herein, as well as other microbial ROS repressors, for example but not limited to ROSAR (*Agrobacterium radio-*

*bacter*; Brightwell et al., 1995) (SEQ ID NO:64), MucR (*Rhizobium meliloti*; Keller M et al., 1995) (SEQ ID NO:65), and ROSR (*Rhizobium elti*; Bittinger et al., 1997; also see Cooley et al., 1991; Chou et al., 1998; Archdeacon J et al., 2000; D'Souza-Ault M. R., 1993; all of which are incorporated herein by reference) (SEQ ID NO:63). The DNA sequence of ROS, or any other DNA binding protein, may be modified to optimize expression within a plant. Examples of ROS repressors that may be used as described herein are provided in FIGS. 1(A) to (C) and (SEQ ID NOs: 1-4).

The DNA binding protein, or portion thereof that exhibits DNA binding activity may be fused to a recruitment factor or chromatin remodelling protein as described herein. Examples of such fusion proteins can be prepared, using methods known in the art, for example but not limited to the method outlined in FIG. 17. FIG. 17 discloses a strategy for creating fusion between the zinc finger domain of the ROS repressor and the KID domain of bnKCP1. This involves amplification of regions encoding the zinc finger domain of the ROS repressor and the KID domain using the following primers:

zinc finger: The forward primer (zf-F) contains a restriction enzyme site at the 5' end and the reverse primer (zf-R) contains 15 nucleotides from the 5' end of the KID region.;

KID domain: The forward primer (KID-F) contains 15 nucleotides from the 3' region of the zinc finger domain, and the reverse primer (KID-R) contains a restriction enzyme site at the 3' end.

The amplified zinc finger and KID fragments are combined and used as a template for a new round of PCR amplification where only the forward primer (zf-F) of the zinc finger and the reverse primer (KID-R) of the KID domain are used. The two separate templates are amplified to create one single in frame fusion fragment encoding the zinc finger and KID domains, and containing restriction sites at each end. This product is then cloned into a plant expression vector.

However, it is to be understood that fusion of a recruitment factor with a DNA binding protein may not be required in order to regulate expression of a nucleic acid sequence of interest. Recruitment factors are known to bind chromatin remodelling proteins and factors that directly or indirectly bind DNA. For example, bnKCP1 (Example 4) exhibits the property of binding ERF.

Depending upon the chromatin remodelling protein selected, gene expression may be up-regulated or down-regulated. For example, which is not to be considered limiting in any manner, the binding of a fusion protein containing a recruitment factor capable of recruiting HAT to a gene, may result in up-regulation of expression of a nucleic acid sequence of interest, while a fusion protein that recruits HDAC will result in the down-regulation of the expression of a nucleic acid sequence of interest. However, it is within the scope of the present invention that modification to the rate of up-regulation and down-regulation of gene expression may occur depending upon the location of the operator sequence that binds the fusion protein.

The operator sequence is preferably located in proximity to the nucleic acid sequence of interest, either upstream of or downstream of the nucleic acid sequence of interest (see for example FIG. 5A-D). Alternatively, the operator sequence may be within the non-coding region of the nucleic acid sequence of interest, for example, but not wishing to be limiting, within an intron of the gene. If it is desired to have the expression of a nucleic acid sequence of interest reduced or repressed, the operator sequence may be located within a nucleotide region that interferes with binding of transcription factors required for transcription of the nucleic acid sequence of interest, for example, interfering with the binding of the RNA polymerase to the nucleic acid sequence of interest, or reducing the rate of migration of the polymerase along a nucleotide sequence, or both.

An operator sequence may consist of a minimal sequence required for binding of a DNA binding protein or fragment thereof, or it may comprise an inverted repeat or palindromic sequences of a specified length. For example, but not wishing to be limiting, the ROS operator sequence may comprise 9 or more nucleotide base pairs (see FIGS. 1(D) and (E)) that exhibits the property of binding a DNA binding domain of a ROS repressor. A consensus sequence of a 10 amino acid region including the 9 amino acid DNA binding site sequence is WATDHWKMAR (SEQ ID NO: 5; FIG. 1(E)). The last amino acid, "R", of the consensus sequence is not required for ROS binding (data not presented). Examples of operator sequences, which are not to be considered limiting in any manner, also include, as is the case with the ROS operator sequence from the virC or virD gene promoters, a ROS operator made up of two 11 bp inverted repeats separated by TTTA:

```
TATATTTCAATTTTATTGTAATATA;      (SEQ ID NO: 7)
or
``` the operator sequence of the IPT gene:

```
TATAATTAAAATATTAACTGTCGCATT.    (SEQ ID NO: 8)
```

However, it is to be understood that analogs or variants of SEQ ID NO's:7, 8 and 5 may also be used providing they exhibit the property of binding a DNA binding domain, preferably a DNA binding domain of the ROS repressor. For example, but not to be considered limiting in any manner, in the promoter of the divergent virC/virD genes of *Agrobacterium tumefaciens*, ROS binds to a 9 bp inverted repeat sequence in an orientation-independent manner (Chou et al., 1998). The ROS operator sequence in the ipt promoter also consists of a similar sequence to that in the virC/virD except that it does not form an inverted repeat (Chou et al., 1998). Only the first 9 bp are homologous to ROS box in virC/virD indicating that the second 9 bp sequence may not be a requisite for ROS binding. Accordingly, the use of ROS operator sequences or variants thereof that retain the ability to interact with ROS, as operator sequences to selectively control the expression of genes or nucleotide sequences of interest, is within the scope of the present invention.

Other operator sequences include sequences known to bind transcription factors, for example but not limited to:
  TAAGAGCCGCC (SEQ ID NO:9), which is known to bind ERF (in ethylene responsive genes; Hart et al., 1993);
  GACTGTCAC (SEQ ID NO:10), which is known to bind to SEBF (in pathogenesis responsive genes; Boyle and Brisson, 2001);
  TACCGACAT (SEQ ID NO:11) and TGGCCGAC (SEQ ID NO:12), which are known to bind CBF (in low temperature responsive genes; Stockinger et al., 1997).

The transcription factors ERF, SEBF and CBF are example of factors that can be targeted by the recruitment factor bnKCP1.

By "regulatory region" or "regulatory element" it is meant a portion of nucleic acid typically, but not always, upstream of the protein coding region of a gene, which may be comprised of either DNA or RNA, or both DNA and RNA. When a regulatory region is active and in operative association with a nucleic acid sequence of interest, this may result in expression of the nucleic acid sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well.

An inducible regulatory region is one that is capable of directly or indirectly activating transcription of one or more DNA sequences or genes in response to an inducer. In the absence of an inducer the DNA sequences or genes will not be transcribed. Typically the protein factor, which binds specifically to an inducible regulatory region to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998; which is incorporated by reference). Examples, of potential inducible promoters include, but not limited to, teracycline-inducible promoter (Gatz, C., 1997; which is incorporated by reference), steroid inducible promoter (Aoyama, T. and Chua, N. H., 1997; which is incorporated by reference) and ethanol-inducible promoter (Salter, M. G., et al, 1998; Caddick, M. X. et al,1998; which are incorporated by reference) cytokinin inducible IB6 and CKI1 genes (Brandstatter, I. and Kieber, J. J., 1998; Kakimoto, T., 1996; which are incorporated by reference) and the auxin inducible element, DR5 (Ulmasov, T., et al., 1997; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985), the rice actin 1 (Zhang et al, 1991), actin 2 (An et al., 1996), or tms 2 (U.S. Pat. No. 5,428,147, which is incorporated herein by reference), and triosephosphate isomerase 1 (Xu et. al., 1994) genes, the maize ubiquitin 1 gene (Comejo et al, 1993), the *Arabidopsis ubiquitin* 1 and 6 genes (Holtorf et al, 1995), and the tobacco translational initiation factor 4A gene (Mandel et al, 1995). The term "constitutive" as used herein does not necessarily indicate that a gene under control of the constitutive regulatory region is expressed at the same level in all cell types, but that the gene is expressed in a wide range of cell types even though variation in abundance is often observed.

The regulatory regions of the first and second nucleotide sequences denoted above, may be the same or different. For example, which is not to be considered limiting in any manner, the regulatory elements of the first and second genetic constructs may both be constitutive. In an aspect of an embodiment, the first and second nucleotide sequences may be maintained in the same plant. In an alternate embodiment the first and second nucleotide sequences are maintained in separate plants, a first and a second plant, respectively. The first nucleotide sequence encoding a nucleic acid sequence of interest is expressed within the first plant. In the second embodiment, the second plant expresses the second nucleic acid sequence encoding the fusion protein capable of regulating the expression of the nucleic acid sequence of interest within the first plant. Crossing of the first and second plants produces a progeny that expresses the fusion protein which regulates the expression of the nucleic acid sequence of interest. In this manner the expression of nucleic acid sequence of interest that is required to maintain parent stocks may be retained within a parent plant but not expressed in a progeny plant. Such a cross may produce sterile offspring.

Alternatively, which is not to be considered limiting in any manner, the second regulatory element may be active before, during, or after the first regulatory element is active. Similarly, the first regulatory element may be active before, during, or after the second regulatory element is active. Other examples, which are not to be considered limiting, include the second regulatory element being an inducible regulatory element that is activated by an external stimulus so that regulation of gene expression may be controlled through the addition of an inducer. The second regulatory element may also be active during a specific developmental stage preceding, during, or following that of the activity of the first regulatory element. In this way the expression of the nucleic acid sequence of interest may be repressed or activated as desired within a plant.

By "nucleic acid sequence of interest", "nucleotide sequence of interest" or "coding region of interest" it is meant any gene or nucleotide sequence that is to be expressed within a host organism. Such a nucleotide sequence of interest may include, but is not limited to, a gene whose product has an effect on plant growth or yield, for example a plant growth regulator such as an auxin or cytokinin and their analogues, or a nucleotide sequence of interest may comprise a herbicide or a pesticide resistance gene, which are well known within the art. A nucleic acid sequence of interest or a coding region of interest, may encode an enzyme involved in the synthesis of, or in the regulation of the synthesis of, a product of interest, for example, but not limited to a protein, or an oil product. A nucleotide sequence of interest or a coding region of interest, may encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis, etc.

A nucleotide sequence of interest or a coding region of interest, may also encode a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-$\alpha$, interferon-$\beta$, interferon-$\gamma$, blood clotting factors, for example, Factor VIII, Factor IX, or tPA or combinations thereof. If the nucleic acid sequence of interest or a coding region of interest, encodes a product that is directly or indirectly toxic to the plant, then by using the method of the present invention, such toxicity may be reduced throughout the plant by selectively expressing the nucleic acid sequence of interest within a desired tissue or at a desired stage of plant development.

A nucleotide sequence of interest or a coding region of interest, may also include a gene that encodes a protein involved in regulation of transcription, for example DNA-binding proteins that act as enhancers or basal transcription factors. Moreover, a nucleotide sequence of interest may be comprised of a partial sequence or a chimeric sequence of any of the above genes, in a sense or antisense orientation.

It is also contemplated that a nucleic acid sequence of interest or a coding region of interest, may be involved in the expression of a gene expression cascade, for example but not limited to a developmental cascade. In this embodiment, the nucleic acid sequence of interest is preferably associated with a gene that is involved at an early stage within the gene cascade, for example homeotic genes. Expression of a nucleic acid sequence of interest, for example a repressor of homeotic gene expression, represses the expression of a homeotic gene. Expression of the fusion protein that represses gene expression within the same plant, either via crossing, induction, temporal or developmental expression of the regulatory region, as described herein, de-represses the expression of the homeotic gene thereby initiating a gene cascade. Conversely, using the methods described herein, expression of an introduced (i.e. transgenic) homeotic gene may be activated in a selective manner, so that it is expressed outside of its normal developmental or temporal expression pattern, thereby initiating a cascade of developmental events. This may be achieved by targeting a chromatin remodelling protein to a desired homeotic gene as described herein.

Homeotic genes are well known to one of skill in the art, and include but are not limited to, transcription factor proteins and associated regulatory regions, for example controlling sequences that bind AP2 domain containing transcription factors, for example but not limited to, APETALA2 (a regulator of meristem identity, floral organ specification, seedcoat development and floral homeotic gene expression; Jofuku et al., 1994), CCAAT box-binding transcription factors (e.g. LEC1; WO 98/37184; Lotan, T. et al., 1998), or the controlling factor associated with PICKLE, a gene that produces a thickened, primary root meristem (Ogas, J. et al.,1997).

A nucleic acid sequence of interest or a coding region of interest, may also be involved in the control of transgenes across generations, or production of F1 hybrid plants with seed characteristics that would be undesirable in the parental line or progeny, for example but not limited to, oil seeds characterized as having reduced levels of sinapine biosynthesis within the oil-free meal. In this case, a nucleic acid sequence of interest may be any enzyme involved in the synthesis of one or more intermediates in sinipine biosynthesis. An example, which is to be considered non-limiting, is caffeic o-methyltransferase (Acc# AAG51676), which is involved in ferulic acid biosynthesis. Other examples of genes of interest include genes that encode proteins involved in fiber, or glucosinolate, biosynthesis, or a protein involved in the biosynthesis of a phytotoxin. Phytotoxins may also be used for plant selection purposes. In this non-limiting example, a nucleic acid sequence of interest may encode a protein that is capable of metabolizing a compound from a non-toxic form to a toxic form thereby selectively removing plants that express the nucleic acid sequence of interest. The phytotoxic compound may be synthesized from endogenous precursors that are metabolized by the nucleic acid sequence of interest into a toxic form, for example plant growth regulators, or the phytotoxic compound may be synthesized from an exogenously applied compound that is only metabolized into a toxic compound in the presence of the nucleic acid sequence of interest. For example, which is not to be considered limiting, the nucleic acid sequence of interest may comprise indole acetamide hydrolase (IAH), that converts exogenously applied indole acetamide (IAM) or naphthaline acetemide (NAM), to indole acetic acid (IAA), or naphthaline acetic acid (NAA), respectively. Over-synthesis of TAA or NAA is toxic to a plant, however, in the absence of TAH, the applied IAM or NAM is non-toxic. Similarly, the nucleic acid sequence of interest may encode a protein involved in herbicide resistance, for example, but not limited to, phosphinothricin acetyl transferase, wherein, in the absence of the gene encoding the transferase, application of phosphinothricin, the toxic compound (herbicide) results in plant death. Other nucleic acid sequence of interest that encode lethal or conditionally lethal products may be found in WO 00/37660 (which is incorporated herein by reference).

The nucleic acid sequence of interest, the nucleotide sequence of interest or a coding region of interest, may be expressed in suitable eukaryotic hosts which are transformed by the nucleotide sequences, or nucleic acid molecules, or genetic constructs, or vectors of the present invention. Examples of suitable hosts include, but are not limited to, insect hosts, mammalian hosts, yeasts and plants. Suitable plant hosts include, but are not limited to agricultural crops including canola, *Brassica* spp., maize, tobacco, alfalfa, rice, soybean, wheat, barley, sunflower, and cotton.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5'-AATAAA-3' although variations are not uncommon. One or more of the chimeric genetic constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene.

To aid in identification of transformed plant cells, the constructs of this invention may be further manipulated to include selectable markers. Useful selectable markers in plants include enzymes which provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (β-glucuronidase), or luminescence, such as luciferase or GFP, are useful.

Also considered part of this invention are transgenic eukaryotes, for example but not limited to plants containing the chimeric gene construct of the present invention. However, it is to be understood that the chimeric gene constructs of the present invention may also be combined with nucleic acid sequence of interest for expression within a range of eukaryotic hosts.

In instances where the eukaryotic host is a plant, methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures (for example, Clough and Bent, 1998).

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, 1988; Geierson and Corey, 1988; and Miki and Iyer, 1997; Clough and Bent, 1998). The present invention further includes a suitable vector comprising the chimeric gene construct.

The DNA binding protein which is employed in the method of the present invention may be naturally produced in an organism other than a plant. For example, but not wishing to be considered limiting, a ROS repressor is encoded by a nucleotide sequence of bacterial origin and, as such the nucleotide sequence may be optimised, for example, by changing its codons to favour plant codon usage, by attaching a nucleotide sequence encoding a nuclear localisation signal (NLS), for example but not limited to SV40 localization signal (see Robbins et al., 1991; Rizzo, P., et al., 1991; which are incorporated herein by reference) in order to improve the efficiency of ROS transport to the plant nucleus to facilitate the interaction with its respective operator, or both optimizing plant codon usage. Addition of an NLS to a fusion protein comprising a binding domain, for example the ROS repressor binding domain, and a recruitment factor, may also ensure targeting of the fusion product to the nuclear compartment. Similar optimization may be performed for other DNA binding proteins of non-plant source, however, such optimization may not always be required. Other possible nuclear localization signals that may be fused to a DNA binding protein include but are not limited to those listed in Table 1:

TABLE 1 nuclear localization signals

| Nuclear Protein | Organism | NLS | Ref |
|---|---|---|---|
| AGAMOUS | A | RienttnrqvtfcKRR (SEQ ID NO:13) | 1 |
| TGA-1A | T | RRlaqnreaaRKsRlRKK (SEQ ID NO:14) | 2 |
| TGA-1B | T | KKRaRlvrnresaqlsRqRKK (SEQ ID NO:15) | 2 |
| O2 NLS B | M | RKRKesnresaRRsRyRK (SEQ ID NO:16) | 3 |
| NIa | V | KKnqkhklkm-32aa-KRK (SEQ ID NO:17) | 4 |
| Nucleoplasmin | X | KRpaatkkagqaKKKKl (SEQ ID NO:18) | 5 |
| NO38 | X | KRiapdsaskvpRKKtR (SEQ ID NO:19) | 5 |
| N1/N2 | X | KRKteeesplKdKdaKK (SEQ ID NO:20) | 5 |
| Glucocorticoid receptor | M,R | RkclqagmnleaRKtKK (SEQ ID NO:21) | 5 |
| α receptor | H | RKclqagmnleaRKtKK (SEQ ID NO:22) | 5 |
| β receptor | H | RKclqagmnleaRKtKK (SEQ ID NO:23) | 5 |
| Progesterone receptor | C,H,Ra | RKccqagmvlggRKfKK (SEQ ID NO:24) | 5 |

TABLE 1-continued nuclear localization signals

| Nuclear Protein | Organism | NLS | Ref |
|---|---|---|---|
| Androgen receptor | H | RKcyeagmtlgaRKlKK (SEQ ID NO:25) | 5 |
| p53 | C | RRcfevrvcacpgRdRK (SEQ ID NO:26) | 5 |

+A, Arabidopsis; X, Xenopus; M, mouse; R, rat; Ra, rabbit; H, human; C, chicken; T, tobacco; M, maize; V, potyvirus.
References:
1. Yanovsky et al., 1990
2. van der Krol and Chua, 1991
3. Varagona et al., 1992
4. Carrington et al., 1991
5. Robbins et al., 1991

Incorporation of a nuclear localization signal into the fusion protein of the present invention may facilitate migration of the fusion protein, into the nucleus. Without wishing to be bound by theory, reduced levels of fusion proteins elsewhere within the cell may be important when the DNA binding portion of the fusion protein may bind analogue operator sequences within other organelles, for example within the mitochondrion or chloroplast. Furthermore, the use of a nuclear localization signal may permit the use of a less active promoter or regulatory region to drive the expression of the fusion protein while ensuring that the concentration of the expressed protein remains at a desired level within the nucleus, and that the concentration of the protein is reduced elsewhere in the cell.

Figure 2B:
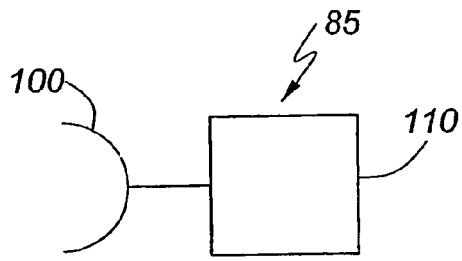
Figure 2C:
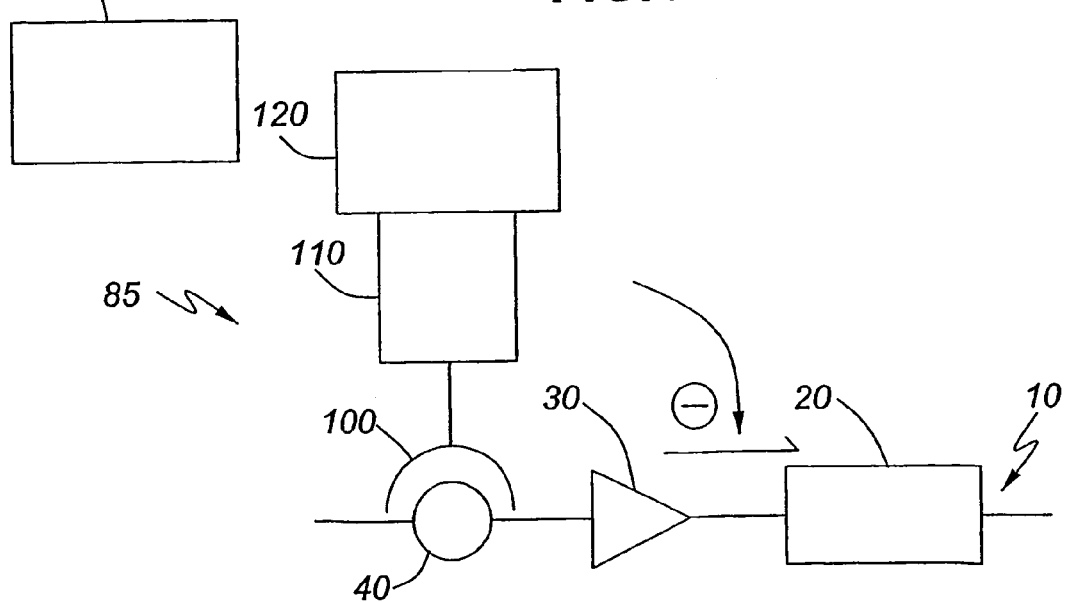

Referring now to FIGS. 2A-C, there is shown aspects of an embodiment of the method of the present invention. Shown in FIG. 2A are two constructs which have been introduced within a plant cell. The constructs comprise:
1) a first nucleotide sequence (10) comprising,
   a) a nucleic acid sequence of interest (20) operatively linked to a first regulatory region (30);
   b) an operator sequence (40) capable of binding a fusion protein (85, FIG. 2B), and;
2) a second nucleotide sequence (60) comprising a second regulatory region (70) in operative association with a nucleotide sequence (80) encoding a fusion protein (85).

The fusion protein (FIG. 2B; 85) encoded by nucleotide sequence (80) comprises
   a) a DNA binding protein (100), or a portion of a DNA binding protein capable of binding the operator sequence (40, FIG. 2A), and;
   b) a recruitment factor protein (110), or a portion of a recruitment factor protein capable of binding a chromatin remodelling protein (120), for example but not limited to histone deacetylase, HDAC.

In the example shown in FIG. 2A-C, the operator sequence (40) is shown as being upstream from the regulatory region (30), however, the operator sequence may also be positioned downstream from the regulatory region (40), for example between the regulatory region (40) and the nucleic acid sequence of interest (20; see for example the constructs in FIG. 5A-D), within the coding region of the nucleic acid sequence of interest (20), or downstream of the nucleic acid sequence of interest (20).

Referring now to FIG. 2C, but without wishing to be bound by theory, transcription and translation of nucleotide sequence (60; FIG. 2A) produces fusion protein (80; FIG. 2B) which is capable of binding operator sequence (40; FIG. 2A) and for example, histone deacetylase (120). Dual binding of histone deacetylase (120) to fusion protein (85) and fusion protein (85) to operator sequence (40) facilitates enzymatic deacetylation of histones (via bound histone deacetylase) in proximity of the nucleic acid sequence of interest (20) thereby causing repression of the nucleic acid sequence of interest (20).

The first (10) and second (60) nucleotide sequences may be placed within the same or within different vectors, genetic constructs, or nucleic acid molecules. Preferably, the first nucleotide sequence and the second nucleotide sequence are chromosomally integrated into a plant or plant cell. The two nucleotide sequences may be integrated into two different genetic loci of a plant or plant cell, or the two nucleotide sequences may be integrated into a singular genetic locus of a plant or plant cell. However, the second nucleotide sequence may be integrated into the DNA of the plant or it may be present as an extra-chromosomal element, for example, but not wishing to be limiting a plasmid. Furthermore, the first and second regulatory regions may be the same or different, and maybe active in a constitutive, temporal, developmental or inducible manner.

Figure 3A:
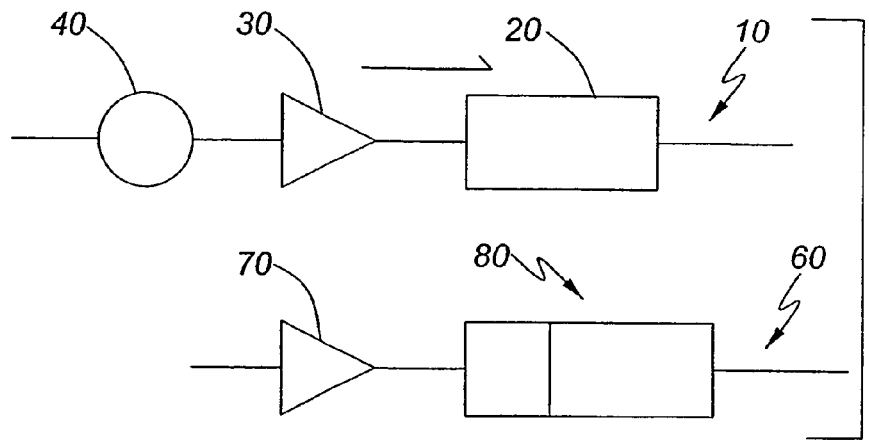
Figure 3B:
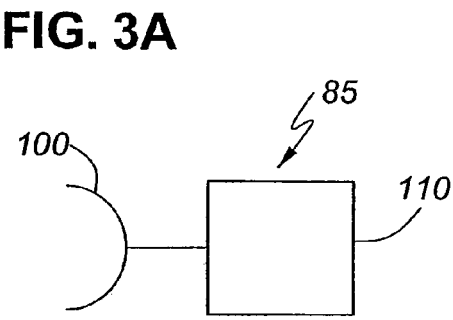
Figure 3C:
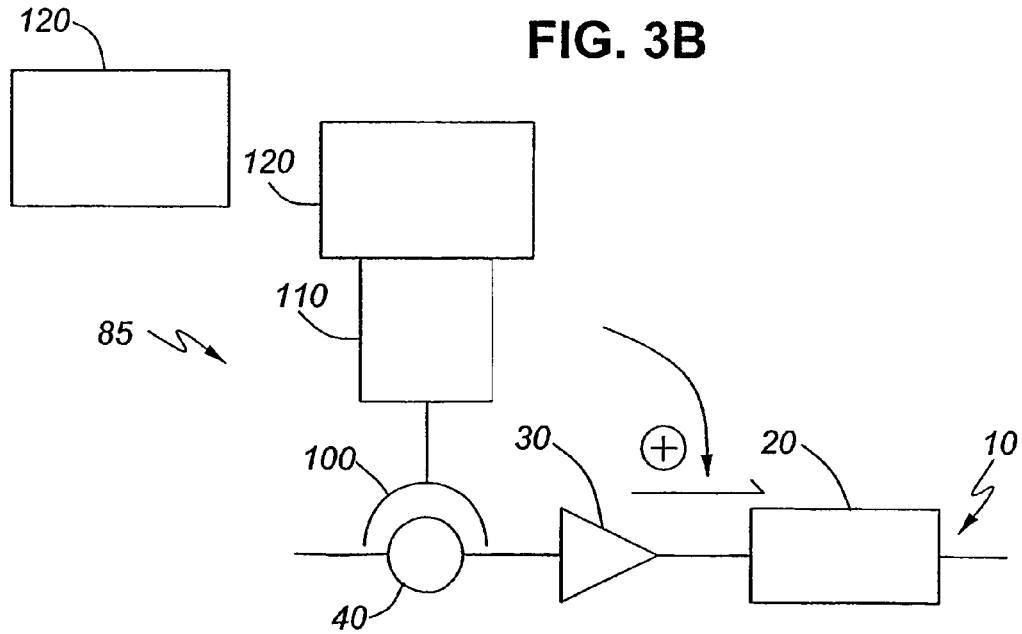

Referring now to FIGS. 3A-C, there is shown aspects of an alternate embodiment of the method of the present invention. Shown in FIG. 3A are two constructs which have been introduced into a plant cell. The constructs comprise:
1) a first nucleotide sequence (10) comprising,
   a) a nucleic acid sequence of interest (20) operatively linked to a regulatory region (30),
   b) an operator sequence (40) capable of binding a fusion protein (85, FIG. 3B), and;
2) a second nucleotide sequence (60) comprising a regulatory region (70) in operative association with a nucleotide sequence (80) encoding a fusion protein (85).

The fusion protein (85) encoded by nucleotide sequence (80) comprises,
   a) a DNA binding protein (100), or a portion of a DNA binding protein capable of binding the operator sequence (40), and;
   b) a recruitment factor protein (110), or a portion of a recruitment factor protein capable of binding a chromatin remodelling protein, for example but not limited, to free histone acetyltransferase (HAT) (120).

In the example shown in FIG. 3A-C, the operator sequence (40) is shown as being upstream from the regulatory region (30), however, the operator sequence may also be positioned downstream from the regulatory region (40), for example between the regulatory region (40) and the nucleic acid sequence of interest (20; see for example the constructs in FIG. 5A-D), within the coding region of the nucleic acid sequence of interest (20), or downstream of the nucleic acid sequence of interest (20).

Referring now to FIG. 3C, but without wishing to be bound by theory, transcription and translation of nucleotide sequence (80; FIG. 3A) produces fusion protein (85; FIG. 3B) which is capable of binding operator sequence (40; FIG. 3A) and free histone acetyltransferase (120). Dual binding of histone acetyltransferase (120) to fusion protein (85) and fusion protein (85) to operator sequence (40) facilitates enzymatic acetylation of histones (via bound histone acetyltransferase) in proximity of the nucleic acid sequence of interest (20) thereby causing an increase in the transcription of the nucleic acid sequence of interest (20).

The present invention also relates to a method of enhancing the expression of a nucleic acid sequence of interest or enhancing the transcription of one or more selected nucleotide sequences by transforming a plant with one or more constructs comprising:

1) a first nucleotide sequence comprising,
    a) a nucleic acid sequence of interest operatively linked to a regulatory region, and;
    b) an operator sequence that interacts with a fusion protein;
2) a second nucleotide sequence comprising a regulatory region in operative association with a nucleotide sequence encoding a fusion protein comprising,
    a) a DNA binding protein, or a portion of a DNA binding protein capable of binding the operator sequence, and;
    b) a histone acetyltransferase (HAT) protein, or portion of a histone acetyltransferase protein which is capable of increasing histone acetylation;

and wherein binding of the fusion protein to the operator sequence increases histone acetylation in the proximity of the nucleic acid sequence of interest within the first nucleotide sequence thereby increasing the transcription of the nucleic acid sequence of interest.

These first and second nucleotide sequences may be placed within the same or within different vectors, genetic constructs, or nucleic acid molecules. Preferably, the first nucleotide sequence and the second nucleotide sequence are chromosomally integrated into a plant or plant cell. The two nucleotide sequences may be integrated into two different genetic loci of a plant or plant cell, or the two nucleotide sequences may be integrated into a singular genetic locus of a plant or plant cell. However, the second nucleotide sequence may be integrated into the DNA of the plant or it may be present as an extra-chromosomal element, for example, but not wishing to be limiting a plasmid, or transiently expressed, for example when using viral vectors, bioloistics for transformation.

Preferably, the operator sequence is located in a nucleotide region that does not sterically hinder binding of transcription factors to the regulatory region, binding of the RNA polymerase to the nucleic acid sequence of interest, or migration of the polymerase along the DNA of the first nucleotide sequence, nucleic acid sequence of interest or both.

Figure 4A:
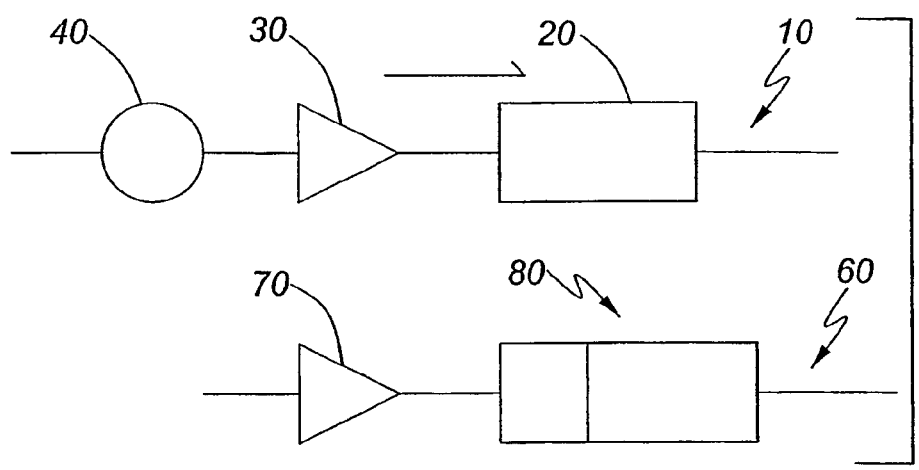
Figure 4B:
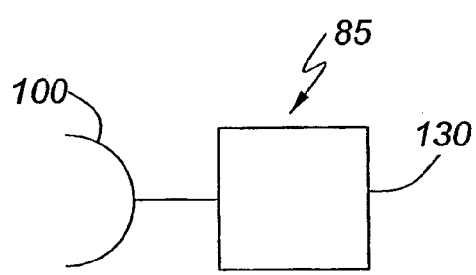
Figure 4C:
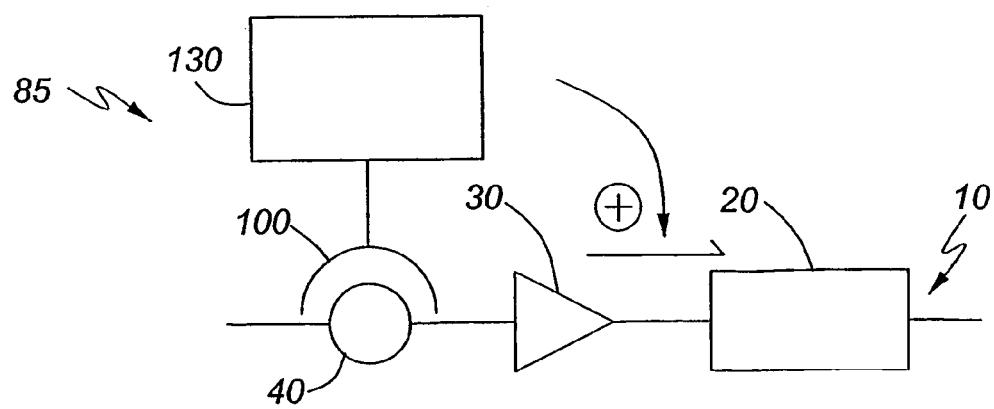

Referring now to FIGS. 4A-C, there is shown aspects of an embodiment of the method of the present invention. Shown in FIG. 4A are two constructs which have been introduced within a plant cell. The constructs comprise:

1) a first nucleotide sequence (10) comprising,
    a) a nucleic acid sequence of interest (20) operatively linked to a regulatory region (30),
    b) an operator sequence (40) capable of binding a fusion protein (85), and;
2) a second nucleotide sequence (60) comprising a regulatory region (70) in operative association with a nucleotide sequence (80) encoding a fusion protein (85).

The fusion protein (85) encoded by nucleotide sequence (80) comprises
    a) a DNA binding protein (100), or a portion of a DNA binding protein capable of binding the operator sequence (40), and;
    b) a histone acetyltransferase protein (130), or a portion of a histone acetyltransferase protein.

Referring now to FIG. 4C, but without wishing to be bound by theory, transcription and translation of nucleotide sequence (80; FIG. 4A) produces fusion protein (85; FIG. 4B) which comprises an active HAT protein (130), or portion thereof. Binding of the fusion protein (85) to the operator sequence facilitates enzymatic acetylation of histones in proximity to the nucleic acid sequence of interest (20) thereby enhancing the expression of a nucleic acid sequence of interest.

In the example shown in FIG. 4 A-C, the operator sequence (40) is shown as being upstream from the regulatory region (30), however, the operator sequence may also be positioned downstream from the regulatory region (40), for example between the regulatory region (40) and the nucleic acid sequence of interest (20; see for example the constructs in FIG. 5A-D), within the coding region of the nucleic acid sequence of interest (20), or downstream of the nucleic acid sequence of interest (20).

Also contemplated by the present invention is the control of gene expression accomplished through combinations of activator, effector and gene of interest constructs as outlined in FIGS. 29A and B (see Example 6). With reference to FIG. 29A, the expression of a gene of interest (reporter) is regulated using three constructs:
    a reporter construct (or gene of interest construct),
    an activator construct and
    an effector construct.

The gene of interest construct includes a gene of interest, for example but not limited to a reporter gene (e.g. the lacZ gene), in operative association with a regulatory element and an operator sequence.

The activator construct comprises a nucleic acid sequence encoding a recruitment factor protein, or a portion thereof, capable of binding a chromatin remodelling protein, fused with a nucleotide sequence encoding a DNA binding protein, or a fragment thereof. The recruitment factor protein may be, for example but not limited to BnSCL1, bnKCP1 or an active fragment thereof; the DNA binding protein could be, for example but not limited to VP16 or GAL4 DNA Binding domain. In this case the activator construct produces a VP16-bNSCL1 fusion protein.

The effector plasmid includes a nucleic acid sequence encoding a chromatin remodelling factor, for example but not limited to HDA19, operatively associated with a regulatory element and a nucleic acid sequence encoding a nuclear localisation signal. The constructs are expressed in eukaryotes, for example plant, animal or yeast.

When the activator construct is co-expressed with the gene of interest (reporter) construct, the DNA binding sequence binds the operator sequence of the gene of interest construct. This results in modification in the expression of the gene of interest due to interaction of the activator protein within the transcriptional machinery. In this example, the activator protein is fused to a recruitment factor protein, and the VP16-BnSCL1 fusion protein binds the Tet operator sequence of the gene activator construct resulting in increased expression of the gene of interest.

Co-expression of the effector construct, inconjuenction with the gene of interst and activator constructs, results in synthesis of a chromatin remodelling factor, in this case HAD19, which associates with the recruitment factor protein, BnSCL1. Association of HDAC with the construct expressing the gene of interst, reduces expression of the gene of interest.

In a second aspect, the expression of a gene of interest is regulated using two constructs: a gene of interest (reporter)+activator and an effector construct as shown in FIG. 29B. Expression of the reporter+activator construct results in an increased expression of the gene of interest due to binding of the activator portion of the construct to the operator sequence of the gene of interest construct. This association may be inhibited in the presence of tetracycline. As in the case outlined with reference to FIG. 29A, above, co-expression of the effector construct results in reduced expression of the gene of interest due to association of HDAC to the activator-recruitment factor fusion protein (VP16-BnSCL1 fusion)

The present invention also provides for a method to regulate expression of a nucleic acid sequence of interest, wherein the nucleic acid sequence of interest comprises an endogenous sequence. In this embodiment, a nucleotide sequence comprising a regulatory region in operative association with a nucleotide sequence encoding a recruitment factor, or a portion thereof, that is known to interact with a factor that binds the nucleic acid sequence of interest, is expressed in the host. The recruitment factor protein, or a portion thereof is capable of binding a chromatin remodelling protein, for example but not limited, HDAC or HAT, and the recruitment factors also interacts with endogenous factors that bind the nucleotide sequence of interest (e.g. transcription factors). In this manner, expression of the recruitment factor in a temporal, tissue specific, or induced manner will result in the expression of the recruitment factor that binds the chromatin remodelling factor and transcription factor resulting in modulation of expression of the nucleic acid sequence of interest. A non-limiting example of this embodiment includes the expression of bnKCP1 and its interaction with HDAC and transcription factors ERF, SEBF or CBF.

Therefore, the present invention provides a method to regulate expression of an endogenous nucleic acid sequence of interest in a plant comprising:
i) introducing into the plant a nucleotide sequence comprising, a regulatory region, operatively linked with a nucleotide sequence encoding a recruitment factor protein, the recruitment factor protein capable of binding an endogenous DNA binding protein, the endogenous DNA binding protein characterized in binding a segment of a DNA sequence of the endogenous nucleotide sequence of interest, and;
ii) growing the plant, wherein expression of the nucleotide sequence produces the recruitment factor thereby regulating expression of the endogenous nucleic acid sequence of interest.

An alternate embodiment of the present invention includes a method to regulate expression of an endogenous nucleic acid sequence of interest. In this example, a DNA binding protein, or a portion thereof, known to interact with the DNA of an endogenous nucleic acid sequence of interest is fused to a chromatin remodelling factor. Expression of the fusion protein permits the recruitment factor portion of the fusion protein to interact or bind with a chromatin remodelling, for example but not limited to HDAC or HAT, and the DNA binding portion of the fusion protein binds the nucleotide sequence of interest. In this manner, expression of the fusion protein in a temporal, tissue specific, or induced manner will result in the expression of a recruitment factor that binds a chromatin remodelling factor and the DNA of a nucleic acid sequence of interest, resulting in modulation of expression of the endogenous nucleic acid sequence of interest. Examples of DNA binding proteins, or portions thereof, that bind endogenous nucleic acid sequences of interest, which are not to be considered limiting, include ERF, SEBF or CBF. A non-limiting example of a recruitment factor is bnKCP1 or BnSCL1.

Therefore, the present invention also provides a method to regulate expression of an endogenous nucleic acid sequence of interest in a plant comprising:
i) introducing into the plant a nucleotide sequence comprising, a regulatory region, operatively linked with a nucleotide sequence encoding a fusion protein, the fusion protein comprising,
  a) a DNA binding protein, or a portion thereof, capable of binding a segment of a DNA sequence of the endogenous nucleotide sequence of interest, and;
  b) a recruitment factor protein, or a portion thereof, capable of binding a chromatin remodelling protein; and
ii) growing the plant, wherein expression of the nucleotide sequence produces the fusion protein that regulates expression of the endogenous nucleic acid sequence of interest.

Also contemplated by the present invention is a method of increasing cold tolerance in a plant. The method comprises providing a plant having a nucleotide sequence of interest operatively linked to a first regulatory region; the nucleotide sequence of interest encodes bnKCP1, or a fragment thereof. The plant is maintained under conditions where bnKCP1 is expressed. In this manner, the plant expressing bnKCP1 is preconditioned for cold adaptation and exhibits increased cold tolerance.

By the term cold in the context of cold tolerance, it is meant a temperature in the range of about $-10°$ C. to about $10°$ C. An example of cold temperature, without wishing to be limiting, is a temperature in the range of about $-8°$ C. to about $8°$ C.; a further example is a temperature of about $-10$ to about $-1°$ C.

Sequences of the present invention are listed in Table 2.

TABLE 2

| | | |
|---|---|---|
| SEQ ID NO:1 | aa seq of wild-type ROS (*A. tumefaciens*) | FIG. 1A (WT-ROS) |
| SEQ ID NO:2 | Nucl seq synthetic ROS optimized for plant, with NLS | FIG. 1B |
| SEQ ID NO:3 | Consensus nucl seq of composite ROS | FIG. 1C |
| SEQ ID NO:4 | aa seq of synthetic ROS | FIG. 1A, 1C |
| SEQ ID NO:5 | ROS binding sequence | FIG. 1E |
| SEQ ID NO:6 | aa seq of NLS (PKKKRKV) | |
| SEQ ID NO:7 | ROS operator sequence | |

TABLE 2-continued

Figures 10, 10B, 10C:
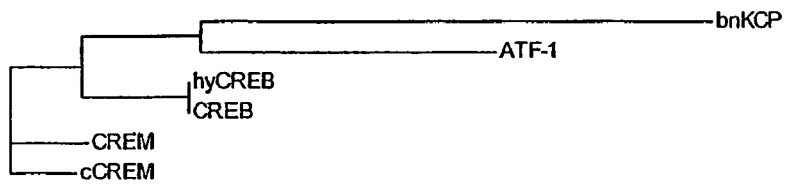
FIG. 10 shows alignments of bnKCP1 and sequence comparison of kinase inducible domains (KIDs) in bnKCP1 and CREB family members.
FIG. 10(B) shows alignment of the amino acid sequences of bnKCP1 (SEQ ID NO:75), hydra CREB (hyCREB). (SEQ ID NO:77), canfa CREM (cCREM) (SEQ ID NO:80), and mammalian ATF-1 (SEQ ID NO:76), CREB (SEQ ID NO:78) and CREM (SEQ ID NO:79). Diamonds indicate the conserved phosphorylation site of protein kinase A.
FIG. 10(C) shows a phylogenetic tree of the KIDs sequences using the NTI Vector program.

| | | |
|---|---|---|
| SEQ ID NO:8 | IPT gene operator sequence | |
| SEQ ID NO:9 | Operator sequence binding to ERF | |
| SEQ ID NO:10 | Operator sequence binding to SEBF | |
| SEQ ID NO:11 | Operator sequence binding to CBF | |
| SEQ ID NO:12 | Operator sequence binding to CBF | |
| SEQ ID NO:13 | NLS of AGAMOUS protein | Table 1, page 30 |
| SEQ ID NO:14 | NLS of TGA-1A protein | Table 1, page 30 |
| SEQ ID NO:15 | NLS of TGA-1B protein | Table 1, page 30 |
| SEQ ID NO:16 | NLS of O2 NLS B protein | Table 1, page 30 |
| SEQ ID NO:17 | NLS of NIa protein | Table 1, page 30 |
| SEQ ID NO:18 | NLS of nucleoplasmin protein | Table 1, page 30 |
| SEQ ID NO:19 | NLS of NO38 protein | Table 1, page 30 |
| SEQ ID NO:20 | NLS of N1/N2 protein | Table 1, page 30 |
| SEQ ID NO:21 | NLS of Glucocorticoid receptor | Table 1, page 30 |
| SEQ ID NO:22 | NLS of Glucocorticoid a receptor | Table 1, page 30 |
| SEQ ID NO:23 | NLS of Glucocorticoid b receptor | Table 1, page 30 |
| SEQ ID NO:24 | NLS of Progesterone receptor | Table 1, page 30 |
| SEQ ID NO:25 | NLS of Androgen receptor | Table 1, page 30 |
| SEQ ID NO:26 | NLS of p53 protein | Table 1, page 30 |
| SEQ ID NO:27 | VirC/VirD operator seq | FIG. 1D |
| SEQ ID NO:28 | ROS-OPDS, p74-315 | |
| SEQ ID NO:29 | ROS-OPDA, p74-315 | |
| SEQ ID NO:30 | ROS-OPUS, p74-316 | |
| SEQ ID NO:31 | ROS-OPUA, p74-316 | |
| SEQ ID NO:32 | ROS-OPPS, p74-309 | |
| SEQ ID NO:33 | ROS-OPPA, p74-309 | |
| SEQ ID NO:34 | ROS-OP1, p74-508 | |
| SEQ ID NO:35 | ROS-OP2, p74-508 | |
| SEQ ID NO:36 | tms2 promoter sense primer, p74-508 | |
| SEQ ID NO:37 | tms2 promoter anti-sense primer, p74-508 | |
| SEQ ID NO:38 | Actin2 promoter sense primer, p74-501 | |
| SEQ ID NO:39 | Actin2 promoter anti-sense primer, p74-501 | |
| SEQ ID NO:40 | p74-315 seq from EcoRV to ATG of GUS | |
| SEQ ID NO:41 | p74-316 seq from EcoRV to ATG of GUS | |
| SEQ ID NO:42 | p74-309 seq from EcoRV to ATG of GUS | |
| SEQ ID NO:43 | p74-118 seq from EcoRV to ATG of GUS | |
| SEQ ID NO:44 | Forward primer for HDA19 *A. thaliana*, pDBLeu-HDA19 | |
| SEQ ID NO:45 | Reverse primer for HDA19 *A. thaliana*, pDBLeu-HDA19 | |
| SEQ ID NO:46 | Forward primer for Gcn5 *Arabidopsis*, GST-Gcn5 | |
| SEQ ID NO:47 | Reverse primer for Gcn5 *Arabidopsis*, GST-Gcn5 | |
| SEQ ID NO:48 | Reverse primer for HDA19, GST-HDA19 | |
| SEQ ID NO:49 | Forward primer for bnKCP1, 1-80, 1-160 (generation of mutants) | |
| SEQ ID NO:50 | Reverse primer for bnKCP1 1-160 (generation of mutants) | |
| SEQ ID NO:51 | Reverse primer for bnKCP1 1-80 (generation of mutants) | |
| SEQ ID NO:52 | Reverse primer for bnKCP1 (generation of mutants) | |
| SEQ ID NO:53 | Forward primer for bnKCP1, 1-80 and 1-160 (in vivo assay and transactivation assay) | |
| SEQ ID NO:54 | Reverse primer for bnKCP1 (in vivo assay and transactivation assay) and 81-215 (transactivation assay) | |
| SEQ ID NO:55 | Reverse primer for bnKCP1 1-160 (in vivo assay and transactivation assay) | |
| SEQ ID NO:56 | Reverse primer for bnKCP1 1-80 (in vivo assay and transactivation assay) | |
| SEQ ID NO:57 | Forward primer for bnKCP1G188 | |
| SEQ ID NO:58 | Reverse primer for bnKCP1G188 | |
| SEQ ID NO:59 | Forward primer for bnKCP1 81-215 (transactivation assay) | |
| SEQ ID NO:60 | Forward primer for entire coding region of bnKCP1 | |
| SEQ ID NO:61 | Reverse primer for entire coding region of bnKCP1 | |
| SEQ ID NO:62 | pat7 NLS (PLNKKRR) | |
| SEQ ID NO:63 | aa seq of ROSR (ROS repressor) | FIG. 1A |
| SEQ ID NO:64 | aa seq of ROSAR (ROS repressor) | FIG. 1A |
| SEQ ID NO:65 | aa seq of MucR (ROS repressor) | FIG. 1A |
| SEQ ID NO:66 | VirC/VirD DNA binding site seq (1) | FIG. 1D |
| SEQ ID NO:67 | VirC/VirD DNA binding site seq (2) | FIG. 1D |
| SEQ ID NO:68 | ipt DNA binding site seq (1) | FIG. 1D |
| SEQ ID NO:69 | ipt DNA binding site seq (2) | FIG. 1D |
| SEQ ID NO:70 | Consensus DNA binding site seq | FIG. 1D |
| SEQ ID NO:71 | bnKCP aa seq | FIG. 10A |
| SEQ ID NO:72 | atKCP aa seq | FIG. 10A |
| SEQ ID NO:73 | atKCL1 aa seq | FIG. 10A |
| SEQ ID NO:74 | atKCL2 aa seq | FIG. 10A |
| SEQ ID NO:75 | bnKCP aa seq | FIG. 10B |
| SEQ ID NO:76 | ATF-1 aa seq | FIG. 10B |
| SEQ ID NO:77 | hyCREB aa seq | FIG. 10B |
| SEQ ID NO:78 | CREB aa seq | FIG. 10B |
| SEQ ID NO:79 | CREM aa seq | FIG. 10B |
| SEQ ID NO:80 | cCREM aa seq | FIG. 10B |
| SEQ ID NO:81 | aa seq of BnSCL1 | FIG. 20 |

TABLE 2-continued

| SEQ ID NO:82 | aa seq of atSCL15 | FIG. 20 |
| SEQ ID NO:83 | aa seq of 1sSCR | FIG. 20 |
| SEQ ID NO:84 | BnSCL1 sense primer | |
| SEQ ID NO:85 | BnSCL1 anti-sense primer | |
| SEQ ID NO:86 | BnIAA1 sense primer | |
| SEQ ID NO:87 | BnIAA1 anti-sense primer | |
| SEQ ID NO:88 | BnIAA12 sense primer | |
| SEQ ID NO:89 | BnIAA12 anti-sense primer | |
| SEQ ID NO:90 | Forward primer for BnSCL1, BnSCL1$^{1-358}$, BnSCL1$^{1-261}$, BnSCL1$^{1-217}$ and BnSCL1$^{1-145}$ for pET-28b vector | |
| SEQ ID NO:91 | Reverse primer for BnSCL1 for pET-28b vector | |
| SEQ ID NO:92 | Reverse primer for BnSCL1$^{1-358}$ for pET-28b vector | |
| SEQ ID NO:93 | Reverse primer for BnSCL1$^{1-261}$ for pET-28b vector | |
| SEQ ID NO:94 | Reverse primer for BnSCL1$^{1-217}$ for pET-28b vector | |
| SEQ ID NO:95 | Reverse primer for BnSCL1$^{1-145}$ for pET-28b vector | |
| SEQ ID NO:96 | Forward primer for BnSCL1, BnSCL1$^{1-358}$, BnSCL1$^{1-261}$, BnSCL1$^{1-217}$ and BnSCL1$^{1-145}$ for pPC86 vector | |
| SEQ ID NO:97 | Forward primer for BnSCL1$^{146-358}$ for PC86 vector | |
| SEQ ID NO:98 | Forward primer for BnSCL1$^{218-434}$ for PC86 vector | |
| SEQ ID NO:99 | Reverse primer for BnSCL1 and BnSCL1$^{218-434}$ for PC86 vector | |
| SEQ ID NO:100 | Reverse primer for BnSCL1$^{1-358}$ for PC86 vector | |
| SEQ ID NO:101 | Reverse primer for BnSCL1$^{1-261}$ for PC86 vector | |
| SEQ ID NO:102 | Reverse primer for BnSCL1$^{1-217}$ for PC86 vector | |
| SEQ ID NO:103 | Reverse primer for BnSCL1$^{1-145}$ for PC86 vector | |
| SEQ ID NO:104 | aa seq of LXXLL motif($^{148}$LGSLL$^{152}$) | |

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Materials and Methods

Plant Material

Wild type *Arabidopsis thaliana*, ecotype Columbia, seeds were germinated on RediEarth (W. R. Grace & Co.) soil in pots covered with window screens under green house conditions (~25° C., 16 hr light). Emerging bolts were cut back to encourage further bolting. Plants were used for transformation once multiple secondary bolts had been generated.

Plant Transformation

Plant transformation was carried out according to the floral dip procedure described in Clough and Bent (1998). Essentially, *Agrobacterium tumefaciens* transformed with the construct of interest (using standard methods as known in the art) was grown overnight in a 100 ml Luria-Bertani Broth (10 g/L NaCl, 10 g/L tryptone, 5 g/L yeast extract) containing 50 µg/ml kanamycin. The cell suspension culture was centrifuged at 3000×g for 15 min. The pellet was resuspended in 1 L of the transformation buffer (sucrose (5%), Silwet L77 (0.05%)(Loveland Industries). The above-ground parts of the *Arabidopsis* plants were dipped into the *Agrobacterium* suspension for ~1 min and the plants were then transferred to the greenhouse. The entire transformation process was repeated twice more at two day intervals. Plants were grown to maturity and seeds collected. To select for transformants, seeds were surface sterilized by washing in 0.05% Tween 20 for 5 minutes, with 95% ethanol for 5 min, and then with a solution containing sodium hypochlorite (1.575%) and Tween 20 (0.05%) for 10 min followed by 5 washings in sterile water. Sterile seeds were plated onto either Pete Lite medium (20-20-20 Peter's Professional Pete Lite fertilizer (Scott) (0.762 g/l), agar (0.7%), kanamycin (50 µg/ml), pH 5.5) or MS medium (MS salts (0.5×)(Sigma), B5 vitamins (1×), agar (0.7%), kanamycin (50 µg/ml) pH 5.7). Plates were incubated at 20° C., 16 hr light/8 hr dark in a growth room. After approximately two weeks, seedlings possessing green primary leaves were transferred to soil for further screening and analysis:

Example 1

Optimization of ROS Protein Coding Region

The ros nucleotide sequence is derived from *Agrobacterium tumefaciens* (SEQ ID NO:1; FIG. 1A). Analysis of the protein coding region of the ros nucleotide sequence indicates that the codon usage may be altered to better conform to plant translational machinery. The protein coding region of the ros nucleotide sequence was therefore modified to optimize expression in plants (SEQ ID NO:2; FIG. 1B). The nucleic acid sequence of the ROS repressor was examined and the coding region modified to optimize for expression of the gene in plants, using a procedure similar to that outlined by Sardana et al. (1996). A table of codon usage from highly expressed genes of dicotyledonous plants was compiled using the data of Murray et al. (1989). The ros nucleotide sequence was also modified (SEQ ID NO:2; FIG. 1B) to ensure localization of the ROS repressor to the nucleus of plant cells, by adding a SV40 nuclear localization signal (Rizzo, P. et al., 1999; The nuclear localization signal resides at amino acid positions 126-132; accession number AAF28270).

The ros gene is cloned from *Agrobacterium tumefaciens* by PCR. The nucleotide sequence encoding the ROS protein is expressed in, and purified from, *E. coli*, and the ROS protein used to generate an anti-ROS antiserum in rabbits using standard methods (Sambrook et al.).

Example 2

Constructs Placing a Nucleic Acid Sequence of Interest Under Transcriptional Control of Regulatory Regions that have been Modified to Contain ROS Operator Sites, and Preparation of Reporter Lines p74-315: Construct for The Expression of GUS Gene Driven by a CaMV 35S Promoter Containing a ROS Operator Downstream of TATA Box (FIG. 5(A)).

The BamHI-EcoRV fragment of CaMV 35S promoter in pBI121 is cut out and replaced with a similar synthesized DNA fragment in which the 25 bp immediately downstream of the TATA box were replaced with the ROS operator sequence:

```
TATATTTCAATTTTATTGTAATATA.    (SEQ ID NO: 7)
```

Two complementary oligos, ROS-OPDS (SEQ ID NO:28) and ROS-OPDA (SEQ ID NO:29), with built-in BamHI-EcoRV ends, and spanning the BamHI-EcoRV region of CaMV35S, in which the 25 bp immediately downstream of the TATA box are replaced with the ROS operator sequence (SEQ ID NO: 7), are annealed together and then ligated into the BamHI-EcoRV sites of CaMV35S.

```
                                       (SEQ ID NO:28)
ROS-OPDS:
5'-ATC TCC ACT GAC GTA AGG GAT GAC GCA CAA TCC CAC
TAT CCT TCG CAA GAC CCT TCC TCT ATA TAA TAT ATT
TCA ATT TTA TTG TAA TAT AAC ACG GGG GAC TCT AGA G-
3'
```

```
                                       (SEQ ID NO:29)
ROS-OPDA:
5'-G ATC TCT TAG AGT CCC CCG TGT TAT ATT ACA ATA
AAA TTG AAA TAT ATT ATA TAG AGG AAG GGT CTT GCG
AAG GAT AGT GGG ATT GTG CGT CAT CCC TTA CGT CAG
TGG AGA T-3'
```

The p74-315 sequence from the EcoRV site (GAT ATC) to the first codon (ATG) of GUS is shown below (TATA box—lower case in bold; the synthetic ROS sequence—bold caps; a transcription start site—ACA, bold italics; BamHI site—GGA TCC; and the first of GUS, ATG, in italics; are also indicated):

```
                                       (SEQ ID NO:40)
5'-GAT ATC TCC ACT GAC GTA AGG GAT GAC GCA CAA TCC
CAC TAT CCT TCG CAA GAC CCT TCC TCt ata taA TAT
ATT TCA ATT TTA TTG TAA TAT A^AC ACG GGG GAC TCT
AGA GGA TCC CCG GGT GGT CAG TCC CTT ATG-3'
``` p74-316: Construct for The Expression of GUS Driven by a CaMV 35S Promoter Containing a ROS Operator Upstream of TATA Box (FIG. 5(B)).

The BamHI-EcoRV fragment of CaMV 35S promoter in pBI121 is cut out and replaced with a similar synthesized DNA fragment in which the 25 bp immediately upstream of the TATA box are replaced with the ROS operator sequence (SEQ ID NO: 7). Two complementary oligos, ROS-OPUS (SEQ ID NO:30) and ROS-OPUA (SEQ ID NO:31), with built-in BamHI-EcoRV ends, and spanning the BamHI-EcoRV region of CaMV35S, in which the 25 bp immediately upstream of the TATA box were replaced with a ROS operator sequence (SEQ ID NO: 7), are annealed together and then ligated into the BamHI-EcoRV sites of CaMV35S.

```
                                       (SEQ ID NO:30)
ROS-OPUS:
5'-ATC TCC ACT GAC GTA AGG GAT GAC GCA CAA TCT ATA
TTT CAA TTT TAT TGT AAT ATA CTA TAT AAG GAA GTT
CAT TTC ATT TGG AGA GAA CAC GGG GGA CTC TAG AG-3'
```

```
                                       (SEQ ID NO:31)
ROS-OPUA:
5'-G ATC CTC TAG AGT CCC CCG TGT TCT CTC CAA ATG
AAA TGA ACT TCC TTA TAT AGT ATA TTA CAA TAA AAT
TGA AAT ATA GAT GTG CGT CA TCC CTT ACG TCA GTG
GAG AT-3'
```

The p74-316 sequence from the EcoRV site (GAT ATC) to the first codon (ATG) of GUS is shown below (TATA box—lower case in bold; the synthetic ROS sequence—bold caps; a transcription start site—ACA, bold italics; BamHI site—GGA TCC; the first codon of GUS, ATG-italics, are also indicated):

```
                                       (SEQ ID NO:41)
5'-GAT ATC TCC ACT GAC GTA AGG GAT GAC GCA CAA TCT
ATA TTT CAA TTT TAT TGT AAT ATA Cta tat aAG GAA
GTT CAT TTC ATT TGG AGA GA^A C^AC GGG GGA CTC TAG
AGG ATC CCC GGG TGG TCA GTC CCT TAT G-3'
``` p74-309: Construct for The Expression of GUS Driven by a CaMV 35S Promoter Containing ROS Operators Upstream and Downstream of TATA Box (FIG. 5(C)).

The BamHI-EcoRV fragment of CaMV 35S promoter in pBI121 is cut out and replaced with a similar synthesized DNA fragment in which the 25 bp immediately upstream and downstream of the TATA box were replaced with two ROS operator sequences (SEQ ID NO: 7). Two complementary oligos, ROS-OPPS (SEQ ID NO:32) and ROS-OPPA (SEQ ID NO:33), with built-in BamHI-EcoRV ends, and spanning the BamHI-EcoRV region of CaMV35S, in which the 25 bp immediately upstream and downstream of the TATA box are replaced with two ROS operator sequences, each comprising the sequence of SEQ ID NO: 7 (in italics, below), are annealed together and ligated into the BamHI-EcoRV sites of CaMV35S.

```
                                       (SEQ ID NO:32)
ROS-OPPS:
5'-ATC TCC ACT GAC GTA AGG GAT GAC GCA CAA TCT ATA
TTT CAA TTT TAT TGT AAT ATA CTA TAT AAT ATA TTT
CAA TTT TAT TGT AAT ATA ACA CGG GGG ACT CTA GAG-3'
```

```
                                       (SEQ ID NO:33)
ROS-OPPA:
5'-G ATC CTC TAG AGT CCC CCG TGT TAT ATT ACA ATA
AAA TTG AAA TAT ATT ATA TAG TAT ATT ACA ATA AAA
TTG AAA TAT AGA TTG TGC GTC ATC CCT TAC GTC AGT
GGA GAT-3'
```

Figure 5A:
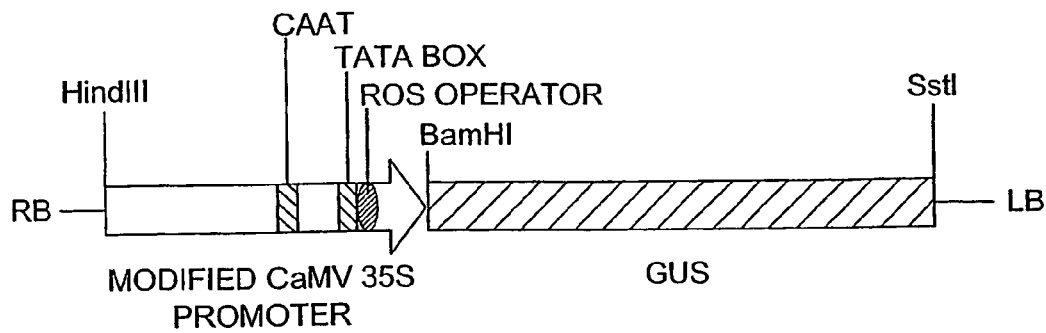
FIG. 5(A) shows the nucleotide construct p74-315 in which a CaMV35S regulatory region, modified to contain a ROS operator site downstream of the TATA box, is operatively linked to a gene of interest (β-glucuronidase; GUS).
Figure 5B:
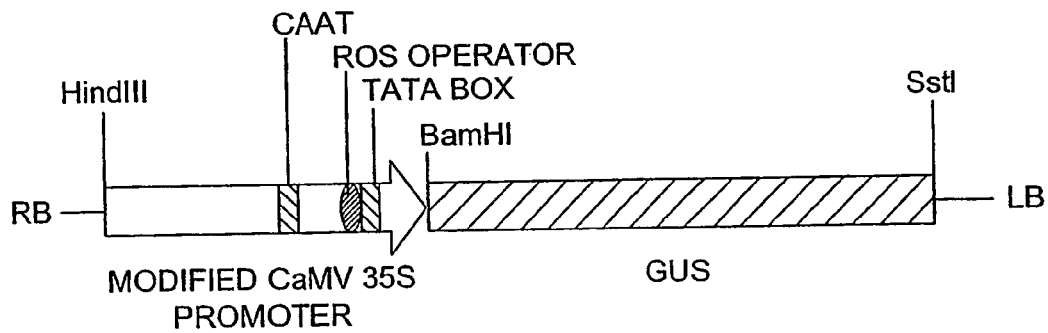
FIG. 5(B) shows the nucleotide construct p74-316 in which a CaMV35S regulatory region is modified to contain a ROS operator site upstream of the:TATA box is operatively linked to the protein encoding region of GUS.
Figure 5C:
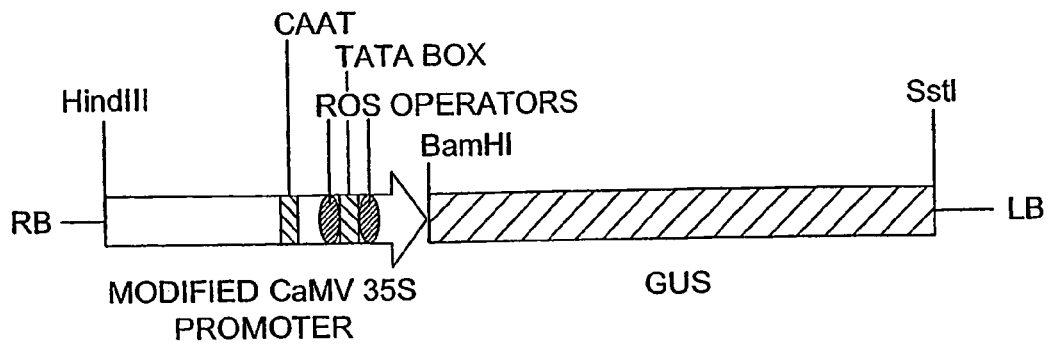
FIG. 5(C) shows the nucleotide construct p74-309 in which a CaMV35S regulatory region modified to contain ROS operator sites upstream and downstream of the TATA box is transcriptionally fused (i.e. operatively linked) to the protein encoding region of GUS.
Figure 5D:
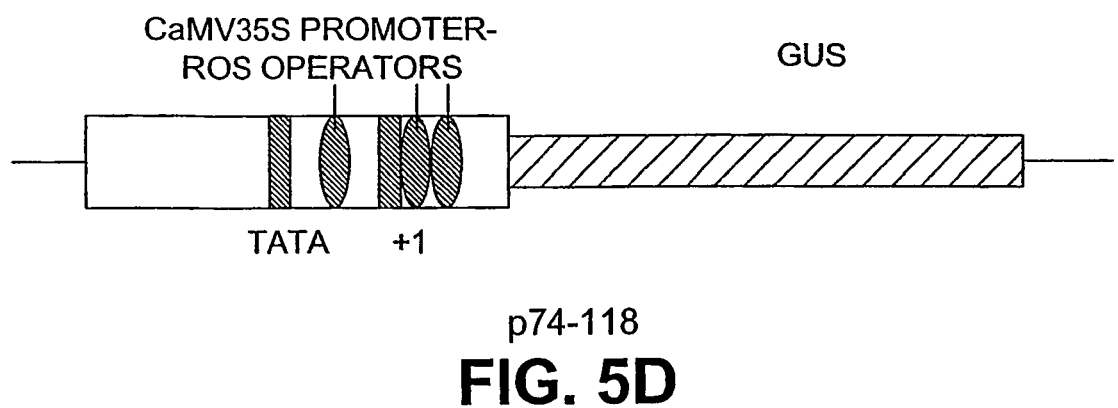
FIG. 5(D) shows construct p74-118 comprising a 35S regulatory region with three ROS operator sites downstream from the TATA box. The 35S regulatory region is operatively linked to the gene of interest (GUS).

The p74-309 sequence from the EcoRV site (GAT ATC) to the first codon (ATG) of GUS is shown below (TATA box—lower case in bold; two synthetic ROS sequence—bold caps; a transcription start site—ACA, bold italics; BamHI site—GGA TCC; the first codon of GUS, ATG-italics, are also indicated):

```
                                       (SEQ ID NO:42)
5'-GAT ATC TCC ACT GAC GTA AGG GAT GAC GCA CAA TCT
ATA TTT CAA TTT TAT TGT AAT ATA Cta tat aAT ATA
TTT CAA TTT TAT TGT AAT ATA A^CA CGG GGG ACT CTA
GAG GAT CCC CGG GTG GTC AGT CCC TTA TG-3'
``` p74-118 Construct for The Expression of GUS Driven by a CaMV 35S Promoter Containing three ROS Operators Downstream of TATA Box (FIG. 5(D)).

The BamHI-EcoRV fragment of CaMV 35S promoter in pBI121 is cut out and replaced with a similar synthesized DNA fragment in which a region downstream of the TATA box was replaced with three ROS operator sequences (SEQ ID NO:43). The first of the three synthetic ROS operator sequences is positioned immediately of the TAT box, the other two ROS operator sequence are located downstream of the transcriptional start site (ACA). Two complementary oligos with built-in BamHI-EcoRV ends were prepared as describe above for the other constructs were annealed together and ligated into the BamHI-EcoRV sites of CaMV35S.

The p74-118 sequence from the EcoRV site (GAT ATC) to the first codon (ATG) of GUS is shown below (TATA box—lower case in bold; three synthetic ROS sequence—bold caps; a transcription start site—ACA, bold italics; BamHI site—GGA TCC; the first codon of GUS, ATG-italics, are also indicated):

```
                                              (SEQ ID NO:43)
5'-GAT ATC TCC ACT GAC GTA AGG GAT GAC GCA CAA TCC

CAC TAT CCT TCG CAA GAC CCT TCC TCt ata taA TAT

ATT TCA ATT TTA TTG TAA TAT AAC ACG GGG GAC TCT

AGA GGA TCC TAT ATT TCA ATT TTA TTG TAA TAT AGC

TAT ATT TCA ATT TTA TTG TAA TAT AAT CGA TTT CGA

ACC CGG GGT ACC GAA TTC CTC GAG TCT AGA GGA TCC

CCG GGT GGT CAG TCC CTT ATG-3'
``` p76-508: Construct for The Expression of The GUS Gene Driven by the tms2 Promoter Containing a ROS Operator (FIG. 6(B)).

The tms2 promoter is PCR amplified from genomic DNA of *Agrobacterium tumefaciens* 33970 using the following primers:

```
sense primer:                      (SEQ ID NO:36)
5'-TGC GGA TGC ATA AGC TTG CTG ACA TTG CTA GAA
AAG-3' anti-sense primer:                 (SEQ ID NO:37)
5'-CGG GGA TCC TTT CAG GGC CAT TTC AG-3'
```

The 352 bp PCR fragment is cloned into the EcoRV site of pBluescript, and sub-cloned into pGEM-7Zf(+). Two complementary oligos, ROS-OP1 (SEQ ID NO:34) and ROS-OP2 (SEQ ID NO:35), containing two ROS operators (in italics, below), are annealed together and cloned into pGEM-7Zf(+) as a BamHI/ClaI fragment at the 3' end of the tms2 promoter. This promoter/operator fragment is then sub-cloned into pBI121 as a HindIII/XbaI fragment, replacing the CaMV 35S promoter fragment.

```
ROS-OP1:                           (SEQ ID NO:34)
5'-GAT CCT ATA TTT CAA TTT TAT
TGT AAT ATA GCT ATA
TTT CAA TTT TAT TGT AAT ATA AT-3'

ROS-P2:                            (SEQ ID NO:35)
5'-CGA TTA TAT TAC AAT AAA ATT
GAA ATA TAG CTA TAT
TAC AAT AAA ATT GAA ATA TAG-3'.
```

As a control, p76-507 comprising a tms2 promoter (without any operator sequence) fused to GUS (FIG. 4(A)), is also prepared.

p74-501: Construct for The Expression of The GUS Gene Driven by The Actin2 Promoter Containing a ROS operator (FIG. 7B)).

The Actin2 promoter is PCR amplified from genomic DNA of *Arabidopsis thaliana* ecotype Columbia using the following primers:

```
Sense primer:                      (SEQ ID NO:38)
5'-AAG CTT ATG TAT GCA AGA
GTC AGC-3'
                SpeI Anti-sense primer:                 (SEQ ID NO:39)
5'-TTG ACT AGT ATC AGC CTC
AGC CAT-3'
```

The PCR fragment is cloned into pGEM-T-Easy. Two complementary oligos, ROS-OP1 (SEQ ID NO:34) and ROS-OP2 (SEQ ID NO:35), with built-in BamHI and ClaI sites, and containing two ROS operators, are annealed together and inserted into the Actin2 promoter at the BglII/ClaI sites replacing the BglII/ClaI fragment. This modified promoter is inserted into pBI121vector as a HindIII/BamHI fragment.

Figure 7A:
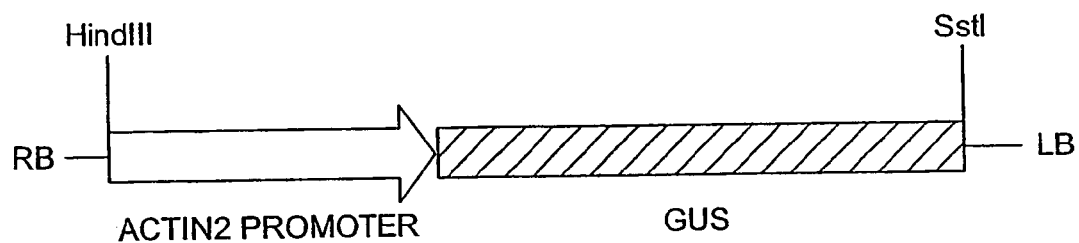
FIG. 7(A) shows the nucleotide construct p75-101 in which an actin2 regulatory region is operatively linked to a gene of interest (the β-glucuronidase (GUS) reporter gene).
Figure 7B:
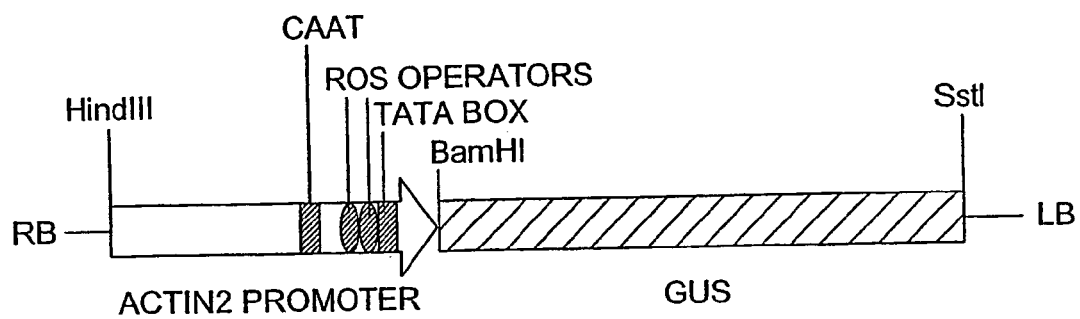
FIG. 7(B) shows the nucleotide construct p74-501 in which an actin2 regulatory region modified to contain two tandemly repeated ROS operator sites upstream of the TATA box is transcriptionally fused (operatively linked) to the a gene of interest (GUS).

As a control, p75-101, comprising an actin2 promoter (without any operator sequence) fused to GUS (FIG. 7(A)), is also prepared.

Figure 8A:
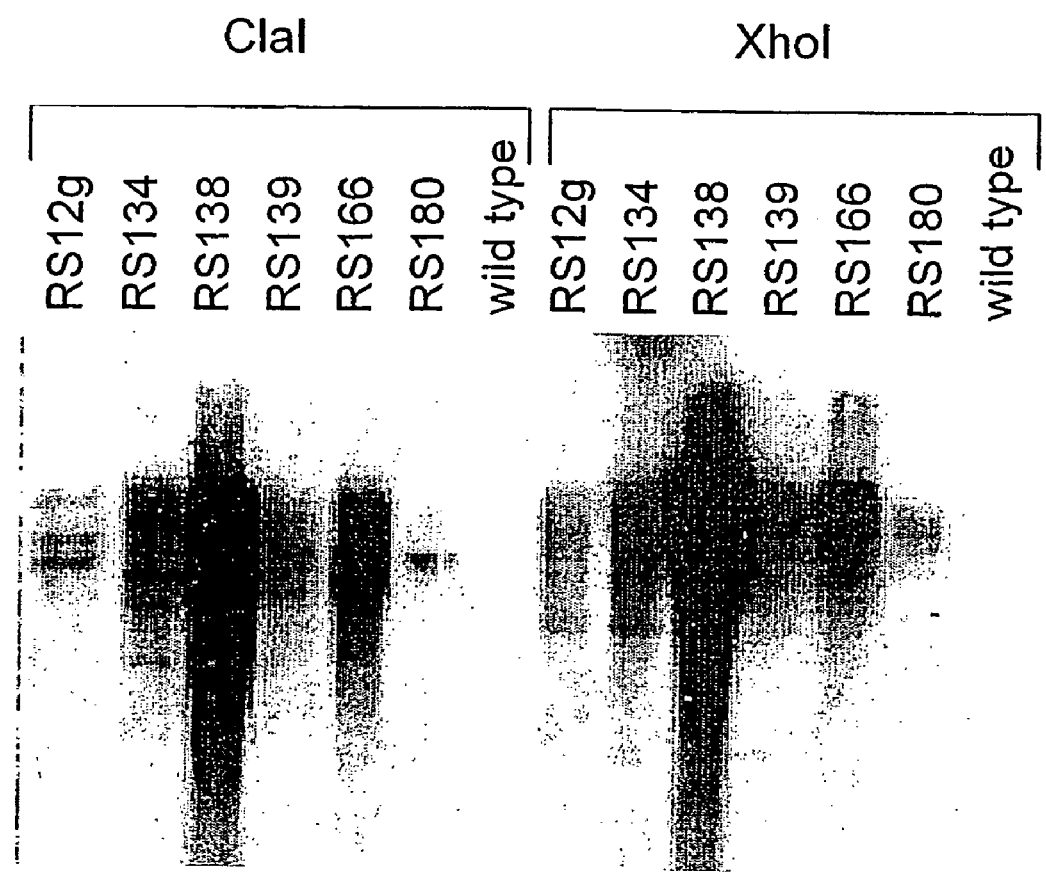
FIG. 8(A) shows Southern analysis of a plant comprising a first genetic construct, p74-309 (35S-operator sequence-GUS; see FIG. 5(C) for map). DNA was digested with ClaI or XhoI and the blot was probed with the ORF of the GUS gene.
Figure 8B:
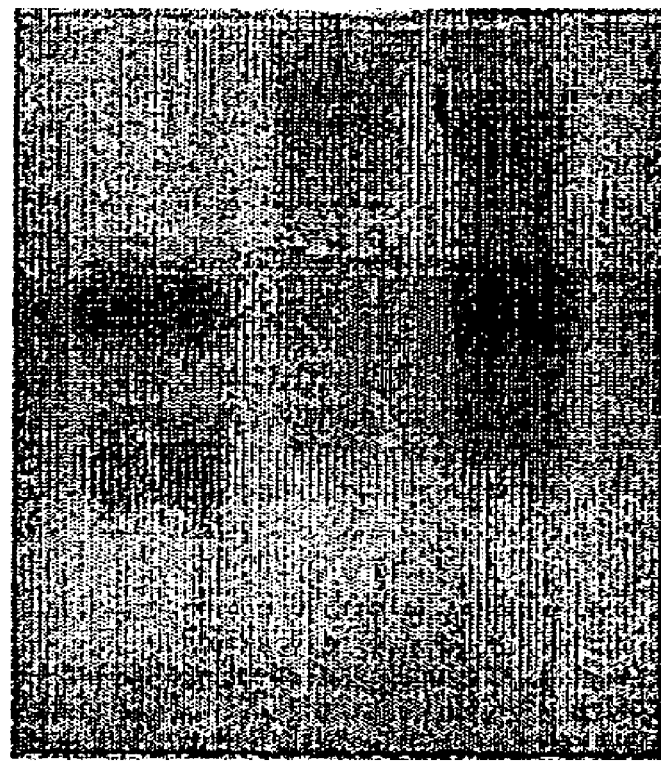
FIG. 8(B) shows Southern analysis of a plant comprising a second genetic construct p75-101 (see FIG. 7A). HindIII digests were probed with NPTII.

The various constructs are introduced into *Arabidopsis*, as described above, and transgenic plants are generated. Transformed plants are verified using PCR or Southern analysis. FIG. 8(A) show Southern analysis of transgenic plants comprising a first genetic construct, for example, p74-309 (35S-ROS operator sequence-GUS, FIG. 5(C))

Example 3

Crossing of Transgenic Lines Containing Fusion Constructs with Transgenic Lines Containing GUS Reporter Constructs Transgenic *Arabidopsis* lines containing fusion constructs (second genetic constructs) are crossed with lines containing appropriate reporter (GUS) constructs (first genetic constructs). To perform the crossing, open flowers are removed from plants of the reporter lines. Fully formed buds of plants of the repressor lines are gently opened and emasculated by removing all stamens. The stigmas are then pollinated with pollen from plants of the repressor lines and pollinated buds are tagged and bagged. Once siliques formed, the bags are removed, and mature seeds are collected. Plants generated from these seeds are then used to determine the level of reporter gene (GUS) repression by GUS staining. Levels of GUS expression in the hybrid lines are compared to those of the original reporter lines. Plants showing a modified GUS expression levels are further characterized using PCR, Southern and Northern analysis.

Example 4

Preparation of a Chromatin Remodelling Factor

HDAC was used as an example of a chromatin remodelling factor that may be isolated from an organism. Transcription factors that recruit histone deacetylase (HDAC) to target promoters in *Brassica napus* were identified in vivo by screening a yeast two-hybrid library using the *Arabidopsis thaliana* HDA19 as bait. A cDNA clone that encodes a novel protein, bnKCP1, containing a kinase-inducible domain (KID) was identified. Southern blot analysis indicated that the bnKCP1 gene belongs to a small gene family of at, least three members, and northern blot analysis showed that it was strongly expressed in stems, flowers, roots and immature siliques seeds, but not in leaf blades. In vitro protein binding assays showed that the protein is able to interact with both HDA19 and histone acetyltransferase (HAT) and that the KID domain is required for this interaction with HDA19 and HAT in vitro. When assayed in vivo, bnKCP1 exerted modest activation of transcription of a reporter gene in yeast.

The cAMP-responsive element (CRE) binding protein (CREB) binds to the CREB-binding protein (CBP) in response to extracellular stimuli that induce intracellular accumulation of secondary messengers $Ca^{2+}$ and cAMP. The KID domain is highly conserved in the CREB family proteins, CREB, CREM and ATF-1 (Montminy, 1997). Each protein in this family has a serine phosphorylation site (RRP $\underline{S}^{133}$) within the KID domain, which is recognised by protein kinase A (PK-A) that phosphorylates $S^{133}$. PK-A in turn is induced by outside stimuli that induce intracellular accumulation of $Ca^{2+}$ and cAMP. CREB binding activity is regulated through $S^{133}$ phosphorylation, which leads to interaction of CREB with CBP. The KIX domain of CBP is required for interaction with the KID domain of CREB having a phosphorylated $S^{133}$ (see review Montminy, 1997). Interestingly, CBP possesses intrinsic HAT activity (Bannister and Kouzarides, 1996; Ogryzko et al., 1996) suggesting that recruitment of CBP to target promoters by the transcription activator CREB may contribute to the transcriptional activation of CRE-dependent genes by the involvement of histone acetylation at the genetic loci of target genes.

In *Arabidopsis*, a HAT gene encoding an ortholog of the yeast GCN5 was found to bind in vitro to two proteins similar to the yeast HAT-adaptor proteins ADA2, ADA2a and ADA2b (Stockinger et al., 2001). Moreover, the transcription activator CBF1 was found to bind to both HAT and ADA2, indicating that these proteins might be recruited to target cold-inducible genes by binding to CBF1 (Stockinger et al., 2001). The finding that the *Arabidopsis* ADA2 and GCN5 genes share similarity with their counterparts in yeast and humans suggests that chromatin remodelling complexes are conserved even among evolutionary distant organisms.

Experimental Procedures

*Brassica napus* L. cv Cascade (winter type), Westar (spring type) and DES010 (spring type) were used for the isolation of genomic DNA and total RNA. Leaves, flowers, stems, siliques and immature seeds were harvested from plants cultured in a controlled-environment greenhouse programmed for a photoperiod of 16 h day and 8 h night. Roots were obtained by culturing sterilized seeds in 0.8% agar plates containing ½ MS medium and 1% sucrose. For cold acclimation (4° C.), abscisic acid (250 µM), drought and high salt (850 mM NaCl) treatments, four-leaf stage seedlings were treated and fourth fully expanded leaf blades were harvested as described by Gao et al. (2002). LaCl3 and inomycin treatments were carried out by watering four-leaf stage plants with 20 mM $LaCl_3$ and 10 µM inomycin, respectively. Plants were covered with Saran Wrap to slow evaporation.

Yeast Two-hybrid Screening and Cloning

A yeast two-hybrid cDNA library (Dr. Isobel Parkin, Agriculture and Agri-Food Canada Research Centre, Saskatoon) was constructed from poly(A) mRNA isolated from the above-ground parts of the four-leaf stage seedlings of *B. napus* L. cv. DH12075 and cloned into a GAL4 AD (activation domain) vector pPC86 using the SuperScript Plasmid System for cDNA Synthesis and Plasmid Cloning (GibcoL BRL).

To generate the pDBLeu-HDA19 construct, the entire coding region of *Arabidopsis thaliana* RPD3-type HDA19 cDNA (Accession # AF195547) was PCR amplified using PWO DNA polymerase (Roche) with a forward primer:

```
                                       (SEQ ID NO: 44)
5'-GCGTCGACGATGGATACTGGCGGCAATTCGC-3'
``` and a reverse primer:

```
                                       (SEQ ID NO: 45)
5'-AGGCGGCCGCTTATGTTTTAGGAGGAAACGCC-3'.
```

The identity of the PCR product was confirmed by DNA sequence analysis and inserted into the SalI and NotI sites of the Gal4 DB (DNA binding domain) vector pDBLeu in-frame with the GAL4 sequence and used as a bait to screen the *B. napus* cDNA library using PROQUEST Two-Hybrid System (GibcoL BRL).

Approximately $1 \times 10^6$ transformants were subjected to the two-hybrid selection on synthetic complete (SC) medium lacking leucine, tryptophan and histidine but containing 15 mM 3-amino-1,2,4-triazole (3AT®). The expression of the HIS3 reporter gene allowed colonies to grow on the selective medium and the putative His+ (3AT®) positive transformants were tested for the induction of the two other reporter genes, URA3 and lacZ. The positive colonies were reassessed by retransformation assays and the cloned cDNAs were identified by PCR and DNA sequence analysis.

Southern Blot Analysis

Total genomic DNA was isolated from the leaves of *B. napus* L. cv Westar using a modified CTAB (cetyltriethylammonium bromide) extraction method (Gao et al., 2002). Briefly, 10 µg of total genomic DNA was digested with EcoRI, XbaI, HindIII, PstI, EcoRV and KpnI restriction endonucleases, separated on a 0.8% agarose gel, transferred to Hybond-XL membranes (Amersham Phamacia) and hybridized with the bnKCP1 open reading frame (ORF) labeled with [$\alpha$-$^{32}$P]dCTP using random primer labeling procedure. The DNA fragment to be used as a probe was isolated from a 0.8% agarose gel and purified with a QIAquick Gel Extraction Kit (Qiagen), and the probe was purified with a ProbeQuant G-50 Micro Column (Amersham Phamacia). Hybridization was performed under high stringency conditions (Gao, M.-J. et al., 2002).

Northern Blot Analysis

Total RNA was isolated from the tissues of *B. napus* L. cv DES010. These included leaves and stems of four-leaf stage seedlings, flowers, immature siliques of adult plants, and roots of cultured seedlings as described by Gao et al. (2001). Probe labelling, hybridization, washing and membrane stripping were performed as described above in the Southern blot analysis Section.

Expression and Purification of Recombinant Gcn5 and HDA19

The full coding regions of the *Arabidopsis* HAT, Gcn5 (Dr. M. Thomashow, Michigan State University, MI), and HDA19 (Accession #AF195547) were PCR amplified, sequence analyzed and inserted in-frame with the GST (glutathione s-transferase) into the SalI and NotI sites of vector pGEX-6P-2 (Amersham Pharmacia). The forward used for the amplification of Gcn5 was:

```
                                    (SEQ ID NO: 46)
5'-GCGTCGACGATGGACTCTCACTCTTCCCACC-3'
``` and the reverse primer for Gcn5 was:

```
                                    (SEQ ID NO: 47)
5'-GCGCGGCCGCCTATTGAGATTTAGCACCAGA-3'
```

The forward primer for HDA19 was SEQ ID NO: 44, as listed above, and the reverse primer was:

```
                                    (SEQ ID NO:48)
5'-GCGCGGCCGCTTATGTTTTAGGAGGAAACGC-3'.
```

Recombinant pGEX-6P-2 plasmids were used to transform *E. coli* BL21-CodonPlus (DE3)-RP competent cells (Stratagene). Expression and purification under non-denaturing conditions were carried out as described by Gao et al. (Gao, M.-J. et al., 2002). The GST-Gcn5 and GST-HDA19 fusion proteins were analyzed by 7.5% SDS-PAGE (SDS-polyacrylaride gel electrophoresis) and western blotting with rabbit anti-GST-Pi polyclonal antibody (Chemicon) using ECL Western blotting analysis system (Amersham Pharmacia).

Generation of Deletion Mutants of bnKCP1

The two fragments, bnKCP1$^{1-160}$ and bnKCP1$^{1-80}$, and the entire coding region of bnKCP1 DNA encoding amino acids 1-80, 1-160 and 1-215, respectively, were amplified by PCR and cloned into the HindIII and XhoI sites of pET-28-b vector (Novagen, Madison, Wis.). The primers used for the amplification were as follows:

```
bnKCP1^1-160 (240 bp):
forward primer:              (SEQ ID NO:49)
5'-GCAAGCTTATGGCAGGAGGAGGACCAACT-3', reverse primer:              (SEQ ID NO:50)
5'-CGCTCGAGCTCCTCCTCATCATTGTCTTC-3';

bnKCP1^1-180 (480 bp):
forward primer:              (SEQ ID NO:49)
5'-GCAAGCTTATGGCAGGAGGAGGACCAACT-3', reverse primer:              (SEQ ID NO:51)
5'-CGCTCGAGATGAACAGGCAAAAGAGGCAT-3';

bnKCP1 (645 bp):
forward primer:              (SEQ ID NO:49)
5'-GCAAGCTTATGGCAGGAGGAGGACCAACT-3',
```

```
reverse primer               (SEQ ID NO:52)
5'-CGCTCGAGCTCaTCTTCTTCTTCTTCTTC-3'.
```

In Vitro Protein Interaction Assays

Full-length bnKCP1 and truncated mutant bnKCP1$^{1-160}$ and bnKCP1$^{1-80}$ proteins labeled with [$^{35}$S]methionine were produced using TNT-Quick Coupled Transcription/Translation System (Promega) according to the manufacture's instructions, with some modifications. A total of 1 μl of RNase inhibitor (GibcoL BRL) and 1 μl of protease inhibitors set (Roche) were added to the lysate reaction. After incubation for 90 min at 30° C., RNase A was added to the reaction to a final concentration of 0.2 mg/ml and incubated for 5 min at the same temperature.

In vitro protein interaction was detected with GST pull-down affinity assays as described by Ahmad et al. (1999) with some modifications. Briefly, 6 μg of GST or 4 μg of GST-fusion protein was incubated with 5 μl of [$^{35}$S]Met-labeled translation mixture in 200 μl of bead-binding buffer (50 mM K-phosphate, pH 7.6, 450 mM KCl, 10 mM MgCl$_2$, 10% glycerol, 1% Triton X-100, 1% BSA and 1 μl of diluted 1:12 protease inhibitors set) for 1 h at room temperature. After incubation, 20 μl of 50% slurry of glutathione-Sepharose beads containing 10 mg/ml of BSA and 4 μg of EtBr was mixed with the reaction mixture followed by gentle rotation for 1 h at 4° C. After washing six times with 1.2 ml of bead-binding buffer without BSA and EtBr but containing 12 μl of protease inhibitors set (Roche), the bound proteins were eluted with 30 μl of 2×SDS loading buffer, boiled for 2 min and analyzed by 12% SDS-PAGE. After electrophoresis, the gels were dried, treated with Amplify (Amersham Pharmacia) and subjected to fluorography.

In Vivo Protein Assays

The entire region of bnKCP1 and the two fragments, bnKCP1$^{1-160}$ and bnKCP1$^{1-80}$, were PCR amplified and cloned into the SalI and NotI sites of pPC86 vector (GibcoL BRL) in-frame with the GAL4 AD sequences to generate constructs pPC86-bnKCP1, pPC86-bnKCP1$^{1-160}$ and pPC86-bnKCP1$^{1-80}$. The oligonucleotide primers used in PCR amplification were as follows:

```
bnKCP1, bnKCP1^1-160 and
bnKCP1^1-80 forward primer
                             (SEQ ID NO:53)
5'-GCGTCGACGATGGCAGGAGGAGGACCAACT-3' bnKCP1 reverse primer
                             (SEQ ID NO:54)
5'-GCGCGGCCGCCTCATCTTCTTCTTCTTCCTC-3' bnKCP1^1-160 reverse primer
                             (SEQ ID NO:55)
5'-GCGCGGCCGCATGAACAGGCAAAAGAGGCAT-3' bnKCP1^1-80 reverse primer
                             (SEQ ID NO:56)
5'-GCGCGGCCGCCTCCTCCTCATCATTGTCTTC-3'
```

For in vivo protein interaction assays, the MaV203 yeast cells carrying the reporter gene lacZ and the construct pDBLeu-HDA19, in which the HDA19 was fused in-frame with GAL4DB, were transfected with either of the plasmids pPC86-bnKCP1, pPC86-bnKCP1$^{1-160}$ and pPC86-bnKCP1$^{1-80}$ or the vector alone. The expression of lacZ reporter gene was quantified by measuring the β-galactosidase activity using chlorophenol red-β-D-galactopyranoside (CPRG) according to the manufacturer's instructions (GibcoL BRL). Two yeast control strains A and B (GibcoL BRL) were used as negative and positive controls, respectively.

Site-Directed Mutagenesis (SDM)

The QuickChange site-directed mutagenesis kit (Stratagene) was used to replace the serine residue in the PK-A phosphorylation site (RRPS$^{188}$) within the KID domain with a glycine residue to generate bnKCP1G$^{188}$ according to the manufacturer's instructions. The two oligonucleotide primers used in SDM were as follows:

```
                                       (SEQ ID NO:57)
forward primer:
5'-GATGTTCTTGCGAGGAGACCAGGATTCAAGAACAGAGCATTGAAG-
3'

(SEQ ID NO:58)
reverse primer:
5'-CTTCAATGCTCTGTTCTTGAATCCTGGTCTCCTCGCAAGAACATC-
3'
```

The introduced mutation was confirmed by DNA sequencing, and the mutated bnKCP1G$^{188}$ was cloned into the HindIII and XhoI sites of pET-28b vector to generate pET-bnKCP1G$^{188}$, which was then used for in vitro protein interaction assays as described above.

Transactivation Assay Using Yeast One-Hybrid System

Effector plasmids pDBLeu-bnKCP1$^{1-160}$, pDBLeu-bnKCP1$^{1-80}$, pDBLeu-bnKCP1$^{81-215}$ and pDBLeu-bnKCP1 were constructed by ligating the PCR-amplified fragments ΔbnKCP1$^{1-160}$, ΔbnKCP1$^{1-80}$, ΔbnKCP1$^{81-215}$ and the coding region of bnKCP1 into the SalI/NotI sites of pDBLeu vector (GibcoL BRL) in-frame with the GAL4 DB sequence. The oligonucleotide primers for PCR amplification were as follows:

```
bnKCP1 forward primer
                                       (SEQ ID NO:53)
5'-GCGTCGACGATGGCAGGAGGAGGACCAACT-3', bnKCP1 reverse primer
                                       (SEQ ID NO:54)
5'-GCGCGGCCGCCTCATCTTCTTCTTCTTCCTC-3' bnKCP1$^{1-160}$ forward primer
                                       (SEQ ID NO:53)
5'-GCGTCGACGATGGCAGGAGGAGGACCAACT-3', bnKCP1$^{1-160}$ reverse primer
                                       (SEQ ID NO:55)
5'-GCGCGGCCGCATGAACAGGCAAAAGAGGCAT-3' bnKCP1$^{1-80}$ forward primer
                                       (SEQ ID NO:53)
5'-GCGTCGACGATGGCAGGAGGAGGACCAACT-3', bnKCP1$^{1-80}$ reverse primer
                                       (SEQ ID NO:56)
5'-GCGCGGCCGCCTCCTCCTCATCATTGTCTTC-3' bnKCP1$^{81-215}$ forward primer
                                       (SEQ ID NO:59)
5'-GCGTCGACGCTAGGGTTGGCTTCATTGAGA-3' bnKCP1$^{81-215}$ reverse primer
                                       (SEQ ID NO:54)
5'-GCGCGGCCGCCTCATCTTCTTCTTCTTCCTC-3'
```

The three reporter genes, lacZ, HIS3 and URA3, which were chromosomally integrated in the genome of MaV203 yeast cells were driven by unrelated promoters containing GAL4 DNA binding sites (GibcoL BRL). For transient assays, the effector constructs or the negative control vector pDBLeu were transferred to the MaV203 yeast cells. The β-galactosidase activity was measured using CPRG (chlorophenol red-β-D-galactopyranoside) according to the manufacturer's instructions (GibcoL BRL). The MaV203 cells containing plasmids pDBLeu-HDA19 and pPC86-bnKCP1 were used as the positive control. In addition, we used three yeast control strains A, B, and C (GibcoL BRL), which were developed to contain plasmid pairs expressing fusion proteins with none, weak and moderately strong protein-protein interaction strength, respectively.

Transient Expression of the GUS-bnCKP1 Fusion Protein

The oligonucleotide primers for PCR amplification of the entire coding region of bnKCP1 were as follows:

```
                                       (SEQ ID NO:60)
    forward primer
    5'-GCGAATTCATGGCAGGAGGAGGACCAACT-3', (SEQ ID NO:61)
    reverse primer
    5'-CGGAGCTCCTCaTCTTCTTCTTCTTCTTC-3'.
```

The amplified sequence was cloned into the EcoRI and ScaI sites of the binary vector p79-637, a derivative of the vector CB301, to generate construct p77-132, which contains GUS-bnKCP1 fusion under control of the CaMV35S promoter. The onion epidermal layers were transformed with *Agrobacterium* culture prepared as described by Kapila et al (1997) with a few modifications. Briefly, the onion inner epidermal layers were peeled, placed into a culture of *Agrobacterium tumefaciens* strain GV3101 pMP90 containing either p79-637, for GUS expression only, or p77-132 and subjected to continuous vacuum of −85 IPA for 20 min. After incubation at 22° C. under 16 h light condition for 7 days the tissues were placed into GUS staining solution [100 mM potassium phosphate buffer (pH 7.4), 1 mM EDTA, 0.5 mM $K_3Fe(CN)_6$, 0.5 mM $K_4Fe(CN)_6$, 0.1% Triton X-100, 1 mM 5-bromo-4-chloro-3-indolyl-β-D-glucuronide (X-gluc)], vacuum infiltrated for 20 min at −85 kPa and incubated overnight at 37° C. To determine the intercellular location of nuclei, tissues were stained with the nucleus-specific 4',6-diamidino-2-phenylindole (DAPI) solution (14 μg/ml DAPI, 0.1× PBS, 90% glycerol) (Varagona et al, 1991) and viewed under a Zeiss microscope using both fluorescence and bright-field optics.

Cloning of the *B. napus* KCP Protein

To identify proteins that interact with HDA19 in *B. napus*, the ORF of *Arabidopsis* HDA19 fused to the yeast Gal4 DNA binding domain was used as bait in a yeast two-hybrid screening of a *B. napus* cDNA library linked to the yeast Gal4 activation domain. Several positive clones were obtained on the basis of the induction of three yeast reporter genes, HIS3, URA3 and lacZ and DNA sequence analysis. One of these clones (963 bp), pPC86-bnKCP1, encodes a 23.5 kDa protein that contains a putative kinase-inducible domain (KID)-like motif, and hence was designated bnKCP1 (*B. napus* KID-containing protein 1).

Alignment of deduced amino acid sequences indicated that bnKCP1 shares an 82% amino acid identity with atKCP, an *Arabidopsis* unknown 26.6 kDa protein (AY088175, At5g24890). It also shares high similarity in the conserved region of approximately 55 amino acids (GKSKS domain) with other two other atKCP-like Arabidopsis unknown proteins, atKCL1 (CAB45910, At4g31510) and atKCL2 (AAD23890, At2g24550) (FIG. 10A).

Figure 12:
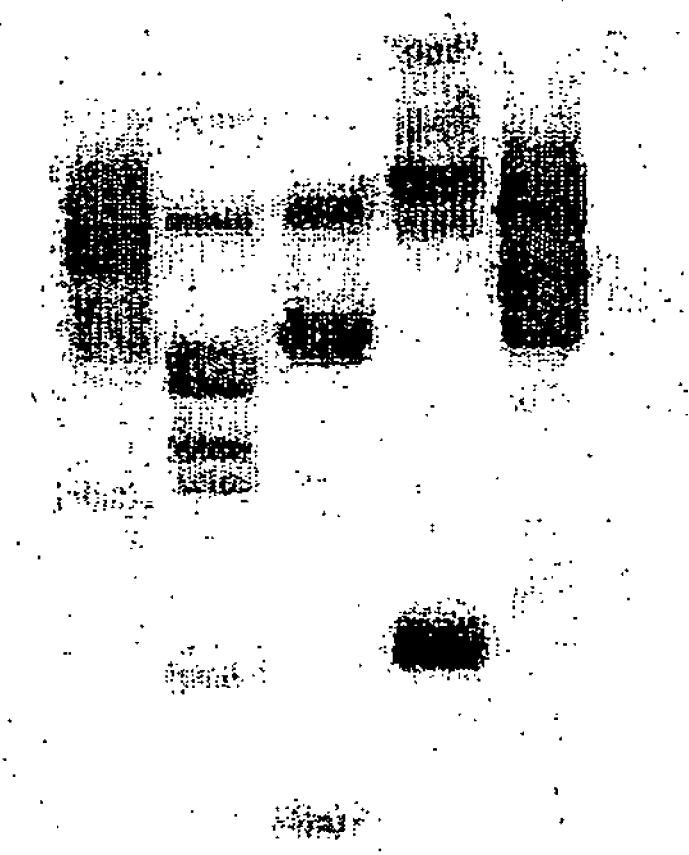
FIG. 12 shows Southern blot analysis of Brassica genomic DNA. Total genomic DNA (10 µg/lane) from Brassica napus cv Westar was digested with restriction enzymes EcoRI (EI), XbaI (X), HindIII (H), PstI (P), EcoRV (EV) and KpnI (K). The entire ORF of bnKCP1 was used as a probe.

To estimate the bnKCP1 gene copy number in *Brassica napus* we carried out Southern blot analysis on of total genomic DNA digested with restriction endonucleases using the entire open reading frame of bnKCP1 for probing under high stringency conditions (FIG. 12). Digestion with EcoRI (EI), HindIII (H), PstI (P), EcoRV (EV) and KpnI, none of which has a cutting site within bnKCP1, resulted in the detection of three bands, whereas digestion with XbaI generated six bands, because of the existence of an internal cutting site for XbaI in the bnKCP1 gene. This result indicates that bnKCP1 belongs to a small gene family of three members in the *Brassica napus* genomes.

Structural Features of the bnKCP1 Protein

Figure 11:
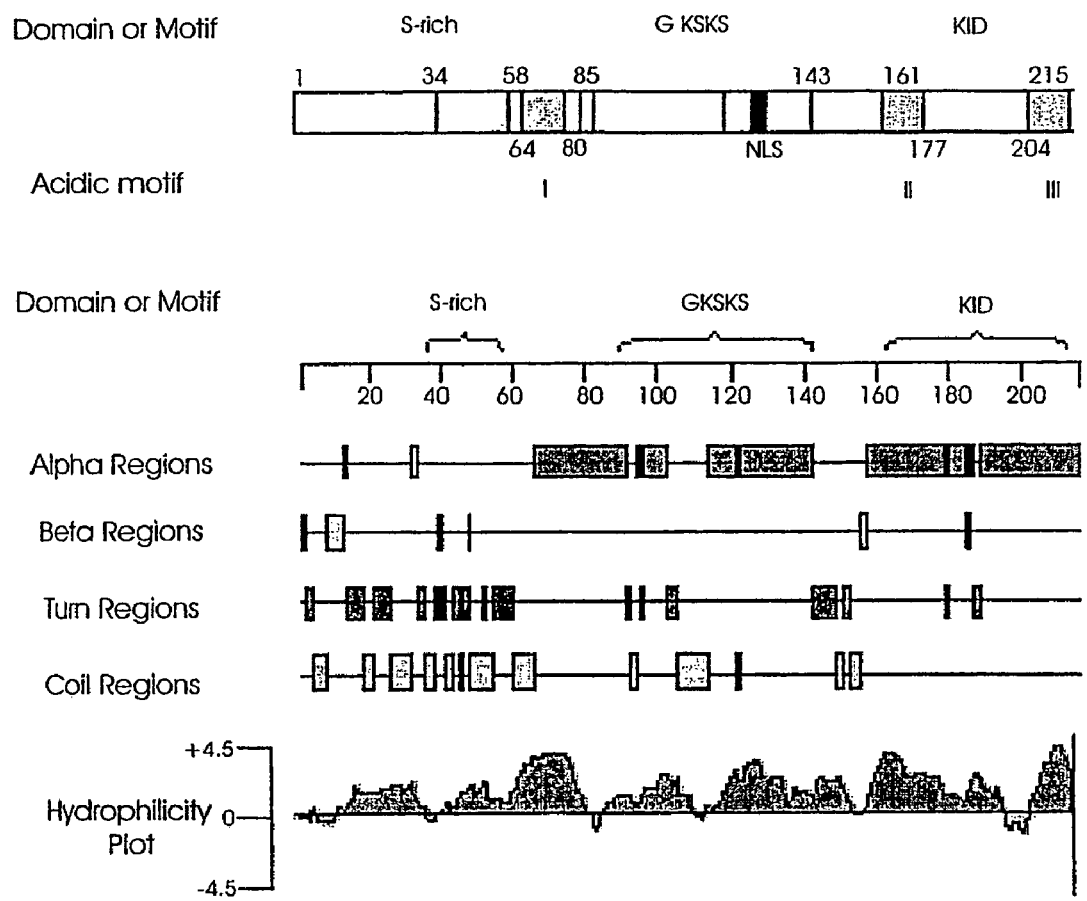
FIG. 11 shows structural features of bnKCP1.

The ORF of bnKCP1 gene codes for a 215 amino acid polypeptide product of polypeptide with several functional motifs (FIG. 11). Based on a search of protein localization sites using PSORT program (see URL:psort.nibb.acjp; Nakai and Kanehisa, 1992), bnKCP1 appears to be is a nuclear protein containing a pat7 nuclear localization signal (NLS) PLNKKRR (SEQ ID NO: 62; FIG. 10A, residues 127-133). Three acidic motifs (I, II and III) aid a serine-rich (S- rich) region (residues 34-58) may function in transcription activation by bnKCP1 (Johnson et al., 1993). The charged motif GKSKS (residues 88-143), which is conserved in all four protein orthologs (FIG. 10A), is rich in basic residues and encompasses the NLS. This suggests that this domain serve the may function of a DNA-binding motif (FIG. 11). In addition, bnKCP1 is extremely hydrophilic (FIG. 11) suggesting bnKCP 1 is an active element in the nuclear matrix.

Amino acid sequence analysis also revealed that bnKCP1 has a KID-like motif (residues 161-215, FIG. 10A) with alpha structure at its C-terminal region (FIG. 11). The KID is highly conserved in mammalian CREB protein family and functions in transactivation and protein binding (Montminy et al., 1997). The KID in bnKCP1 has a high similarity to the CREB family member ATF-1 (FIG. 10B, C) and contains a protein kinase A (PK-A) phosphorylation site (RRPS) that is conserved in the CREB family of proteins (FIG. 10B).

Interaction of bnKCP1 with HDA19 and Gcn5

To confirm the interaction detected in the yeast two-hybrid system between the bnKCP1 protein and HDA19, GST pull-down assays were performed using in vitro translated bnKCP1 labeled with [$^{35}$S]Methionine. The bnKCP1 protein was tested for its ability to interact with recombinant GST-HDA19 or GST-GcnS fusions expressed in *E. coli*.

As shown in FIG. 13B, bnKCP1 bound to both GST-HDA19 and GST-Gcn5 fusion proteins, but not to GST alone. To reassess the interaction of bnKCP1 with Gcn5 in vivo, the ORF of the *Arabidopsis* Gcn5 was fused to the yeast Gal4 DNA binding domain in pDBLeu vector and then used to transform yeast MaV203 cells expressing bnKCP1 fused to the yeast Gal4 activation domain in pPC86 vector. The transformants showed induction of the three reporter genes, HIS3, URA3 and lacZ at a relatively lower level when compared with the induction levels in transformants with bnKCP1 and HDA19 (data not shown). This result suggests that bnKCP1 has a preference for binding to HDA19 in vivo.

To map the protein binding domain of the bnKCP1 protein, two C-terminal truncated mutants of bnKCP1 lacking the KID domain were constructed. These are ΔbnKCP1$^{1-160}$ (residues 1-160) and ΔbnKCP1$^{1-80}$ (residues 1-80) as shown in FIG. 13A. These truncated mutants were assayed for, in vitro interaction with the recombinant GST-HDA19 or GST-Gcn5 fusion proteins. The two mutant proteins, ΔbnKCP1$^{1-}$$_{160}$ and ΔbnKCP1$^{1-160}$, exhibited no interaction with either GST-HDA19 or GST-Gcn5 indicating that the KID domain of bnKCP1 protein is essential for binding to HDA19 and Gcn5.

The importance of the KID domain for protein binding was also determined in vivo using the yeast two-hybrid system. MaV203 yeast cells were co-transformed with pDBLeu-HDA19, and either pPC86-bnKCP1, pPC86-bnKCP1$^{1-160}$, pPC86-bnKCP1$^{1-80}$ or pPC86 alone (FIG. 13C). β-galactosidase activity was reduced by at least 50% when pDBLeu-expressing cells were transformed with plasmids expressing either ΔbnKCP1$^{1-160}$ or ΔbnKCP1$^{1-80}$, both of which lacked KID, as compared to the full-length bnKCP1. This finding demonstrates that KID is critical for bnKCP1 interaction with HDA19 in vivo.

Figures 14, 14A, 14B:
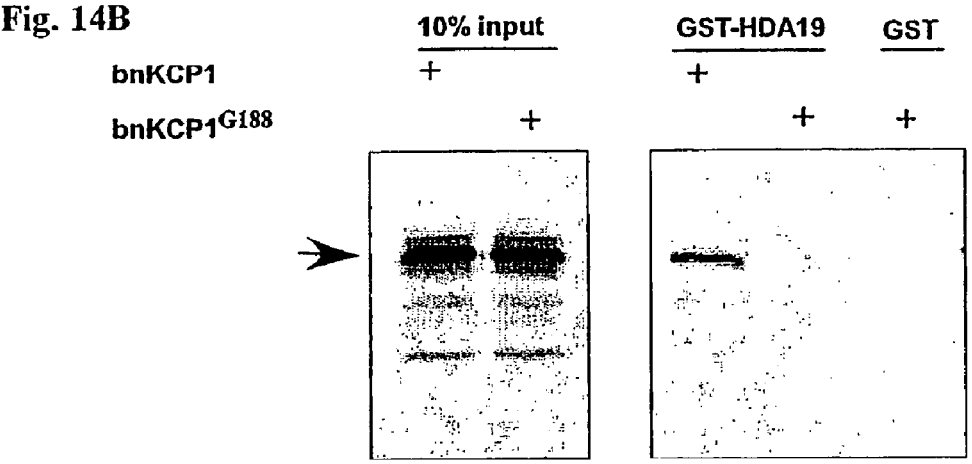
FIG. 14 shows the effect of S$^{188}$ on the interaction between bnKCP1 and GST-HDA19 fusion protein. A glycine residue (G$^{188}$) was introduced by site-directed mutagenesis to replace S$^{188}$. The binding activities of wild-type bnKCP1 and the mutant ΔbnKCP1$^{188}$ with GST-HDA19 or GST alone (negative control) were examined with GST pulldown affinity assay as described in Example 4.
FIG. 14A shows the introduction of G188 into the KID of bnKCP1.
FIG. 14B shows in vitro protein interaction of bnKCP1 and the mutant ΔbnKCP1G$^{188}$ with GST-HDA19 or GST alone.

To investigate the importance of S$^{188}$ for bnKCP1 interaction with HDA19, the S$^{188}$ residue in bnKCP1 was mutated to G$^{188}$ using site-directed mutagenesis to obtain bnKCPG$^{188}$ protein (FIG. 14). This mutated protein was then tested for binding to HDA19 in vitro. When compared to bnKCP1, the mutated protein, bnKCPG$^{188}$, has significantly reduced binding to HDA19 (FIG. 14). This confirms that S$^{188}$ is essential for optimal interaction between bnKCP1 and HDA19.

Expression Pattern of the bnKCP1 Gene

Figure 15:
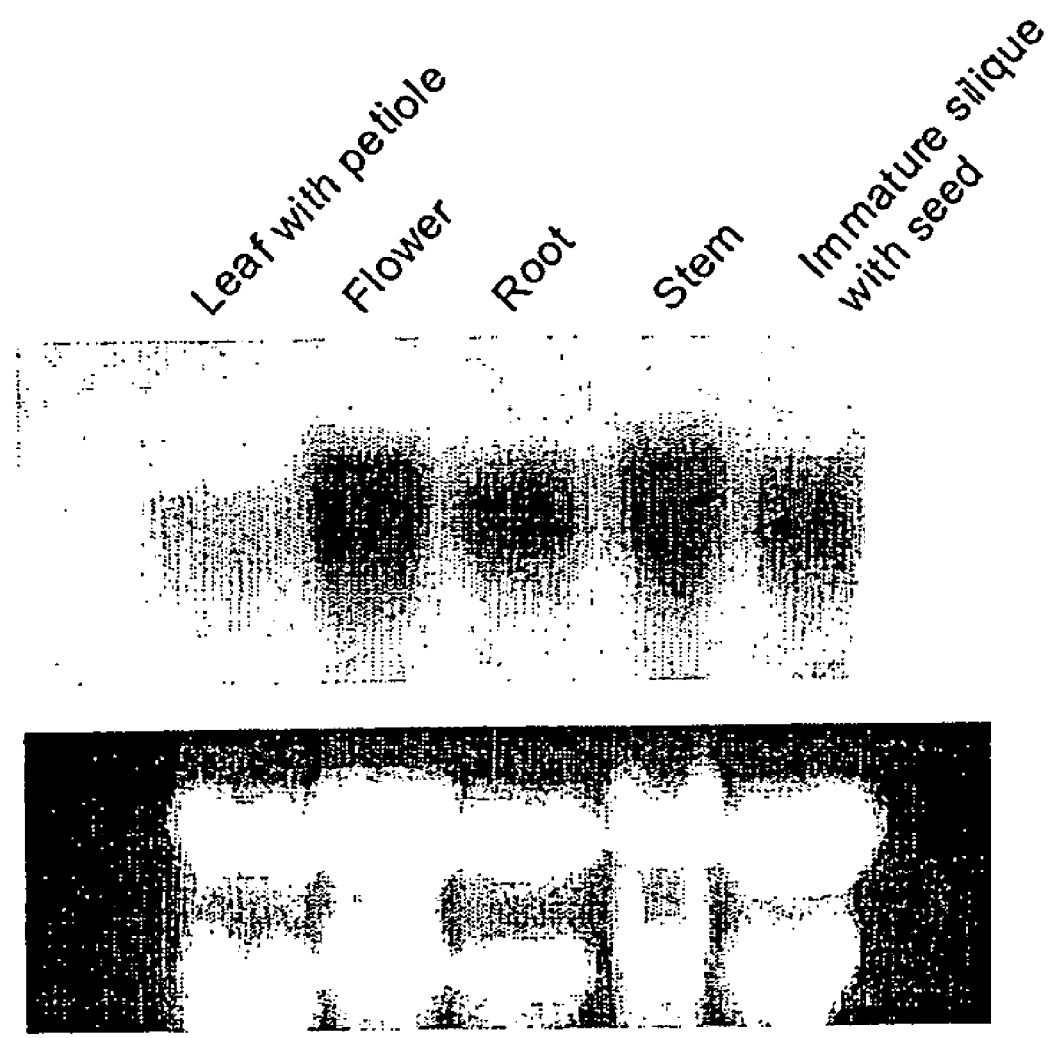
FIG. 15 shows expression patterns of bnKCP1 mRNA in different tissues. Total RNA (20 µg/lane) was isolated from leaves with petioles, flowers, roots, stems and immature siliques.
Figure 19:
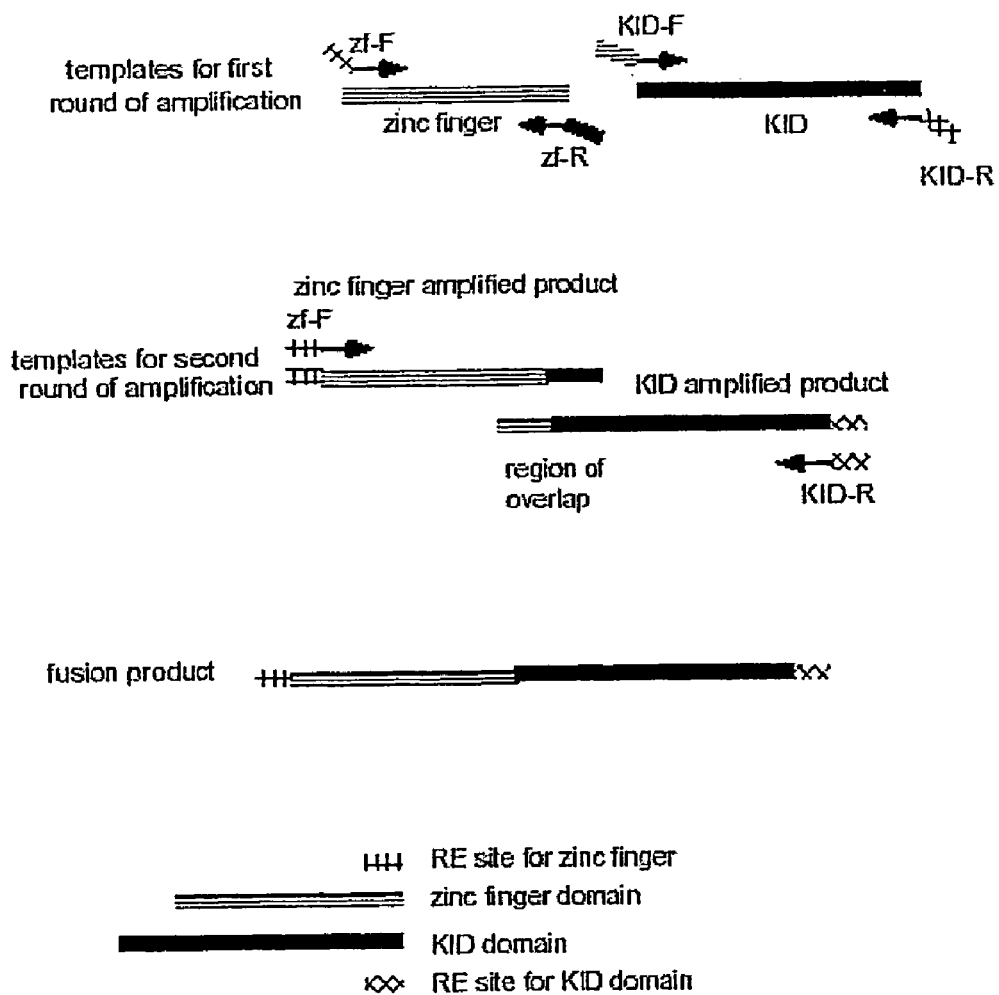
FIG. 19 shows a diagrammatic representation of a strategy for preparing fusions between a recruitment factor involved in chromatin remodelling and a DNA binding protein. In the non-limiting example shown in this figure, the recruitment factor is KID (see Example 4), and the DNA binding protein is a zinc finger.

The expression pattern of the bnKCP1 gene was analyzed by Northern blot analysis of total RNA extracted from various organs of *B. napus*. As shown in FIG. 15, two transcripts of similar sizes appear to hybridize to bnKCP1, indicating the existence of two homologs of bnKCP1 mRNAs in *B. napus*. These transcripts accumulated at high levels in flowers, roots, stems and immature siliques, and at low levels in leaves with petioles, but were undetectable in leaf blades (FIGS. 15, 16).

To investigate the pattern of bnKCP1 expression in response to environmental stress conditions, total RNA was isolated from leaf blades of four-leaf stage *B napus* seedlings that were exposed to low temperature (4° C.), drought, high salt (NaCl), and ABA treatment, and used for northern blot analysis using a bnKCP1 probe. Transcripts of both bnKCP1 homologs accumulated in leaves in response to cold treatment. The lower size (~0.9 kb) transcript appears to be induced within 4 h of cold treatment and about 4 h earlier than the higher molecular weight (1.1 kb) one (FIG. 16A). The bnKCP1 transcript appears to accumulate in response to low temperature (4° C.), but expression was not detected in leaf blades of plants grown under drought condition for up to 4 days, high salt stress for up to 11 days, or upon exogenous application of ABA for up to 8 hours (data not shown). Expression of bnKCP1 in the stems, was repressed upon cold treatment (FIG. 16A), suggesting the response of bnKCP1 transcript to low temperature or the recruitment of HDA19 and HAT to the promoters of cold responsive genes is organ specific.

Since cold acclimation is known to be associated with elevated levels of intracellular concentrations of Ca$^{2+}$, tests to determine whether Ca$^{+2}$ has any effect on bnKCP1 expression were performed. Northern blot analysis was performed using total RNA isolated from leaves of seedlings treated with Ca$^{2+}$ channel blocker LaCl$_3$ and the Ca$^{2+}$ ionophore inomycin at room temperature. Induction of bnKCP1 expression upon treatment with inomycin was rapid (2 hrs) but short-lived. The bnKCP1 transcript was undetectable in leaves of seedlings treated with the LaCl$_3$ (FIG. 16B).

Transcription Activation by bnKCP1

To determine whether bnKCP1 functions as a transcription activator, transactivation experiments were carried out in yeast. A yeast strain carrying three reporter genes, lacZ, HIS3 and URA3, driven by promoters fused to GAL4 DNA binding sites and independently integrated into the yeast genome were transfected with the effector plasmid pDBLeu-bnKCP1 comprising bnKCP1 fused to the GAL4 DB under the control of ADH promoter. The effector stimulated β-galactosidase activity about 8-fold relative to either GAL4 DB alone or yeast control strain A that contains plasmid pairs expressing fusion proteins without protein-protein interaction. A similar result was obtained when the yeast cells were co-transformed with the positive control plasmids pDBLeu-HDA19 and pPC86-bnKCP1 identified by the two-hybrid selection (FIG. 17A). Reporter genes HIS3 and URA3 were also modestly activated by bnKCP1 (data not shown). Based on these findings, it can be concluded that bnKCP1 exerts transactivation of target genes in Brassica napus.

These data demonstrate the isolation of a plant protein that contains a putative KID domain, which interacts with both GCN5 (HAT) and HDA19. bnKCP1 was highly expressed in all organs tested, except leaf blades, where it was induced in response to cold acclimation, which also resulted in repressing its expression in stems. Furthermore, bnKCP1 exerts transcription activation of a reporter gene when tested in yeast, indicating the function of bnKCP1 as a transcription factor.

To map the transactivation domain of the bnKCPP1 protein, one N-terminal truncated mutant of bnKCP1, $\Delta bnKCP1^{81-215}$, and two C-terminal truncated mutants, $\Delta bnKCP1^{1-160}$ and $\Delta bnKCP1^{1-80}$ (FIG. 17B) were generated and used in in vivo transactivation assays in yeast. As shown in FIG. 17C, deletion of the KID or GKSKS domains had no significant influence on β-galactosidase activity, whereas deletion of the N-terminus resulted in approximately 65% reduction in β-galactosidase activity.

Nuclear Localization of the bnKCP1 Protein

Structural and functional analyses showed bnKCP1 to have features typical of transcription factors. To confirm that bnKCP1 is a nuclear proteins, onion epidermal cell layers were transformed with constructs for the expression of either a GUS-bnKCP1 fusion or GUS alone (FIG. 18). Using an Agrobacterium-mediated transformation method (Kapila et al, 1997). As shown in FIG. 18, GUS activity was visualized exclusively in the cytoplasm of control onion cell layers. In contrast, a blue precipitate was localized in the nuclei of cell layers transformed with GUS-bnKCP1 fusion construct, although there was still a certain amount of cytoplasm staining, indicating that at least some targeting to the nucleus occurs with the fusion protein.

Expression of bnKCP1 is Organ-Specific

The bnKCP1 gene appears to be part of a multigene family of three members based on Southern blot hybridization. Northern blot analyses showed that two members of this gene family are of similar transcript sizes and expression patterns. This is consistent with information about bnKCP1 orthologs in Arabidopsis, where there are one atKCP (At5g24890) and two atKCP-like members (At4g31510 and At2g24550) of similar sizes ranging from 1 kb to 1.2 kb. Northern blot analysis revealed that bnKCP1 mRNA was expressed in flowers, roots, stems and immature siliques (FIG. 14). The transcript accumulation, however, was undetectable in leaf blades of B. napus seedlings, suggesting tissue/organ-specific expression of the bnKCP1 gene. However, cold treatment induced bnKCP1 expression in leaves, but repressed it in stems.

The KID Domain is Conserved in bnKCP1

Structural analysis of the bnKCP1 protein revealed that it was a strongly hydrophilic protein (23.5 kDa, pI 4.2) and had characteristic features of a transcription factor, including a putative nuclear localization signal (NLS), a putative basic DNA binding domain, putative acidic activation domains and a protein-protein interaction domain.

An important structural feature of bnKCP1 is the presence of a putative kinase-inducible domain (KID) with alpha secondary structure at the C-terminal region. The KID domain was first identified in mammalian CREB family members CREB, CREM and ATF-1. The KID domain in mammalian CREB is involved in at least two functions, interaction with CBP/p300 and the site for protein kinase A (PK-A) phosphorylation of $S^{133}$ (Montminy et al., 1997; Gonzalez et al., 1991; Quinn, 1993; Chrivia et al., 1993; Shaywitz et al., 2000). Similar to its counterpart in CREB, which is involved in protein binding, the KID domain of bnKCP1 is required for binding to both HDA19 and GCN5 in vitro and in vivo. The ability of bnKCP1 to interact with HDA19 indicates that bnKCP1-mediated transcription control requires direct or indirect recruitment of these transcription regulators to promoter regions of target genes regulated by bnKCP1.

Phosphorylation of CREB at $Ser^{133}$ is required for the interaction of CREB via its KID with CBP and for CREB to activate transcription in response to some extracellular stimuli (Gonzalez et al, 1989; Chrivia et al., 1993). The KID domain in bnKCP1 also contains a putative PK-A phosphorylation site ($RRPS^{188}$), which corresponds to the $RRPS^{133}$ in mammalian CREB.

Intracellular Level of $Ca^{+2}$ Affect bnKCP1 Expression

In mammalian cells, outside stimuli that increase intracellular concentrations of $Ca^{2+}$ or cAMP induce the expression of not only PK-A, but also the CREB gene (Meyer et al., 1993). Therefore, tests to determine whether conditions that increase intracellular concentrations of $Ca^{2+}$ would induce bnKCP1 expression were done. B. napus seedlings were subjected to one of two treatments, cold or inomycin. Cold acclimation is known to increase intracellular $Ca^{2+}$ concentrations (Monroy and Dhindsa, 1995; Knight et al., 1996), and inomycin is a known calcium ionophore that increases $Ca^{2+}$ influx (Hurley et al., 1996). These treatments resulted in the induction of bnKCP1 expression to varying degrees (FIG. 16), which indicated that bnKCP1 is induced by high intracellular $Ca^{+2}$ concentrations.

These results suggest a molecular mechanism by which bnKCP1 functions as a transcription factor to regulate gene expression by recruiting HDAC to the promoter regions of target genes.

Example 5

Characterization of the Recruitment Factor SCL1 and its Interaction with the Chromatin Remodelling Factor HDA19

To search for transcription factors additional that recruit histone deacetylase (HDAC) to target promoters in Brassica napus, a yeast two-hybrid library was screened using the Arabidopsis thaliana HDA19 as bait. This screening resulted in the isolation of a cDNA clone that encodes a SCARE-CROW-like protein, BnSCL1, which contains a number of putative functional motifs typical of the GRAS family of transcription factors. Southern blot analysis indicated that the BnSCL1 gene belongs to a small gene family of about three members. In vitro and in vivo protein interaction assays revealed that BnSCL1 interacts physically with HDA19 through the VHIID domain. BnSCL1 also exerted strong transactivation of the lacZ reporter gene in yeast, and both N- and C-terminal regions are critical for the transient expression. Quantitative RT-PCR and RNA gel blot analysis showed that BnSCL1 was expressed at relatively high level in roots, moderate level in flowers, weak in mature leaves and stems, and barely detectable in immature siliques. The accumulation of BnSCL1 transcript was regulated by 2,4-D in shoots, roots and matured leaves. Furthermore, the response of BnSCL1 to 2,4-D was modulated by histone deacetylase HDA19. These results strongly suggest a molecular mechanism by which BnSCL1 functions as a transcription factor to regulate gene expression by recruiting HDAC to the promoter regions of auxin-responsive genes.

Plant Materials

*Brassica napus* L. cv. DH12075 was used for DNA and total RNA isolation. Leaves, flowers, stems, siliques and immature seeds were harvested from plants cultured in a controlled-environment greenhouse programmed for a photoperiod of 16 h day and 8 h night. Roots were obtained by culturing sterilized seeds in 0.8% agar plates containing ½ MS medium (Murashige and Skoog, 1962) and 1% sucrose.

Tissue Treatment

In exogenous applied auxin treatments, four-leaf stage seedlings grown at 20° C. were treated with a foliar spray containing 1 mM 2,4-D and 50 mM sodium phosphate, pH 7.5. The four leaves were collected at 30 min, 60 min and 180 min after the first foliar application of 2,4-D. For the measurement of response of shoots and roots to auxin, sterilized seeds were germinated on plates in a growth chamber with continuous light at 20° C., and 10 dpg seedlings were supplied with varied concentration of 2,4-D. In the auxin transport inhibition experiments, 9 dpg seedlings were incubated in the medium supplemented with 50 µM NPA dissolved in 0.1% DMSO for 24 h before the 2,4-D treatment. For the HDAC inhibitor treatments, 10 mM sodium butyrate was added onto the growth medium and incubated for 24 h followed by exogenous 2,4-D application at varied concentrations.

Yeast Two-Hybrid Screening and Cloning

A yeast two-hybrid cDNA library was constructed from seedlings of *B. napus* L. cv. DH12075 and screened using a *Arabidopsis thaliana* RPD3-type HDAC (HDA19) as bait, with the methods of PROQUEST Two-Hybrid System (GibcoL-BRL) as previously described by Gao et al. (2003). The positive colonies were reassessed with retransformation experiments and confirmed with in vitro protein interaction assays, and the cloned cDNAs were identified by PCR and DNA sequence analysis.

Gel Blot Analysis

Total genomic DNA was extracted from the leaves of four-leaf stage *B. napus* using a modified CTAB (cetyltriethylammonium bromide) extraction method, and DNA gel blots were prepared and hybridized with the BnSCL1 open reading frame labeled with [$\alpha$-$^{32}$P]dCTP using random primer labeling procedure as described by Gao et al. (2003). Total RNA was isolated using hot phenol method with the first extraction for 30 sec at 80° C. as previously described (Gao et al. 2002). RNA was isolated from various tissues, including leaves and stems of four-leaf stage seedlings, flowers, immature seeds and siliques of adult plants, and roots of cultured seedlings.

Quantitative RT-PCR

Total RNA extracted as described above was treated with Amplification Grade Deoxyribonuclease I (GibcoL BRL) following the manufacture's instructions. The RNA samples were then directly used for reverse transcription prior to amplification without purification. The RT-PCR was quantitatively performed and completed in a one-step reaction using Superscript One-Step RT-PCR System (GibcoL BRL) as described by Gao et al. (2002). Gene-specific sense and anti-sense primers used to generate a 960 bp fragment of *Brassica napus* Actin, as an internal standard, were as described in Gao et al., (2002). Gene-specific primers for the generation of BnSCL1, BnIAA1 and BnIAA12 fragments were as follows:

```
BnSCL1 (435 bp)
                                    (SEQ ID NO:84)
  sense: 5'-GATGGACGAACATGCCATGCGTTCCA-3'
                                    (SEQ ID NO:85)
  anti-sense: 5'-CGCTCGGATCTTCTGAACAAT-3'

BnIAA1 (537 bp)
                                    (SEQ ID NO:86)
  sense: 5'-CCACGCGTCCGGTACGATGAT-3'
                                    (SEQ ID NO:87)
  anti-sense: 5'-GAAGTTGAGAAATGGTTTATGA-3'

BnIAA12 (659 bp)
                                    (SEQ ID NO:88)
  sense: 5'-ACGCTGGTGCTTCTCCTCCTC-3'
                                    (SEQ ID NO:89)
  anti-sense: 5'-AAAACCCATTAGAAGAACCAAGAA-3'
```

BnIAA1 and BnIAA12 are clones ML2798 and ML4744, which are homologs of *Arabidopsis* IAA1 and IAA12, respectively, and were identified in a database of *Brassica napus* ESTs that were generated at the Saskatoon Research Centre of Agriculture and Agri-Food Canada (see URL:.brassica.ca).

Expression and Purification of Recombinant HDA19

The open reading frame (ORF) of the HDA19 was PCR amplified, sequence analyzed, inserted in-frame with the GST (glutathione s-transferase) into the vector pGEX-6P-2 (Amersham Pharmacia), and transformed into *E. coli* BL21-CodonPlus (DE3)-RP competent cells (Stratagene) as previously described (Gao et al., 2003). The recombinant HDA19 protein was expressed and purified under non-denaturing conditions as described by Gao et al, 2002). The GST-HDA19 fusion protein was analyzed by western blotting with rabbit anti-GST-Pi polyclonal antibody (Chemicon) using ECL Western blotting analysis system (Amersham Pharmacia).

In Vitro Protein Interaction Assays

The entire coding region of BnSCL1 and four fragments, BnSCL1$^{1-358}$, BnSCL1$^{1-261}$, BnSCL1$^{1-217}$, and BnSCL1$^{1-145}$ encoding amino acids 1-434, 1-358, 1-261 and 1-217, respectively, were amplified by PCR and cloned into the HindIII and XhoI sites of the expression vector pET-28b (Novagen) in-frame with the His-Tag sequence. The primers used for amplification were as follows:

```
Forward primer for BnSCL1, BnSCL1^(1-358),
BnSCL1^(1-261), BnSCL1^(1-217) and BnSCL1^(1-145):
                                    (SEQ ID NO:90)
  5'-GCAAGCTTATGGACGAACATGCCATGCGTTCCA-3'

Reverse primer for BnSCL1:
                                    (SEQ ID NO:91)
  5'-CGCTCGAGAAAGCGCCACGCTGACGTGGC-3'

Reverse primer for BnSCL1^(1-358):
                                    (SEQ ID NO:92)
  5'-CGCTCGAGCGCGGAGATCTtCGGACGTAA-3'

Reverse primer for BnSCL1^(1-261):
                                    (SEQ ID NO:93)
  5'-CGCTCGAGCCTAATCGCCTTGAAAGATAA-3'

Reverse primer for BnSCL1^(1-217):
```

```
                                           -continued
                                                       (SEQ ID NO:94)
    5'-CGCTCGAGCGCCACAACCGCCGTGACTCT-3'

Reverse primer for BnSCL1¹⁻¹⁴⁵:
                                                       (SEQ ID NO:95)
    5'-CGCTCGAGCGCTCGGATCTTCTGAACAAT-3'.
```

The TNT-Quick Coupled Transcription/Translation System (Promega) was used to produce the full-length BnSCL1 protein and the truncated mutants ΔBnSCL1$^{1-358}$, ΔBnSCL1$^{1-261}$, ΔBnSCL1$^{1-217}$ and ΔBnSCL1$^{1-145}$ labeled with [$^{35}$S]methionine as previously described (Gao et al., 2003). In vitro protein interaction was detected with GST pulldown affinity assays as described by Ahmad et al. (1999) and Gao et al., (2003).

In Vivo Protein Interaction Assays

The six DNA fragments, BnSCL1$^{1-358}$, BnSCL1$^{1-261}$, BnSCL1$^{1-217}$, BnSCL1$^{1-145}$, BnSCL1$^{146-358}$ and BnSCL1$^{218-438}$ and the ORF of BnSCL1 encoding amino acids 1-358, 1-261, 1-217, 1-415, 146-358, 218-434 and 1434, respectively, were PCR amplified and cloned into the SalI and NotI sites of pPC86 vector (GibcoL BRL) in-frame with the GAL4 AD sequences to generate constructs pPC86-BnSCL1$^{1-358}$, pPC86-BnSCL1$^{1-261}$, pPC86-BnSCL1$^{1-217}$, pPC86-BnSCL1$^{1-145}$, pPC86-BnSCL1$^{146-358}$, pPC86-BnSCL1$^{218-438}$ and pPC86-BnSCL1. PCR amplification was carried out using the following primers:

```
    Forward primer for BnSCL1, BnSCL1¹⁻³⁵⁸,
    BnSCL1¹⁻²⁶¹, BnSCL1¹⁻²¹⁷ and BnSCL1¹⁻¹⁴⁵:
                                                       (SEQ ID NO:96)
    5'-GCGTCGACGATGGACGAACATGCCATGCGTTCCA-3'

Forward primer for BnSCL1¹⁴⁶⁻³⁵⁸:
                                                       (SEQ ID NO:97)
    5'-GCGTCGACGATTAAGGAGTTTTCCGGTATA-3'

Forward primer for BnSCL1²¹⁸⁻⁴³⁴:
                                                       (SEQ ID NO:98)
    5'-GCGTCGACGGAGGATTGCGCCGTCGAGACG-3'

Reverse primer for BnSCL1 and BnSCL1²¹⁸⁻⁴³⁴:
                                                       (SEQ ID NO:99)
    5'-GCGCGGCCGCAAAGCGCCAGGCTGACGTGGC-3'

Reverse primer for BnSCL1¹⁻³⁵⁸:
                                                       (SEQ ID NO:100)
    5'-GCGCGGCCGCCGCGGAGATCTTCGGAC GTAA-3'

Reverse primer for BnSCL1¹⁻²⁶¹:
                                                       (SEQ ID NO:101)
    5'-GCGCGGCCGCCCTAATCGCCTTGAAAGATAA-3'

Reverse primer for BnSCL1¹⁻²¹⁷:
                                                       (SEQ ID NO:102)
    5'-GCGCGGCCGCCGCCACAACCGCCGTGACTCT-3'

Reverse primer for BnSCL1¹⁻¹⁴⁵:
                                                       (SEQ ID NO:103)
    5'-GCGCGGCCGCCGCTCGGATCTTCTGAACAAT-3'

Reverse primer for BnSCL1¹⁴⁶⁻³⁵⁸:
                                                       (SEQ ID NO:100)
    5'-GCGCGGCCGCCGCGGAGATCTTCGGACGTAA-3'.
```

For in vivo protein interaction assays, the MaV203 yeast competent cells carrying the lacZ reporter gene were co-transfected with the construct pDBLeu-HDA19, in which the HDA19 was fused in-fame with GAL4 DB and either of the plasmids pPC86-BnSCL1, pPC86-BnSCL1$^{1-358}$, pPC86-BnSCL1$^{1-261}$, pPC86-BnSCL1$^{1-217}$, pPC86-BnSCL1$^{1-145}$, pPC86-BnSCL1$^{146-358}$, pPC86-BnSCL1$^{218-438}$ and or the vector pPC86 alone. The expression of lacZ reporter gene was quantified by measuring the β-galactosidase activity using CPRG (chlorophenol red-β-D-galactopyranoside) according to the manufacturer's instructions (GibcoL BRL). Three yeast control strains A, B, and C (GibcoL BRL) that contain plasmid pairs expressing fusion proteins with none, weak and moderately strong interaction strengths, respectively, were used as controls.

Transactivation Assay

MaV203 yeast cells expressing the lacZ reporter gene driven by a promoter containing GAL4 DNA binding sites (GibcoL BRL) were transformed with the pDBLeu-bnKCP1$^{1-160}$, pDBLeu-bnKCP1$^{1-80}$, pDBLeu-bnKCP1$^{81-215}$ and pDBLeu-bnKCP1. These vectors were constructed by ligating the PCR-amplified fragments, ΔBnSCL1$^{1-358}$, ΔBnSCL1$^{1-261}$, ΔBnSCL1$^{1-217}$, ΔBnSCL1$^{1-145}$, ΔBnSCL1$^{146-358}$ and ΔBnSCL1$^{218-434}$ and the entire coding region of BnSCL1, respectively, into the SalI and NotI sites of the vector pDBLeu (GibcoL BRL) in-frame with the GAL4 DB sequence. The oligonucleotide primers for the amplification were the same as those used for the in vivo protein interaction assays. The β-galactosidase activity was measured using CPRG according to the manufacturer's instructions (GibcoL BRL). In addition to the yeast strains A, B and C, the yeast strains D (GibcoL BRL) that contain plasmid pairs expressing fusion protein with strong interaction strength was used as controls.

Cloning and Sequence Analysis of the BnSCL1 Gene

HDAC or HAT is recruited to specific loci by large protein complexes made up of transcription activators/co-activators and repressors/co-repressors, respectively (See reviews Kuo and Allis, 1998; Meyer, 2001). Identification of these transcription regulatory proteins that interact with HDAC or HAT is a direct approach to defining nuclear factors that recruit these chromatin remodelling regulators to their target promoters and hence affect the expression of the target genes. To isolate proteins that bind to HDAC in B. napus, the ORF of Arabidopsis thaliana HDA19 fused to the yeast Gal4 DNA binding domain was used as bait in a yeast two-hybrid screening of a B. napus cDNA library linked to the yeast Gal4 activation domain. A number of positive clones were obtained on the basis of the induction of three yeast reporter genes HIS3, URA3 and lacZ followed by retransformation and sequencing analysis. One of these clones encodes a 51.2 kDa protein with pI 5.1, designated BnSCL1 (Brassica napus SCARECROW-like protein 1; SEQ ID NO:81). As shown in FIG. 20, BnSCL1 contains several domains of the SCARECROW (SCR) family of transcription factors (Laurenzio et al., 1996).

Sequence analysis revealed that BnSCL1 cDNA (2781 bp) contains two open reading frames (ORFs). The first ORF (ORF1) encodes BnSCL1, a polypeptide of 461 amino acid residues starting at 82 bp from the 5' end, and ORF2 codes for a polypeptide of 281 amino acids starting at 1687 bp from the 5' end. The linking region of the two ORFs is a short sequence of 200 bp. Database search using NCBI blast program (Altschul et al., 1997) indicated that the deduced amino acid sequence encoded by ORF2 was similar to the human polyposis coli region hypothetical protein DP1 (accession number A39658), which contains a TB2_DP1_HVA22 domain. However, the GENESCAN program (Burge and Karlin, 1997) predicts that the 2781 bps of BnSCL1 cDNA encodes one polypeptide only, i.e. the deduced amino acid sequence of ORF1.

Figure 21:
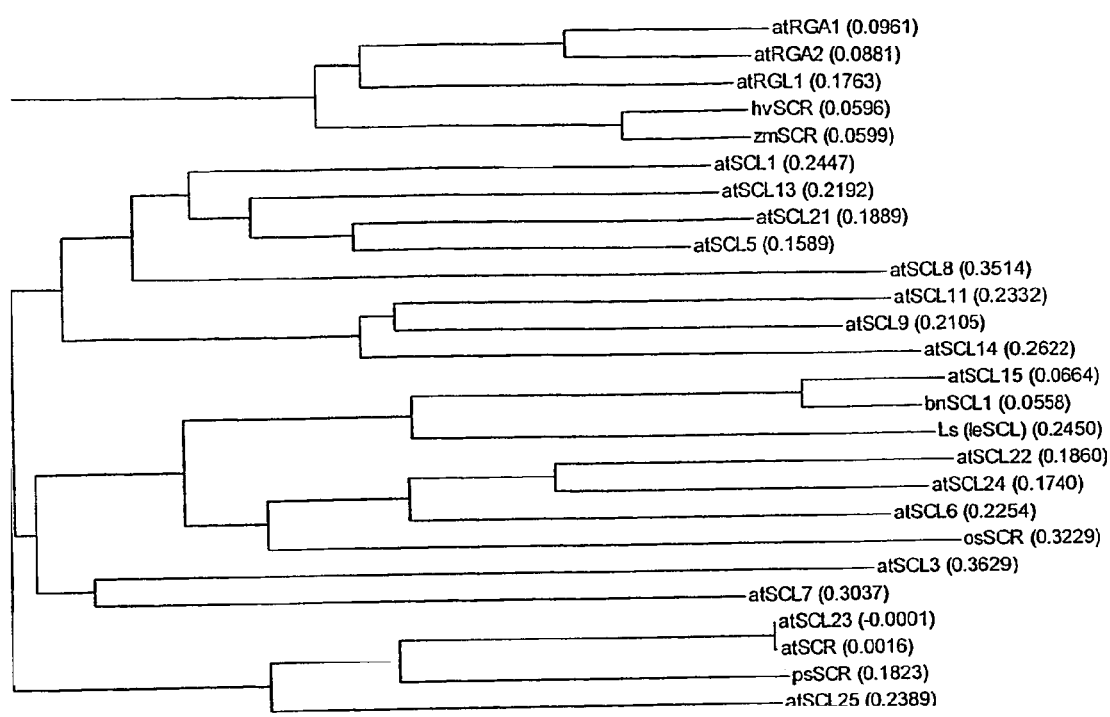
FIG. 21 shows a phylogenetic tree of the GRAS family sequences made by the NTI Vector program in Brassica napus, Arabidopsis thaliana, Hordeum vulgare, Zea mays, Lycopersicon esculentum, Pisum sativum and Oryza sativa. The BnSCL1 is underlined.

Comparison of the deduced BnSCL1 amino acid sequence to the NCBI (see URL:.ncbi.nln.nih.gov) and TAIR (see URL:arabidopsis.org) databases results in a list of proteins with considerable similarity (FIG. 21). According to the NTI computer program (InforMax, Inc.), BnSCL1 shares an 89% amino acid identity with AtSCL15 (Pysh et al., 1999) or VHS5 (Silverstone et al., 1998), an *Arabidopsis* SCARE-CROW-like protein (accession number Z99708, At4g36710), while it is 37% identical to AtSCR (accession number U62797). Interestingly, it also shares high similarity (66% sequence identity) with a tomato (*Lycopersicon esculentum*) protein (accession number AF273333), a member of the GRAS/VHIID protein family, encoded by the Lateral suppressor gene (Ls) (Schumacher et al., 1999) (FIG. 20). Consistent with these data, phylogenetic analysis using either NTI Vector or DNA Star program classified BnSCL1, AtSCL15 and LsSCL (Ls) in the same subgroup (FIG. 21).

Figure 22:
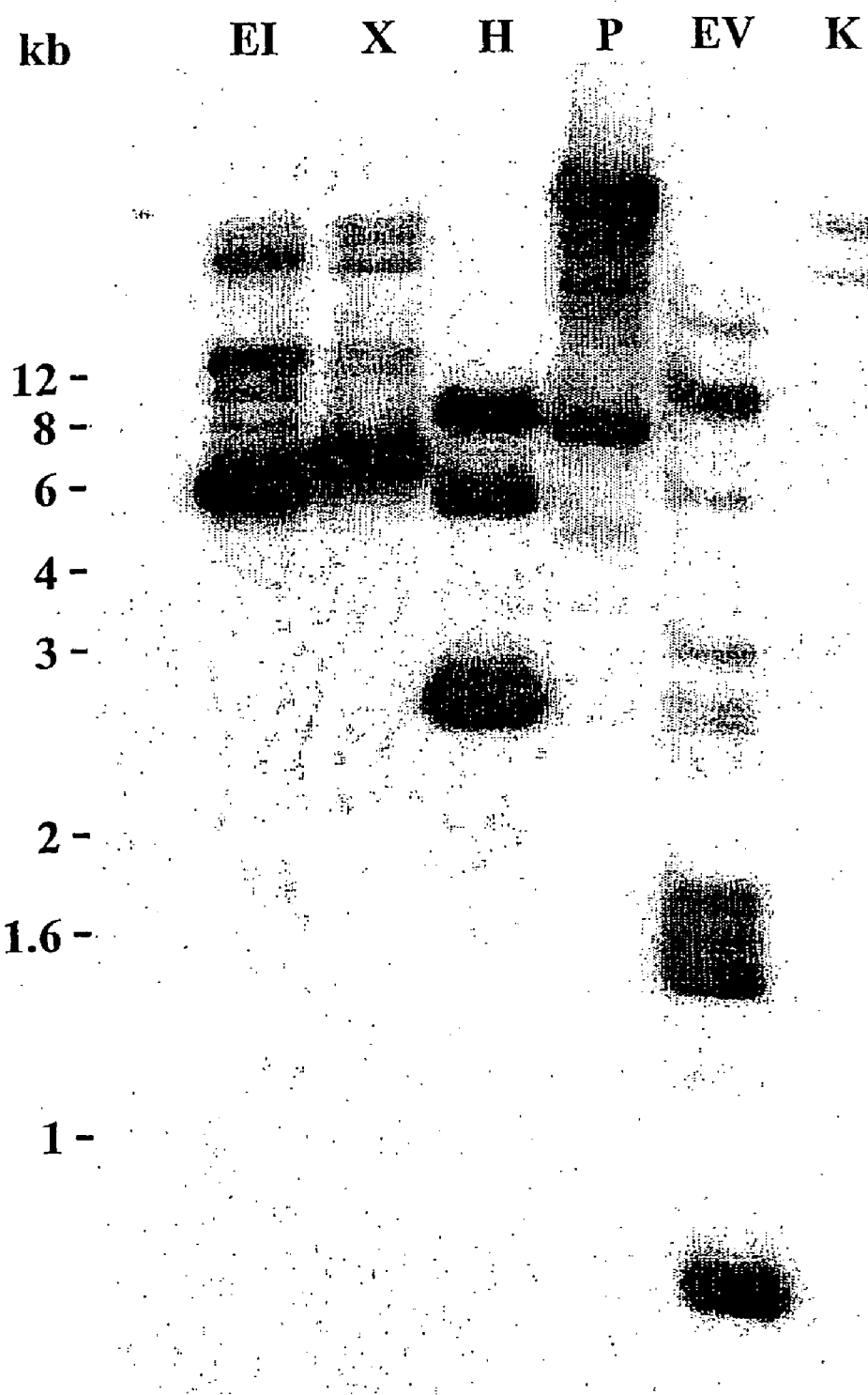
FIG. 22 shows DNA gel blot analysis of BnSCL1 gene. Total genomic DNA (10 µg/lane) from Brassica napis was digested with restriction enzymes EcoRI (ED), XbaI (X), HindIII (H), PstI (P), EcoRV (EV) and KpnI (K), and hybridized with the entire ORF of BnSCL1 under high stringency conditions.

The BnSCL1 copy number in *B. napus* was estimated using DNA gel blot analysis on total genomic DNA digested with restriction endonucleases and hybridized with the ORF of BnSCL1 under high stringency conditions (FIG. 22). Digestion with EcoRI, XbaI, HindIII, PstI and KpnI resulted in the detection of about three bands, whereas digestion with EcoRV generated approximately six bands due to the existence of an internal cutting site for EcoRV within the BnSCL1 gene. This result indicates that BnSCL1 belongs to a small gene family of approximately three members in the *B. napus* genomes.

BnSCL1 is a Member of GRAS/VHIID Family

The BnSCL1 gene encodes a polypeptide of 461 amino acids with several suggestive functional domains or motifs (FIG. 20). It has two MAT α2-like nuclear localization signals (NLSs) (residues 169-173 and 436440) (Raikhel, 1992). It also has a LXXLL motif ($^{148}$LGSLL$^{152}$ (SEQ ID NO:104)) that was shown to mediate interaction of transcription coactivators with nuclear receptors (Heery et al., 1997). Amino acid sequence analysis also revealed that BnSCL1 has the characteristic structure for GRAS/VHIID regulatory proteins (Pysh et al., 1999), including a VHIID motif that encompasses a putative NLS, two leucine heptad repeats (LHRs) that surround the conserved VHIID motif, a PFYRE motif and a C-terminal SAW motif that encompasses a putative NLS (FIG. 20). The LHRI-VHIID-LHRII region has been thought to function in protein-protein and DNA-protein interactions (Pysh et al., 1999).

BnSCL1 Interacts Physically with HDA19 in Vitro and in Vivo

To confirm the interaction of BnSCL1 protein with HDA19 that was detected in the yeast two-hybrid system, GST pull-down affinity assays were carried out using in vitro-translated BnSCL1 labeled with [$^{35}$S]Methionine. The BnSCL1 protein was tested for its binding ability to GST-HDA19 fusion protein that was expressed in *Escherichia coli* and purified under non-denaturing conditions. As shown in FIG. 23, BnSCL1 bound to recombinant HDA19 protein, while it did not bind to GST alone (data not shown).

To map the protein binding domain of the BnSCL1 protein, four C-terminal truncated mutants of BnSCL1 lacking either of the SWA, PFYRE, LHRII or VHlID motif (FIG. 23a) were constructed. These truncated mutants were assayed for in vitro interaction with the recombinant HDA19 protein. As shown in FIG. 23b, the mutant proteins exhibited interaction with GST-HDA19 fusion protein with the truncation from C-terminal end until the VHIID region was deleted, indicating that the VHIID domain is essential for BnSCL1 protein binding to HDA19.

The requirement of the VHIID domain for protein-protein interaction was also demonstrated in vivo using the yeast two-hybrid system (FIG. 24). MaV203 yeast cells were co-transformed with plasmid pDBLeu-HDA19 and either pPC86-BnSCL1, pPC86-BnSCL1$^{1-358}$, pPC86-BnSCL1$^{1-261}$, pPC86-BnSCL1$^{1-217}$, pPC86-BnSCL1$^{1-145}$, pPC86-Bn-SCL1$^{146-358}$, pPC86-BnSCL1$^{218-438}$ and or the vector pPC86 alone. Although β-galactosidase activity was reduced by at least 50% when pDBLeu-expressing cells were transformed with plasmids expressing either of the six mutants of BnSCL1 protein, as compared to the wild type BnSCL1, the transformants with plasmids expressing either pPC86-BnSCL1$^{1-145}$ or pPC86-BnSCL1$^{218-438}$, both of which lacked VHIID motif, showed a further at least 50% reduction in β-galactosidase activity as compared to the other mutants. This finding indicates that VHIID domain is critical for BnSCL1 interaction with HDA19 in vivo.

BnSCL1 Activates Transcription of a Reporter Gene in Yeast

To further characterize the biological function of BnSCL1, its functions as a transcription activator was investigated. Transactivation experiments were performed in yeast (FIG. 25), whereby a yeast strain carrying three reporter genes, lacZ, HIS3 and URA3, driven by promoters fused to GAL4 DNA binding sites and independently integrated into the yeast genome were transfected with the effector plasmid pDBLeu-BnSCL1 comprising BnSCL1 fused to the GAL4 DB under the control of the ADH promoter. Transformation with the effector plasmid resulted in increasing β-galactosidase activity similar with yeast strain D that contains plasmid pairs expressing fusion proteins with strong protein-protein interaction and approximately 20-fold relative to either vector pDBLeu alone or yeast control strain A, which contains plasmid pairs expressing fusion proteins without protein-protein interaction (FIG. 25). Reporter genes HIS3 and URA3 were also strongly transactivated by BnSCL1 protein (data not shown). These results indicate that BnSCL1 significantly exhibits transcription activator activity in yeast.

Figure 6A:
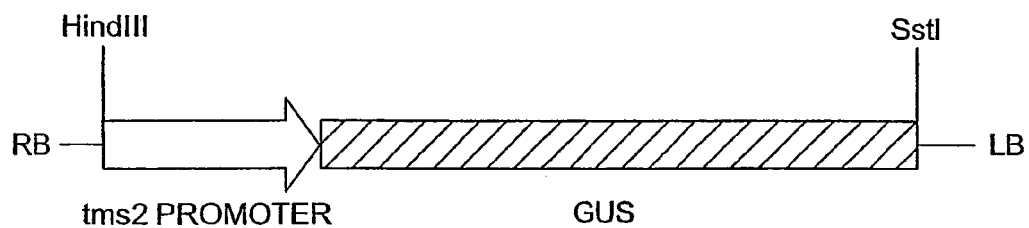
FIG. 6(A) shows the nucleotide construct p76-507 in which a tms2 regulatory region is operatively linked to a gene of interest (in this case encoding β-glucuronidase, GUS).
Figure 6B:
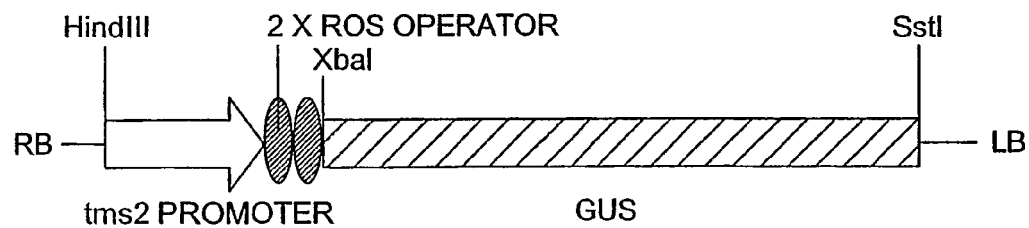
FIG. 6(B) shows the nucleotide construct p76-508 in which a tms2 regulatory region modified to contain two tandemly repeated ROS operator sites downstream of the TATA box is transcriptionally fused (i.e. operatively linked) to the protein coding region of GUS.

To map the transactivation domain of the BnSCL1 activator, a series of deletion mutants of BnSCL1 protein were generated (FIG. 25a) and used in vivo transactivation assays in yeast. As shown in FIG. 6b, either of the deletions from C-terminal of BnSCL1 or any truncation from the N-treminal resulted in a decrease of at least 85% in β-galactosidase activity relative to the wild type BnSCL1 protein. This demonstrates that the transactivation domain of bnKCP1 may reside in both the N- and C-terminal regions.

BnSCL1 Gene is Expressed Mainly in Roots

The expression pattern of the BnSCL1 gene was analyzed by RNA gel blot analysis and quantitative RT-PCR using total RNA extracted from various organs of *B. napus* (FIG. 26). As shown in FIG. 26a, there were two bnSCL1 transcripts of 1.6 kb and 2.8 kb in the RNA blot probed with the ORF of BnSCL1, suggesting the existence of either two species of BnSCL1 cDNA produced by alternative splicing in *B. napus* genome or a BnSCL1 homologue cross-hybridizing to the probe. Both of them accumulated at highest levels in roots, whereas its expression was weak in flowers and stems, and undetectable in leaves and siliques. Results obtained using quantitative RT-PCR analysis (FIG. 26b) were consistent with those obtained with northern blotting. In addition, RT-PCR analysis revealed strong expression in seedling shoots (FIG. 26b). This expression pattern is similar to that of *Arabidopsis* SCR gene (Laurenzio et al., 1996) and to those of most SCLs (Pysh et al., 1999). This suggests that BnSCL1 and SCR may share similar functions in the regulation of root development.

BnSCL1 Responds to Auxin Treatment

Figure 27:
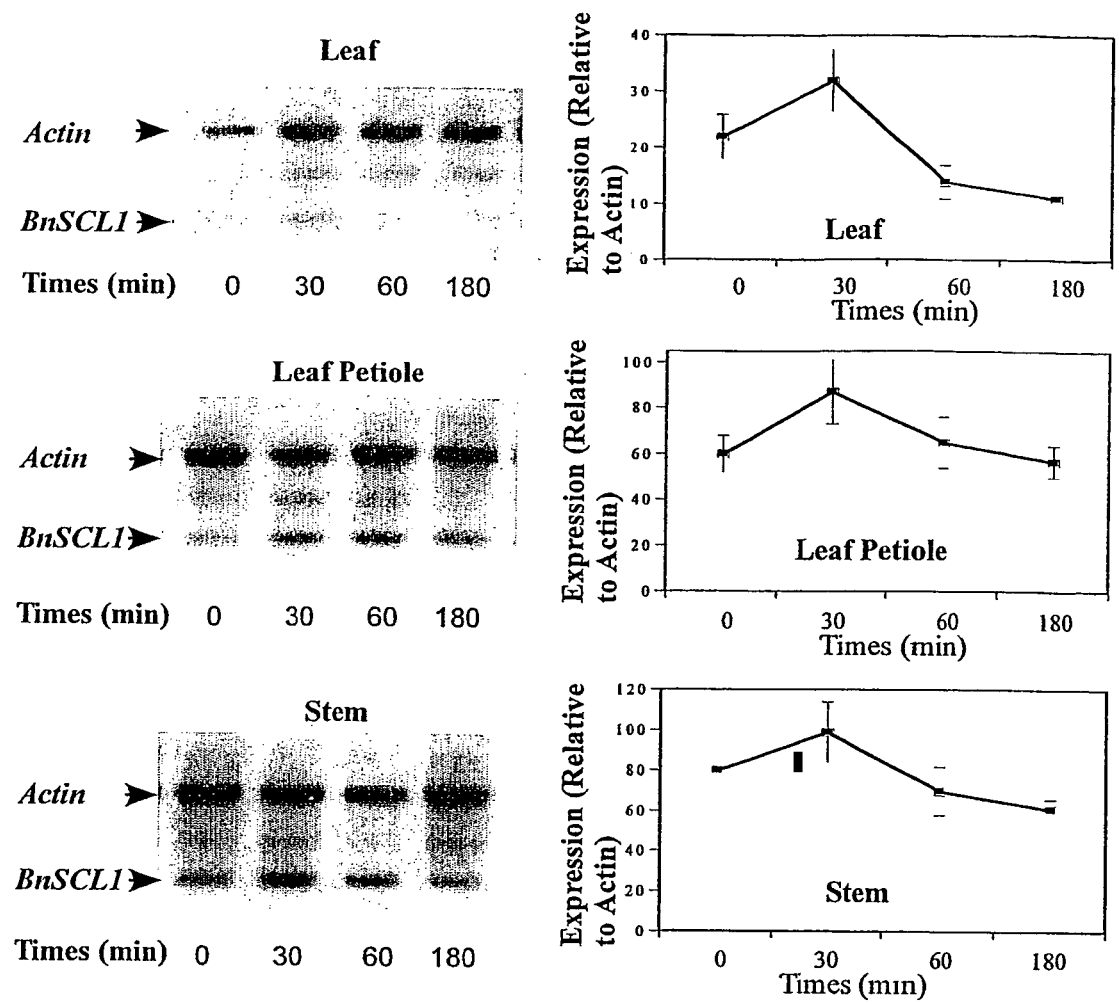
FIG. 27 shows expression of BnSCL1 gene in four-leaf stage *Brassica napus* seedlings in the presence or absence of 2,4-D. Total RNA was isolated from the fourth leaves after the indicated period of the first foliar application of 1 mM 2,4-D and subjected to quantitative one-step RT-PCR. The RT-PCR products were analyzed by Southern blotting using the BnSCL1 ORF as probe (left) and the blotting results were shown graphically relative to the level of internal standard Actin (arbitrary value of 100)(right).

The plant hormone auxin plays an important role in cell division, cell elongation, cell differentiation, lateral root initiation and gravitropism (Davies, 1995; Berleth and Sachs, 2001; Liscum and Stowe-Evans, 2000). Recent studies have demonstrated that auxin distribution organizes the pattern and polarity in the root meristem (Sabatini et al., 1999). To determine whether the dominant role of SCARECROW-like proteins (SCLs) in root biology is associated with auxin, quantitative RT-PCR was used to examine the expression of BnSCL1 gene in four-leaf stage- and 10 dpg-seedlings treated with the synthetic auxin 2,4-D. As shown in FIG. 27, BnSCL1 mRNA accumulation increased by approximately 50% within 30 min of application of 1 mM 2,4-D), and then decreased rapidly to a lower level, when compared to untreated plants (FIG. 27).

Auxin levels are known to modulate the degradation rate of Aux/IAA (auxin/indole-3-acetic acid protein) family members through a proteolytic regulation mechanism (Zenser et al., 2001). To examine whether auxin levels also influences the expression pattern of BnSCL1 gene, quantitative RT-PCR was used to analyse total RNA isolated from shoots and roots of 10 dpg seedlings treated with variable concentrations of 2,4-D ranging from 1 pM to 1 mM (FIG. 28). Expression of BnSCL1 in shoots was rapidly downregulated by auxin even at the lowest level (1 pM) of 2,4-D, indicating that BnSCL1 response to auxin is very sensitive (FIG. 28*a*). BnSCL1 expression in roots, however, was upregulated by auxin although application of a higher concentration (100 μM) of auxin was required to produce an effect (FIG. 28*b*). To determine whether response of BnSCL1 gene to auxin was due to the exogenous application rather than the intercellular auxin synthesis, seedlings were treated for 24 h with 50 μM of naphthylphthalamic acid (NPA), a polar auxin transport inhibitor, and the expression of BnSCL1 in response to auxin was analysed using quantitative One-Step RT-PCR. As can be seen in FIG. 28*c*, the BnSCL1 mRNA accumulation profiles were not changed both in shoots and in roots after NPA treatment followed by the application of auxin at different concentrations. These results suggest that the response of BnSCL1 to the application of exogenous auxin was tissue-specific, or the expression of BnSCL1 may be regulated by auxin distribution in plants.

Expression of SCR in apical meristems was found to be controlled by chromatin assembly factor-1 (CAF-1) (Kaya et al., 2001), and auxin gene expression mutations to be located within an *Arabidopsis* RPD3-like histone deacetylase gene, HDA6, using map-based cloning approach (Murfett et al., 2001). However, no alterations in gene expression of endogenous auxin response genes were detected in the mutants and no effect of auxin-inducible GUS expression was found after seedlings were treated with HADC inhibitor sodium butyrate at concentration up to I mM for 24 h (Murfett et al., 2001). To determine whether BnSCL1 response to auxin is modulated by HDA19, 9 dpg seedlings were treated with 2,4-D at concentrations ranging from $10^{-6}$ to $10^3$ μM or treated with 50 mM of sodium phosphate buffer as control after sodium butyrate treatment for 24 h at a concentration of 10 mM. Relative expression was investigated using quantitative One-Step RT-PCR to analyze RNA extracted from shoots and roots of seedlings. As shown in FIG. 28, although the expression pattern of BnSCL1 in response to auxin in shoots was different from that in roots, the inhibition of histone deacetylase led to the expression profiles of BnSCL1 in shoots were similar to those in roots, i.e. the expression was upregulated by auxin at concentration of 1 pM and downregulated by auxin at higher concentrations. The fact that HDAC inhibition led to the alteration of BnSCL1 expression in response to auxin suggests that the response of BnSCL1 to auxin is modulated by histone deacetylase.

These results suggest a molecular mechanism by which BnSCL1 functions as a transcription factor to regulate gene expression by recruiting HDAC to the promoter regions of target genes.

Example 6

Modulation of Activity of a Gene of Interest Using a Recruitment Factor

Two constructs are prepared: 1) an activator+reporter construct (FIG. 29B) carrying the lacZ reporter gene downstream from a Tet operator sequence (Tet-7X), and the BnSCL1 and VP16 genes encoding a VP16-SCL fusion protein that is able to bind the Tet operator sequence; and 2) an effector construct carrying the HDA19 gene (FIG. 29B).

The activator+report construct is introduced and expressed in yeast cells, for example MaV203 cells as described in Example 4, to produce a reporter yeast. Activity of lacZ product is quantified by measuring the β-galactosidase activity using chlorophenol red-β-D-galactopyranoside (CPRG) (GibcoL BRL). In the reporter yeast, expression of the activator+reporter construct results in the expression of the VP16-SCL fusion protein that binds to the Tet operator sequence, thereby activating expression of the LacZ reporter gene due to VP16.

The reporter yeast expressing the activator+reporter construct is treated with tetracycline. Expression of lacZ reporter gene is quantified by measuring the β-galactosidase activity using chlorophenol red-β-D-galactopyranoside (CPRG). The expression of the activator+reporter construct in the presence of tetracycline in yeast cells produces a baseline level of LacZ activity.

The effector construct is then introduced into the reporter yeast so that the activator+reporter and the effector constructs are both expressed, and the activity of the LacZ product determined as indicated above. Results demonstrate that LacZ activity is reduced in the yeast expressing both the activator+reporter and the effector constructs, when compared to LacZ activity determined in the reporter yeast expressing only the activator+reporter construct, and approximates the level of activity of LacZ activity produced by the reporter yeast when treated with tetracycline.

This result indicate that the expression of a gene of interest (in this case LacZ) may be reduced by targeting a recruitment factor, for example SCL1, to the nucleotide sequence encoding the gene of interest, and permitting the recruitment factor to bind an HDAC.

A similar set of assays is carried out comprising three constructs: 1) a reporter construct carrying the lacZ reporter gene, 2) an activator construct carrying the BnSCL1 and VP16 genes, and 3) an effector construct carrying the HDA19 gene (see FIG. 29A). The constructs are expressed in yeast cells, for example MaV203 cells as described above in Example 4, in the following combinations:

reporter construct alone,
reporter and activator constructs,
reporter, activator and effector constructs.

The expression of lacZ reporter gene is quantified by measuring the β-galactosidase activity using chlorophenol red-β-D-galactopyranoside (CPRG) (GibcoL BRL).

The expression of the reporter construct alone in yeast cells produces a baseline level of β-galactosidase activity. Expression of both the reporter and activator constructs yields an elevated level of β-galactosidase activity, when compared with the activity observed in the presence of the reporter construct alone, while the reporter, activator and effector constructs together results in approximately background levels of β-galactosidase activity.

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Ahmad, A., Takami, Y. and Nakayama, T. (1999) WD repeats of the p48 subunit of chicken chromatin assembly factor-1 required for in vitro interaction with chicken histone deacetylase-2. *J. Biol. Chem.* 274, 16646-16653.

An, Y. Q., McDowell, J. M., Huang S., McKinney, E. C., Chambliss S. and Meagher, R. B. (1996) Strong, constitutive expression of the *Arabidopsis* ACT2/ACT8 actin subclass in vegetative tissues. *Plant J.,* 10: 107-121

Aoyama, T. and Chua, N. H., 1997, Plant J. 2, 397-404

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. *Nucleic Acids Res.* 25, 3389-3402.

Archdeacon, J., Bouhouche, N., O'Connell, F., Kado, C. I. (2000) A single amino acid substitution beyond the C2H2-zinc finger in Ros derepresses virulence and T-DNA genes in *Agrobacterium tumefaciens*. FEMS Microbiol Let. 187, 175-178

Bannister, A. J. and Kouzarides, T. (1996). The CBP co-activator is a histone acetyltransferase. Nature, 384, 641-643

Beetham, P. R., Kipp, P. B., Sawycky, X. L., Arntzen, C. J., May, G. D. (1999) A tool for functional plant genomics: chimeric RNA/DNA oligonucleotides cause in vivo gene-specific mutations. Proc. Natl. Acad. Sci. USA, 96: 8774-8778

Berleth T, Sachs T. (2001) Plant morphogenesis: long-distance coordination and local patterning. Curr Opin Plant Biol, 4:57-62.

Bittinger, M. A., Milner, J. L., Saville, B. J., Handelsman, J. (1997) rosR, a determinant of nodulation competitiveness in *Rhizobium etli*. Mol. Plant Microbe Interact. 10: 180-186

Boyle, B. and Brisson, N. (2001) Repression of the defense gene PR-10a by the single-stranded DNA binding protein SEBF. *Plant Cell* 13, 2525-2537.

Brandstatter, I. and Kieber, J. J. (1998) Two genes with similarity to bacterial response regulators are rapidly and specifically induced by cytokinin in Arabidopsis. Plant Cell 10, 1009-1019

Brightwell, G., Hussain, H., Tiburtius, A., Yeoman, K. H., Johnston, A. W. (1995) Pleiotropic effects of regulatory ros mutants of Agrobacterium radiobacter and their interaction with Fe and glucose. Mol. Plant Microbe Interact. 8: 747-754

Burge, C. and Karlin, S. (1997) Prediction of complete gene structures in human genomic DNA. J. Mol. Biol. 268, 78-94.

Caddick, M. X., Greenland, A. J., Jepson, I., Krause, K. P., Qu, N., Riddell, K. V., Salter, M. G., Schuch, W., Sonnewald, U., Tomsett, A. B. (1998) An ethanol inducible gene switch for plants used to manipulate carbon metabolism. Nature Biotech. 16, 177-180

Carrington, J. C., Freed, D. D., Leinicke, A. J. (1991) Bipartite signal sequence mediates nuclear translocation of the plant potyviral NMa protein. Plant Cell, 3: 953-962

Chou, A. Y., Archdeacon, J., Kado, C. I. (1998) *Agrobacterium* transcriptional regulator Ros is a prokaryotic zinc finger protein that regulates the plant oncogene ipt. Proc. Natl. Acad. Sci., 95: 5293

Chrivia, J. C., Kwok, R. P., Lamb, N., Hagiwara, M., Montminy, M. R. and Goodman, R. H. (1993) Photophorylated CREB binds specifically to the nuclear protein CBP. *Nature* 365, 855-859.

Clough, S. J. and Bent, A. F. (1998) Floral dip: a simplified method for *Agrobacterium*-mediated transformation of *Arabidopsis thaliana*. Plant J. 16, 735-743

Cooley, M. B., D'Souza, M. R., Kado, C. I. (1991) The virC and virD operons of the *Agrobacterium* Ti plasmid are regulated by the ros chromosomal gene: analysis of the cloned ros gene. J. Bacteriol. 173: 2608-2616

Cornejo et al, 1993, Plant Mol. Biol. 29: 637-646

Davies, P. J. (1995) Plant Hormones (Dordrecht, The Netherlands: Kluwer Academic Publishers).

D'Souza-Ault, M. R., Cooley, M. B. and Kado, C. I. (1993) Analysis of the Ros repressor of *Agrobacterium* virC and virD operons: molecular intercommunication between plasmid and chromosomal genes. J Bacteriol 175: 3486-3490

Eisner et al., 1998, Ther. Appl. Genet., 97: 801

Emiliani S., Fischle, W., Van Lint, C., Al-Abed, Y., Verdin, E. (1998) Characterization of a human RPD3 ortholog, HDAC3. Proc Natl Acad Sci USA. 95, 2795-800.

Fischle, W., Emiliani, S., Hendzel, M. J., Nagase, T., Nomura, N., Voelter, W., Verdin, E. (1999) A new family of human histone deacetylases related to *Saccharomyces cerevisiae* HDA1p. J Biol Chem. 274, 11713-20.

Fukaki, H., Wysocka-Diller, J., Kato, T., Fujisawa, H., Benfey, P. N. and Tasaka, M. (1998) Genetic evidence that the endodermis is essential for shoot gravitropism in *Arabidopsis thaliana*. Plant J., 14: 425-430.

Gao, M.-J., Allard, G., Byass, L., Flanagan, A. M. and Singh, J. (2002) Regulation and characterization of four CBF transcription factors from *Brassica napus*. *Plant Mol. Biol.* 49: 459-471.

Gao, M.-J. Schäfer, U. A., Parkin, I. A. P., Hegedus, D. D., Lydiate, D. J. and Hannoufa, A. (2003) A novel protein from *Brassica napus* has a putative KID-domain and responds to low temperature. *Plant J.* 33: 1073-1086.

Gao, M.-J., Dvorak, J. and Travis, R. L. (2001) Expression of the extrinsic 23-kDa protein photosystem II in response to salt stress is associated with the $K^+/Na^+$ discrimination locus Kna1 in wheat. *Plant Cell Rep.* 20, 774-778.

Gatz, C., 1997) Ann. Rev. Plant Physiol. Plant Mol. Biol. 48, 89-108

Gatz, C. and Lenk, I. R. P., 1998, Trends Plant Sci. 3, 352-358

Geierson and Corey, Plant Molecular Biology, 2d Ed. (1988)

Gelmetti, V., Zhang, J., Fanelli, M., Minucci, S., Pelicci, P. G., Lazar, M. A. (1998) Aberrant recruitment of the nuclear receptor corepressor-histone deacetylase complex by the acute myeloid leukemia fusion partner ETO. Mol Cell Biol. 18, 7185-91.

Gonzalez, G. A., Menzel, P. Leonard, J., Fischer, W. H. and Montminy, M. R. (1991) Characterization of motifs which are critical for activity of the cyclic AMP-responsive transcription factor CREB. *Mol. Cell Biol.* 11, 1306-1312.

Gonzalez, G. A. and Montminy, M. R. (1989) Cyclic AMP stimulates somatostatin gene transcription by phosphorylation of CREB at serine 133. Cell 59, 675-680.

Grunstein, M. (1997) Histone acetylation in chromatin structure and transcription. *Nature,* 389, 349-352.

Hart, C. M., Nagy, F., Meins, F. Jr. (1993) A 61 bp enhancer element of the tobacco beta-1,3-glucanase B gene interacts with one or more regulated nuclear proteins. Plant Molec. Bio 21:121-131

Hassig, C. A. and Schreiber, S. L. (1997) Nuclear histone acetylases and deacetylases and transcriptional regulation: HATs off to HDACs. Curr Opin Chem Biol. 1, 300-8. OR Hassig, C. A., Fleischer, T. C., Billin, A. N., Schreiber, S. L., Ayer, D. E. (1997) Histone deacetylase activity is required for full transcriptional repression by mSin3A. Cell 89, 341-7.

Hassig, C. A., Tong, J. K., Fleischer, T. C., Owa, T., Grable, P. G., Ayer, D. E., Schreiber, S. L. (1998) A role for histone deacetylase activity in HDAC1-mediated transcriptional-repression. Proc Natl Acad Sci USA. 95, 3519-24.

Helariutta, Y., Fukaki, H., Wysocka-Diller. J., Nakajima, K., Jung, J., Sena, G., Hauser, M.-T. and Benfey, P. N. (2000) The SHORT-ROOT gene controls radial patterning of the *Arabidopsis* root through radial signaling. *Cell,* 101: 555-567.

Holtorf, S., Apel, K. and Bohlmann, H. (1995) Comparison of different constitutive and inducible promoters for the over-expression of transgenes in *Arabidopsis thaliana*. Plant Mol. Biol. 29: 637-646

Hurley, T. W., Ryan, M. P. and Moore, W. C. (1996) Regulation of changes in cytosolic $Ca^{2+}$ and $Na^+$ concentrations in rat submandibular gland acini exposed to carbachol and ATP. *J. Cell Physiol.,* 168: 229-238

Jofuku, K. D., den Boer, B. G., Van Montagn, M., Okamuro, J. K. (1994) Control of *Arabidopsis* flower and seed development by the homeotic gene APETALA2. Plant Cell. 6, 1211-25.

Johnson, C. and Turner, B. M. (1998) Histone deacetylases: complex transducers of nuclear signals. *Cell Dev. Biol.* 10, 179-188.

Johnson, P. F., Stemeck, E. and Williams, S. C. (1993) Activation domains of transcriptional regulatory proteins. *J. Nutr. Biochem.* 4, 386-398.

Kadosh, D. and Struhl, K. (1997) Repression by Ume6 involves recruitment of a complex containing Sin3 core-pressor and Rpd3 histone deacetylase to target promoters. Cell 89, 365-71.

Kakimoto, T. (1996) CKI1, a histidine kinase homolog implicated in cytokinin signal transduction. Science 274, 982-985

Kapila, J., Rycke, R. D., Montagu, M. V. and Angenon, G. (1997) An *Agrobacterium*-mediated transient gene expression system for intact leaves. *Plant. Sci.* 122, 101-108.

Kaya, H., Shibahara, K., Taoka, K., Iwabuchi, M., Stillman, B. and Araki, T. (2001) FASCIATA genes for chromatin assembly factor-1 in *Arabidopsis* maintain the cellular organization of apical meristem. *Cell,* 104: 131-142.

Keller, M., Roxlau, A., Weng, W. M., Schmidt, M., Quandt, J., Niehaus, K., Jording, D., Arnold, W., Puhler, A. (1995) Molecular analysis of the *Rhizobium meliloti* mucR gene regulating the biosynthesis of the exopolysaccharides succinoglycan and galactoglucan. Mol. Plant Microbe Interact. 8: 267-277

Khochbin, S. and Wolffe, A. P. (1997) The origin and utility of histone deacetylases. FEBS Lett. 419, 157-60.

Knight, H., Trewavas, A. J., Knight, M. R. (1996) Cold calcium signaling in *Arabidopsis* involves two cellular pools and a change in calcium signature after acclimation. Plant Cell, 8, 489-503.

Kohno-Murase, J., Murase, M., Ichikawa, H., Ihuamura, J. (1994) Effects of an antisense napin gene on seed storage compounds in transgenic *Brassica napus* seeds. Plant Mol. Biol., 26: 1115-24

Kolle, D., Sarg, B., Lindner, H., Loidl, P. (1998) Substrate and sequential site specificity of cytoplasmic histone acetyltransferases of maize and rat liver. FEBS Lett. 421: 109-114

Kuo, M. H. and Allis, C. D. (1998) Roles of histone acetyltransferases and deacetylases in gene regulation. *Bioessays,* 20, 615-626.

Laurenzio, L. D., Wysocka-Diller, J., Malamy, J. E., Pysh, L., Helariutta, Y., Freshour, G., Hahn, M. G., Feldmann, K. A. and Benfey, P. N. (1996) The SCARECROW gene regulates an asymmetric cell division that is essential for generating the radial organization of the *Arabidopsis* root. *Cell,* 86: 423-433.

Liscum E, Stowe-Evans E L. (2000) Phototropism: a "simple" physiological response modulated by multiple interacting photosensory-response pathways. Photochem Photobiol, 72:273-282.

Lotan, T., Ohto, M., Yee, K. M., West, M. A., Lo, R., Kwong, R. W., Yamagishi, K., Fischer, R. L., Goldberg, R. B., Harada, J. J. (1998) *Arabidopsis* LEAFY COTYLEDON1 is sufficient to induce embryo development in vegetative cells. Cell 93, 1195-1205

Lusser, A., Kolle, D., Loidl, P. (2001) Histone acetylation: lessons from the plant kingdom. Trends in Plant Sci. 6:59-65

Mandel, T., Fleming, A. J., Krahenbuhl, R., Kuhlemeier, C. (1995) Definition of constitutive gene expression in plants: the translation initiation factor 4A gene as a model. Plant Mol. Biol. 29: 995-1004

Meyer, T. E., Waeber, G., Lin, J., Beckmann, W. and Habener, J. F. (1993) The promoter of the gene encoding-3',5'-cyclic adenosine monophosphate (camp) response element binding protein contains camp response elements: evidence for positive autoregulation of gene transcription. *Endocrinology,* 132, 770-780

Miki and Iyer, Fundamentals of Gene Transfer in Plants. In Plant Metabolism, 2d Ed. D T. Dennis, D H Turpin, D D Lefebrve, D B Layzell (eds), Addison Wesly, Langmans Ltd. London, pp. 561-579 (1997)

Monroy and Dhindsa (1995) Annu. Rev. Biochem. 66, 807-822

Montminy, M. R. (1997) Transcriptional regulation by cyclic AMP. Annu. Rev. Biochem. 66, 807-822

Murashige, T. and Skoog, F. (1962) A revised medium for rapid growth and bioassays with tobacco tissue culture. Physiol. Plant. 15: 473-495.

Murashige and Skoog, 1962

Murfett, J., Wang, X. J., Hagen, G. and Guilfoyle, T. J. (2001) Identification of *Arabidopsis* histone deacetylase HDA6 mutants that affect transgene expression. Plant Cell, 13: 1047-1061.

Murray, E. E., Lotzer, J., Eberle, M. (1989) Codon usage in plant genes. Nuc Acids Res. 17:477-498.

Nagy et al., 1997;

Nakai, K. and Kanehisa, M. (1992) A knowledge base for predicting protein localization sites in eukaryotic cells. *Genomics* 14, 897-911.

Nakajima K, Sena G, Nawy T, Benfey P N. (2001) Intercellular movement of the putative transcription factor SHR in root patterning. *Nature,* 20: 413:307-11.

Odell, J. T., Nagy, F., Chua, N. H. (1985) Identification of DNA sequences required for activity of the cauliflower mosaic virus 35S promoter. Nature 313, 810-812

Ogas, J., Cheng, J. C., Sung, Z. R., Somerville, C. (1997) Cellular differentiation regulated by gibberellin in the *Arabidopsis thaliana* pickle mutant. Science 277, 91-94

Ogryzko, V. V., Schiltz, R. L., Russanova, V., Howard, B. H. and Nakatani, Y. (1996) The transcriptional coactivators p300 and CBP are hstone acetyltransferases. *Cell,* 87, 953-959

Pazin, M. J. and Kadonaga, J. T. (1997) What's up and down with histone deacetylation and transcription? Cell 89, 325-8.

Pysh, L. D., Wysocka-Diller, J. W., Camilleri, C., Bouchez, D. and Benfey, P. (1999) The GRAS gene family in *Arabidopsis:* sequence characterization and basic expression analysis of the SCARECROW-LIKE genes. *Plant J.,* 18: 111-119.

Quinn, P. G. (1993) Distinct activation domains within camp response element-binding protein (CREB) mediate basal and camp-stimulated transcription. *J. Biol. Chem.* 268, 16999-117009.

Ridgeway, P. and Almouzni, G. (2000) CAF-1 and the inheritance of chromatin states: at the crossroads of DNA replication and repair. *J. Cell Sci.,* 113: 2647-2658.

Rizzo, P., Di Resta, I., Powers, A., Ratner, H. and Carbone, M. (1999) Unique strains of SV40 in commercial poliovaccines from 1955 not readily identifiable with current testing for SV40 infection. Cancer Res. 59, 6103-6108.

Robbins, J., Dilworth, S. M., Laskey, R. A., Dingwall, C. (1991) Two interdependent basic domains in nucleoplasmin nuclear targeting sequence: identification of a class of bipartite nuclear targeting sequence. Cell, 64: 615-623

Rundlett, S. E., Carmen, A. A., Kobayashi, R., Bavykin, S., Turner, B. M., Grunstein, M. (1996) HDA1 and RPD3 are members of distinct yeast histone deacetylase complexes that regulate silencing and transcription. Proc Natl Acad Sci USA. 93, 14503-8.

Salter, M. G., et al, 1998, Plant Journal 16, 127-132

Sambrook, Fritsch, and Maniatis, Molecular Cloning: A Laboratory Manual (1989), Cold Spring Harbor Sardana et al. (Plant Cell Reports 15:677-681; 1996).

Scheres, B., Di Laurenzio, L., Willemsen, V., Hauser, M.-T., Janmaat, K., Weisbeek, P. and Benfey, P. N. (1995) Mutations affecting the radial organization of the *Arabidopsis* root display specific defects throughout the radial axis. *Development,* 121: 53-62.

Schumacher, K., Schmitt, T., Rossberg, M., Schmitz, G. and Theres, K. (1999) The lateral suppressor (Ls) gene of tomato encodes a new member of the VHIID protein family. *Proc. Natl. Acad. Sci. USA,* 96: 290-295.

Shaywitz, A. J., Dove, S. L., Kornhauser, J. M., Hochschild, A., Greenberg, M. E. (2000) Magnitude of the CREB-dependent transcriptional response is determined by the strength of the interaction between the kinase-inducible domain of CREB and the KIX domain of CREB-binding protein. Mol. Cell. Biol. 20, 9409-9422

Silverstone, A., Ciampaglio, C. N. and Sun T. (1998) The *Arabidopsis* RGA gene encodes a transcriptional regulator repressing the gibberellin signal transduction pathway. *Plant Cell,* 10: 155-169.

Stockinger, E. J., Gilmour, S. J. and Thomashow, M. F. (1997) *Arabidopsis thaliana* CBF1 encodes an AP2 domain-containing transcriptional activator that binds to the C-repeat/ DRE, a cis-acting DNA regulatory element that stimulates transcription in response to low temperature and water deficit. *Proc. Natl. Acad. Sci. USA* 94, 1035-1040.

Stockinger, E. J., Mao, Y., Regier, M. K., Triezenberg, S. J. and Thomashow, M. F. (2001) Transcriptional adaptor and histone acetyltransferase proteins in *Arabidopsis* and their interaction with CBF1, a transcriptional activator involved in cold-regulated gene expression. *Nucleic Acids Res.* 29, 1524-1533.

Struhl, K. (1998) Histone acetylation and transcriptional regulatory mechanisms. *Genes Dev.* 12, 599-606.

Tian, L. and Chen, Z. J. (2001) Blocking histone deacetylation in *Arabidopsis* induces pleiotropic effects on plant gene regulation and development. *Proc. Natl. Acad. Sci. USA,* 98: 200-205.

Tian, Q., Uhlir, N. J. and Reed, J. W. (2002) *Arabidopsis* SHY2/IAA3 inhibits auxin-regulated gene expression. *Plant Cell,* 14: 301-319.

Ulmasov, T., Murfett, J., Hagen, G., Guilfoyle, T. J. (1997) Aux/IAA proteins repress expression of reporter genes containing natural and highly active synthetic auxin response elements. Plant Cell 9, 1963-1971 van der Krol, A. R. and Chua, N. H. (1991) The basic domain of plant B-ZIP proteins facilitates import of a reporter protein into plant nuclei. Plant Cell, 3: 667-675

Varagona, M. J., Schmidt, R. J., Raikhel, N. V. (1992) Nuclear localization signal(s) required for nuclear targeting of the maize regulatory protein Opaque-2. Plant Cell, 4: 1213-1227.

Varagona, M. J., Schmidt, R. J. and Raikhel, N. V. (1991) Monocot regulatory protein Opaque-2 is localized in the nucleus of maize endosperm and transformed tobacco plants. *Plant Cell* 3, 105-113.

Verbsky, M. and Richards, E. J. (2001) Chromatin remodeling in plants. *Curr. Opin. Plant Biol.* 4, 494-500.

Verdel, A. and Khochbin, S. (1999) Identification of a new family of higher eukaryotic histone deacetylases. Coordinate expression of differentiation-dependent chromatin modifiers. J Biol Chem. 274, 2440-5.

Vidal, M. and Gaber, R. F. (1991) RPD3 encodes a second factor required to achieve maximum positive and negative transcriptional states in *Saccharomyces cerevisiae.* Mol Cell Biol. 11, 6317-27.

Weissbach and Weissbach, Methods for Plant Molecular Biology, Academy Press, New York VIII, pp. 421-463 (1988)

Wu, K., Malik, K., Tian, L., Brown, D. and Miki, B. (2000a) Functional analysis of a RPD3 histone deacetylase homologue in *Arabidopsis thaliana. Plant Mol Biol.* 44:167-176.

Wu, K., Tian L., Malik K., Brown D. and Miki B. (2000b) Functional analysis of HD2 histone deacetylase homologues in *Arabidopsis thaliana.* Plant J. 22: 19-27. (is this the correct full citation for Wu et al. 2000, Plant J. 22:1-9??)

Xu, Y., Yu, H., Hall, T. C. (1994) Rice Triosephosphate Isomerase Gene 5[prime] Sequence Directs [beta]-Glucuronidase Activity in Transgenic Tobacco but Requires an Intron for Expression in Rice. Plant Physiol. 106: 459-467.

Yanovsky et al., 1990, Nature, 346: 35-39

Zenser, N., Ellsmore, A., Leasure, C. and Callis, J. (2001) Auxin modulates the degradation rate of Aux/IAA proteins. *Proc. Natl. Acad. Sci. USA,* 98: 11795-11800.

Zhang, W., McElroy, D., Wu, R. (1991) Analysis of rice Act1 5' region activity in transgenic rice plants. Plant Cell, 3: 1155-1165

Zhu, T., Peterson, D. J., Tagliani, L., St Clair, G., Baszczynski, C. L., Bowen, B. (1999) Targeted manipulation of maize genes in vivo using chimeric RNA/DNA oligonucleotides. Proc. Natl. Acad. Sci. USA, 96: 8768-73.

The embodiments of the invention in which an exclusive property of privilege is claimed are defined as follows:

1. An isolated nucleic acid sequence encoding the sequence of BnSCL1 as set forth in SEQ ID NO:81.

2. The isolated nucleic acid sequence encoding amino acids 1 to 217 of SEQ ID NO:81.

3. The isolated nucleic acid sequence of claim 2, encoding amino acids 1 to 358 of SEQ ID NO:81.

4. The isolated nucleic acid sequence of claim 2, encoding amino acids 1 to 261 of SEQ ID NO:81.

5. The isolated nucleic acid sequence encoding amino acids 146 to 358 of SEQ ID NO:81.

6. A construct comprising the insolated nucleic acid of claim 1, operatively linked with a regulatory region.

7. A construct comprising an isolated nucleic acid operatively linked with a regulatory region, wherein the isolated nucleic acid is selected from the group consisting of the nucleic acid sequence encoding 1 to 358 of SEQ ID NO:81, the nucleic acid sequence encoding 1 to 261 of SEQ ID NO:81, the nucleic acid sequence encoding 1 to 217 of SEQ ID NO:81, and the nucleic acid sequence encoding 146 to 358 of SEQ ID NO:81.

8. The construct of claim 6, wherein the isolated nucleic acid further comprises a nucleic acid sequence encoding DNA binding protein.

9. The construct of claim 7, wherein the isolated nucleic acid further comprises a nucleic acid sequence encoding DNA binding protein.

10. A transgenic plant comprising the construct of claim 6.

11. A transgenic plant comprising the construct of claim 7.

12. A transgenic plant comprising the construct of claim 8.

13. A transgenic plant comprising the construct of claim 9.

* * * * *

SEQUENCE LISTING

<160> NUMBER OF SEQ ID NOS: 104

<210> SEQ ID NO 1
<211> LENGTH: 142
<212> TYPE: PRT
<213> ORGANISM: Agrobacterium Tumefaciens
<220> FEATURE:
<223> OTHER INFORMATION: WT-ROS

<400> SEQUENCE: 1

Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Val Pro Val
                20                  25                  30

Thr Glu Leu Pro Gly Leu Ile Ser Asp Val His Thr Ala Leu Ser Gly
            35                  40                  45

Thr Ser Ala Pro Ala Ser Val Ala Val Asn Val Glu Lys Gln Lys Pro
        50                  55                  60

Ala Val Ser Val Arg Lys Ser Val Gln Asp Asp His Ile Val Cys Leu
65                  70                  75                  80

Glu Cys Gly Gly Ser Phe Lys Ser Leu Lys Arg His Leu Thr Thr His
                85                  90                  95

His Ser Met Thr Pro Glu Glu Tyr Arg Glu Lys Trp Asp Leu Pro Val
                100                 105                 110

Asp Tyr Pro Met Val Ala Pro Ala Tyr Ala Glu Ala Arg Ser Arg Leu
            115                 120                 125

Ala Lys Glu Met Gly Leu Gly Gln Arg Arg Lys Ala Asn Arg
        130                 135                 140

<210> SEQ ID NO 2
<211> LENGTH: 472
<212> TYPE: DNA
<213> ORGANISM: Artificial Sequence
<220> FEATURE:
<223> OTHER INFORMATION: Synthetic ROS

<400> SEQUENCE: 2
gcggatcccc gggtatgact gagactgctt acggtaacgc tcaggatctt cttgttgagc      60
ttactgctga tatcgttgct gcttacgttt ctaaccacgt tgttcctgtt actgagcttc     120
ctggacttat ctctgatgtt catactgcac tttctggaac atctgctcct gcttctgttg     180
ctgttaacgt tgagaagcag aagcctgctg tttctgttcg taagtctgtt caggatgatc     240
atatcgtttg tttggagtgt ggtggttctt tcaagtctct caagcgtcac cttactactc     300
atcactctat gactccagag gagtatagag agaagtggga tcttcctgtt gattacccta     360
tggttgctcc tgcttacgct gaggctcgtt ctcgtctcgc taaggagatg gtctcggtc      420 agcgtcgtaa ggctaaccgt ccaaaaaaga agcgtaaggt ctgagagctc gc              472

<210> SEQ ID NO 3
<211> LENGTH: 447
<212> TYPE: DNA
<213> ORGANISM: Artificial Sequence
<220> FEATURE:
<223> OTHER INFORMATION: Composite ROS Sequence
<220> FEATURE:
<221> NAME/KEY: misc_feature
<222> LOCATION: (6)..(6)
<223> OTHER INFORMATION: n is a, c, g, or t
<220> FEATURE:

-continued

```
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
```

```
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
```

```
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
```

```
<222> LOCATION: (285)..(285)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
```

```
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

<400> SEQUENCE: 3
atgacngara cngcntaygg naaygcncar gayytnytng tngarytnac ngcngayath    60
gtngcngcnt aygtnwsnaa ycaygtngtn ccngtnacng arytnccngg nytnathwsn   120
gaygtncaya cngcnytnws nggnacnwsn gcnccngcnw sngtngcngt naaygtngar   180
aarcaraarc cngcngtnws ngtnmgnaar wsngtncarg aygaycayat hgtntgyytn   240
gartgyggng gnwsnttyaa rwsnytnaar mgncayytna cnacncayca ywsnatgacn   300
ccngargart aymgngaraa rtgggayytn ccgtngayt ayccnatggt ngcnccngcn    360
taygcngarg cnmgnwsnmg nytngcnaar garatgggny tnggncarmg nmgnaargcn   420
aaymgnccna araaraarmg naargtn                                      447

<210> SEQ ID NO 4
<211> LENGTH: 149
<212> TYPE: PRT
<213> ORGANISM: Artificial Sequence
<220> FEATURE:
<223> OTHER INFORMATION: Synthetic ROS

<400> SEQUENCE: 4

Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Pro Val
                20                  25                  30

Thr Glu Leu Pro Gly Leu Ile Ser Asp Val His Thr Ala Leu Ser Gly
            35                  40                  45

Thr Ser Ala Pro Ala Ser Val Ala Val Asn Val Glu Lys Gln Lys Pro
        50                  55                  60
```

-continued

```
Ala Val Ser Val Arg Lys Ser Val Gln Asp Asp His Ile Val Cys Leu
 65                  70                  75                  80

Glu Cys Gly Gly Ser Phe Lys Ser Leu Lys Arg His Leu Thr Thr His
                 85                  90                  95

His Ser Met Thr Pro Glu Glu Tyr Arg Glu Lys Trp Asp Leu Pro Val
            100                 105                 110

Asp Tyr Pro Met Val Ala Pro Ala Tyr Ala Glu Ala Arg Ser Arg Leu
        115                 120                 125

Ala Lys Glu Met Gly Leu Gly Gln Arg Arg Lys Ala Asn Arg Pro Lys
    130                 135                 140

Lys Lys Arg Lys Val
145

<210> SEQ ID NO 5
<211> LENGTH: 10
<212> TYPE: PRT
<213> ORGANISM: Artificial Sequence
<220> FEATURE:
<223> OTHER INFORMATION: ROS Binding

<400> SEQUENCE: 5

Trp Ala Thr Asp His Trp Lys Met Ala Arg
 1               5                  10

<210> SEQ ID NO 6
<211> LENGTH: 7
<212> TYPE: PRT
<213> ORGANISM: SV 40
<220> FEATURE:
<223> OTHER INFORMATION: NLS

<400> SEQUENCE: 6

Pro Lys Lys Lys Arg Lys Val
 1               5

<210> SEQ ID NO 7
<211> LENGTH: 25
<212> TYPE: DNA
<213> ORGANISM: Agrobacterium Tumefaciens
<220> FEATURE:
<223> OTHER INFORMATION: ROS Operator

<400> SEQUENCE: 7
tatatttcaa ttttattgta atata                                    25

<210> SEQ ID NO 8
<211> LENGTH: 27
<212> TYPE: DNA
<213> ORGANISM: Agrobacterium Tumefaciens
<220> FEATURE:
<223> OTHER INFORMATION: IPT Gene Operator

<400> SEQUENCE: 8
tataattaaa atattaactg tcgcatt                                  27

<210> SEQ ID NO 9
<211> LENGTH: 11
<212> TYPE: DNA
<213> ORGANISM: Tobacco
<220> FEATURE:
<223> OTHER INFORMATION: Operator sequence binding to ERF

<400> SEQUENCE: 9
```
taagagccgc c                                                                          11

<210> SEQ ID NO 10
<211> LENGTH: 9
<212> TYPE: DNA
<213> ORGANISM: Potato
<220> FEATURE:
<223> OTHER INFORMATION: Operator sequence binding to SEBF

<400> SEQUENCE: 10 gactgtcac                                                                             9

<210> SEQ ID NO 11
<211> LENGTH: 9
<212> TYPE: DNA
<213> ORGANISM: Anabidopsis Thaliana
<220> FEATURE:
<223> OTHER INFORMATION: Operator sequence binding to CBF

<400> SEQUENCE: 11 taccgacat                                                                             9

<210> SEQ ID NO 12
<211> LENGTH: 8
<212> TYPE: DNA
<213> ORGANISM: Arabidopsis Thaliana
<220> FEATURE:
<223> OTHER INFORMATION: Operator sequence binding to CBF

<400> SEQUENCE: 12 tggccgac                                                                              8

<210> SEQ ID NO 13
<211> LENGTH: 16
<212> TYPE: PRT
<213> ORGANISM: Arabidopsis
<220> FEATURE:
<223> OTHER INFORMATION: NLS of Agamous protein

<400> SEQUENCE: 13

Arg Ile Glu Asn Thr Thr Asn Arg Gln Val Thr Phe Cys Lys Arg Arg
1               5                   10                  15

<210> SEQ ID NO 14
<211> LENGTH: 18
<212> TYPE: PRT
<213> ORGANISM: Tobacco
<220> FEATURE:
<223> OTHER INFORMATION: NLS of TGA-1A protein

<400> SEQUENCE: 14

Arg Arg Leu Ala Gln Asn Arg Glu Ala Ala Arg Lys Ser Arg Leu Arg
1               5                   10                  15

Lys Lys

<210> SEQ ID NO 15
<211> LENGTH: 21
<212> TYPE: PRT
<213> ORGANISM: Tobacco
<220> FEATURE:
<223> OTHER INFORMATION: NLS of TGA-1B Protein

<400> SEQUENCE: 15

Lys Lys Arg Ala Arg Leu Val Arg Asn Arg Glu Ser Ala Gln Leu Ser
1               5                   10                  15

```
Arg Gln Arg Lys Lys
            20

<210> SEQ ID NO 16
<211> LENGTH: 18
<212> TYPE: PRT
<213> ORGANISM: Maize
<220> FEATURE:
<223> OTHER INFORMATION: NLS of O2 NLS B Protein

<400> SEQUENCE: 16

Arg Lys Arg Lys Glu Ser Asn Arg Glu Ser Ala Arg Arg Ser Arg Tyr
1               5                   10                  15

Arg Lys

<210> SEQ ID NO 17
<211> LENGTH: 45
<212> TYPE: PRT
<213> ORGANISM: Potyvirus
<220> FEATURE:
<223> OTHER INFORMATION: NLS of NIa protein
<220> FEATURE:
<221> NAME/KEY: misc_feature
<222> LOCATION: (11)..(42)
<223> OTHER INFORMATION: Xaa is any amino acid

<400> SEQUENCE: 17

Lys Lys Asn Gln Lys His Lys Leu Lys Met Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Lys Arg Lys
        35                  40                  45

<210> SEQ ID NO 18
<211> LENGTH: 16
<212> TYPE: PRT
<213> ORGANISM: Xenopus
<220> FEATURE:
<223> OTHER INFORMATION: NLS nucleoplasmin protein

<400> SEQUENCE: 18

Lys Arg Pro Ala Ala Thr Lys Lys Ala Gly Gln Ala Lys Lys Lys Lys
1               5                   10                  15

<210> SEQ ID NO 19
<211> LENGTH: 17
<212> TYPE: PRT
<213> ORGANISM: Xenopus
<220> FEATURE:
<223> OTHER INFORMATION: NLS of NO38 protein

<400> SEQUENCE: 19

Lys Arg Ile Ala Pro Asp Ser Ala Ser Lys Val Pro Arg Lys Lys Thr
1               5                   10                  15

Arg

<210> SEQ ID NO 20
<211> LENGTH: 17
<212> TYPE: PRT
<213> ORGANISM: Xenopus
<220> FEATURE:
<223> OTHER INFORMATION: NLS of N1/N2 protein

<400> SEQUENCE: 20
```

```
Lys Arg Lys Thr Glu Glu Ser Pro Leu Lys Asp Lys Asp Ala Lys
1               5                   10                  15

Lys

<210> SEQ ID NO 21
<211> LENGTH: 17
<212> TYPE: PRT
<213> ORGANISM: Rat
<220> FEATURE:
<223> OTHER INFORMATION: NLS of Glucocorticoid receptor

<400> SEQUENCE: 21

Arg Lys Cys Leu Gln Ala Gly Met Asn Leu Glu Ala Arg Lys Thr Lys
1               5                   10                  15

Lys

<210> SEQ ID NO 22
<211> LENGTH: 17
<212> TYPE: PRT
<213> ORGANISM: Human
<220> FEATURE:
<223> OTHER INFORMATION: NLS of Glucocorticoid a receptor

<400> SEQUENCE: 22

Arg Lys Cys Leu Gln Ala Gly Met Asn Leu Glu Ala Arg Lys Thr Lys
1               5                   10                  15

Lys

<210> SEQ ID NO 23
<211> LENGTH: 17
<212> TYPE: PRT
<213> ORGANISM: Human
<220> FEATURE:
<223> OTHER INFORMATION: NLS of Glucocorticoid b receptor

<400> SEQUENCE: 23

Arg Lys Cys Leu Gln Ala Gly Met Asn Leu Glu Ala Arg Lys Thr Lys
1               5                   10                  15

Lys

<210> SEQ ID NO 24
<211> LENGTH: 17
<212> TYPE: PRT
<213> ORGANISM: Chicken
<220> FEATURE:
<223> OTHER INFORMATION: NLS of Progesterone receptor

<400> SEQUENCE: 24

Arg Lys Cys Cys Gln Ala Gly Met Val Leu Gly Gly Arg Lys Phe Lys
1               5                   10                  15

Lys

<210> SEQ ID NO 25
<211> LENGTH: 17
<212> TYPE: PRT
<213> ORGANISM: Human
<220> FEATURE:
<223> OTHER INFORMATION: NLS of Androgen receptor

<400> SEQUENCE: 25

Arg Lys Cys Tyr Glu Ala Gly Met Thr Leu Gly Ala Arg Lys Leu Lys
1               5                   10                  15

Lys
```

<210> SEQ ID NO 26
<211> LENGTH: 17
<212> TYPE: PRT
<213> ORGANISM: Chicken
<220> FEATURE:
<223> OTHER INFORMATION: NLS of p53 protein

<400> SEQUENCE: 26

Arg Arg Cys Phe Glu Val Arg Val Cys Ala Cys Pro Gly Arg Asp Arg
1               5                   10                  15

Lys

<210> SEQ ID NO 27
<211> LENGTH: 25
<212> TYPE: DNA
<213> ORGANISM: Agrobacterium Tumefaciens
<220> FEATURE:
<223> OTHER INFORMATION: VirC/VirD operator sequence

<400> SEQUENCE: 27
tatatttcaa ttttattgta atata                                         25

<210> SEQ ID NO 28
<211> LENGTH: 108
<212> TYPE: DNA
<213> ORGANISM: Artificial Sequence
<220> FEATURE:
<223> OTHER INFORMATION: ROS-OPDS

<400> SEQUENCE: 28
atctccactg acgtaaggga tgacgcacaa tcccactatc cttcgcaaga cccttcctct    60
atataatata tttcaatttt attgtaatat aacacggggg actctaga                108

<210> SEQ ID NO 29
<211> LENGTH: 113
<212> TYPE: DNA
<213> ORGANISM: Artificial Sequence
<220> FEATURE:
<223> OTHER INFORMATION: ROS-OPDA

<400> SEQUENCE: 29
gatcctctag agtcccccgt gttatattac aataaaattg aaatatatta tatagaggaa    60
gggtcttgcg aaggatagtg ggattgtgcg tcatccctta cgtcagtgga gat          113

<210> SEQ ID NO 30
<211> LENGTH: 107
<212> TYPE: DNA
<213> ORGANISM: Artificial Sequence
<220> FEATURE:
<223> OTHER INFORMATION: ROS-OPUS

<400> SEQUENCE: 30
atctccactg acgtaaggga tgacgcacaa tctatatttc aattttattg taatatacta    60
tataaggaag ttcatttcat ttggagagaa cacgggggac tctagag                 107

<210> SEQ ID NO 31
<211> LENGTH: 111
<212> TYPE: DNA
<213> ORGANISM: Artificial Sequence
<220> FEATURE:
<223> OTHER INFORMATION: ROS-OPUA

<400> SEQUENCE: 31

```
gatcctctag agtcccccgt gttctctcca aatgaaatga acttccttat atagtatatt      60
acaataaaat tgaaatatag attgtgcgtc atcccttacg tcagtggaga t              111
```

<210> SEQ ID NO 32
<211> LENGTH: 108
<212> TYPE: DNA
<213> ORGANISM: Artificial Sequence
<220> FEATURE:
<223> OTHER INFORMATION: ROS-OPPS

<400> SEQUENCE: 32

```
atctccactg acgtaaggga tgacgcacaa tctatatttc aattttattg taatatacta      60
tataatatat ttcaatttta ttgtaatata acacggggga ctctagag                 108
```

<210> SEQ ID NO 33
<211> LENGTH: 112
<212> TYPE: DNA
<213> ORGANISM: Artificial Sequence
<220> FEATURE:
<223> OTHER INFORMATION: ROS-OPPA

<400> SEQUENCE: 33

```
gatcctctag agtcccccgt gttatattac aataaaattg aaatatatta tatagtatat      60
tacaataaaa ttgaaatata gattgtgcgt catcccttac gtcagtggag at             112
```

<210> SEQ ID NO 34
<211> LENGTH: 59
<212> TYPE: DNA
<213> ORGANISM: Artificial Sequence
<220> FEATURE:
<223> OTHER INFORMATION: ROS-OP1

<400> SEQUENCE: 34

```
gatcctatat ttcaatttta ttgtaatata gctatatttc aattttattg taatataat       59
```

<210> SEQ ID NO 35
<211> LENGTH: 57
<212> TYPE: DNA
<213> ORGANISM: Artificial Sequence
<220> FEATURE:
<223> OTHER INFORMATION: ROS-OP2

<400> SEQUENCE: 35

```
cgattatatt acaataaaat tgaaatatag ctatattaca ataaaattga aatatag          57
```

<210> SEQ ID NO 36
<211> LENGTH: 36
<212> TYPE: DNA
<213> ORGANISM: Artificial Sequence
<220> FEATURE:
<223> OTHER INFORMATION: tms2 promoter sense primer

<400> SEQUENCE: 36

```
tgcggatgca taagcttgct gacattgcta gaaaag                                 36
```

<210> SEQ ID NO 37
<211> LENGTH: 26
<212> TYPE: DNA
<213> ORGANISM: Artificial Sequence
<220> FEATURE:
<223> OTHER INFORMATION: tms2 promoter anti-sense primer

<400> SEQUENCE: 37

```
cggggatcct tcagggcca tttcag                                              26
```

<210> SEQ ID NO 38
<211> LENGTH: 24
<212> TYPE: DNA
<213> ORGANISM: Artificial Sequence
<220> FEATURE:
<223> OTHER INFORMATION: actin2 promoter sense primer

<400> SEQUENCE: 38

```
aagcttatgt atgcaagagt cagc                                               24
```

210> SEQ ID NO 39
<211> LENGTH: 24
<212> TYPE: DNA
<213> ORGANISM: Artificial Sequence
<220> FEATURE:
<223> OTHER INFORMATION: actin2 promoter anti-sense primer

<400> SEQUENCE: 39

```
ttgactagta tcagcctcag ccat                                               24
```

<210> SEQ ID NO 40
<211> LENGTH: 138
<212> TYPE: DNA
<213> ORGANISM: Artificial Sequence
<220> FEATURE:
<223> OTHER INFORMATION: EcoRV to ATG of GUS

<400> SEQUENCE: 40

```
gatatctcca ctgacgtaag ggatgacgca caatcccact atccttcgca agacccttcc        60
tctatataat atatttcaat tttattgtaa tataacacgg gggactctag aggatccccg       120
ggtggtcagt cccttatg                                                    138
```

<210> SEQ ID NO 41
<211> LENGTH: 136
<212> TYPE: DNA
<213> ORGANISM: Artificial Sequence
<220> FEATURE:
<223> OTHER INFORMATION: EcoRV to ATG of GUS

<400> SEQUENCE: 41

```
gatatctcca ctgacgtaag ggatgacgca caatctatat ttcaattttta ttgtaatata       60 ctatataagg aagttcattt catttggaga gaacacgggg gactctagag gatccccggg      120
tggtcagtcc cttatg                                                      136
```

<210> SEQ ID NO 42
<211> LENGTH: 137
<212> TYPE: DNA
<213> ORGANISM: Artificial Sequence
<220> FEATURE:
<223> OTHER INFORMATION: EcoRV to ATG of GUS

<400> SEQUENCE: 42

```
gatatctcca ctgacgtaag ggatgacgca caatctatat ttcaattttta ttgtaatata       60 ctatataata tatttcaatt ttattgtaat ataacacggg ggactctaga ggatccccgg      120
gtggtcagtc ccttatg                                                     137
```

<210> SEQ ID NO 43
<211> LENGTH: 237
<212> TYPE: DNA
<213> ORGANISM: Artificial Sequence
<220> FEATURE:
<223> OTHER INFORMATION: EcoRV to ATG of GUS

<400> SEQUENCE: 43
gatatctcca ctgacgtaag ggatgacgca caatcccact atccttcgca agacccttcc    60
tctatataat atatttcaat tttattgtaa tataaacacgg gggactctag aggatcctat   120
atttcaattt tattgtaata tagctatatt tcaattttat tgtaatataa tcgatttcga   180
acccggggta ccgaattcct cgagtctaga ggatccccgg gtggtcagtc ccttatg      237

<210> SEQ ID NO 44
<211> LENGTH: 31
<212> TYPE: DNA
<213> ORGANISM: Artificial Sequence
<220> FEATURE:
<223> OTHER INFORMATION: forward primer for HDA19 A. thaliana,
    pDBLeu-HDA19

<400> SEQUENCE: 44
gcgtcgacga tggatactgg cggcaattcg c                                   31

<210> SEQ ID NO 45
<211> LENGTH: 32
<212> TYPE: DNA
<213> ORGANISM: Artificial Sequence
<220> FEATURE:
<223> OTHER INFORMATION: reverse primer for HDA19 A. thaliana,
    pDBLeu-HDA19

<400> SEQUENCE: 45
aggcggccgc ttatgtttta ggaggaaacg cc                                  32

<210> SEQ ID NO 46
<211> LENGTH: 31
<212> TYPE: DNA
<213> ORGANISM: Artificial Sequence
<220> FEATURE:
<223> OTHER INFORMATION: forward primer for Gen5 Arabidops
    is, GST-Gen5

<400> SEQUENCE: 46
gcgtcgacga tggactctca ctcttcccac c                                   31

<210> SEQ ID NO 47
<211> LENGTH: 31
<212> TYPE: DNA
<213> ORGANISM: Artificial Sequence
<220> FEATURE:
<223> OTHER INFORMATION: reverse primer for Gen5 Arabidops
    is, GST-Gen5

<400> SEQUENCE: 47
gcgcggccgc ctattgagat ttagcaccag a                                   31

<210> SEQ ID NO 48
<211> LENGTH: 31
<212> TYPE: DNA
<213> ORGANISM: Artificial Sequence
<220> FEATURE:
<223> OTHER INFORMATION: reverse primer forHDA1
    9, GST-HDA19

<400> SEQUENCE: 48
gcgcggccgc ttatgtttta ggaggaaacg c         31

<210> SEQ ID NO 49
<211> LENGTH: 29
<212> TYPE: DNA
<213> ORGANISM: Artificial Sequence
<220> FEATURE:
<223> OTHER INFORMATION: forward primer for bnKCP1, 1-80, 1-160
      (generation of mutants)

<400> SEQUENCE: 49
gcaagcttat ggcaggagga ggaccaact         29

<210> SEQ ID NO 50
<211> LENGTH: 29
<212> TYPE: DNA
<213> ORGANISM: Artificial Sequence
<220> FEATURE:
<223> OTHER INFORMATION: reverse primer for bnKCP1 1-160 (generation
      of mutants)

<400> SEQUENCE: 50
cgctcgagct cctcctcatc attgtcttc         29

<210> SEQ ID NO 51
<211> LENGTH: 29
<212> TYPE: DNA
<213> ORGANISM: Artificial Sequence
<220> FEATURE:
<223> OTHER INFORMATION: reverse primer for bnKCP1 1-80 (generation
      of mutants)

<400> SEQUENCE: 51
cgctcgagat gaacaggcaa aagaggcat         29

<210> SEQ ID NO 52
<211> LENGTH: 29
<212> TYPE: DNA
<213> ORGANISM: Artificial Sequence
<220> FEATURE:
<223> OTHER INFORMATION: reverse primer for bnKCP1 (generation
      of mutants)

<400> SEQUENCE: 52
cgctcgagct catcttcttc ttcttcttc         29

<210> SEQ ID NO 53
<211> LENGTH: 30
<212> TYPE: DNA
<213> ORGANISM: Artificial Sequence
<220> FEATURE:
<223> OTHER INFORMATION: forward primer for bnKCP1, 1-80 and 1-160
      (in vivo assay and transactivation assay)

<400> SEQUENCE: 53
gcgtcgacga tggcaggagg aggaccaact         30

<210> SEQ ID NO 54
<211> LENGTH: 31
<212> TYPE: DNA
<213> ORGANISM: Artificial Sequence
<220> FEATURE:
<223> OTHER INFORMATION: reverse prime
      r for bnKCP1

<400> SEQUENCE: 54

```
gcgcggccgc ctcatcttct tcttcttcct c                              31
```

<210> SEQ ID NO 55
<211> LENGTH: 31
<212> TYPE: DNA
<213> ORGANISM: Artificial Sequence
<220> FEATURE:
<223> OTHER INFORMATION: reverse prime
     r for bnKCP1

<400> SEQUENCE: 55

```
gcgcggccgc atgaacaggc aaaagaggca t                              31
```

<210> SEQ ID NO 56
<211> LENGTH: 31
<212> TYPE: DNA
<213> ORGANISM: Artificial Sequence
<220> FEATURE:
<223> OTHER INFORMATION: reverse prime
     r for bnKCP1

<400> SEQUENCE: 56

```
gcgcggccgc ctcctcctca tcattgtctt c                              31
```

<210> SEQ ID NO 57
<211> LENGTH: 45
<212> TYPE: DNA
<213> ORGANISM: Artificial Sequence
<220> FEATURE:
<223> OTHER INFORMATION: forward primer fo
     r bnKCP1G188

<400> SEQUENCE: 57

```
gatgttcttg cgaggagacc aggattcaag aacagagcat tgaag              45
```

<210> SEQ ID NO 58
<211> LENGTH: 45
<212> TYPE: DNA
<213> ORGANISM: Artificial Sequence
<220> FEATURE:
<223> OTHER INFORMATION: reverse primer fo
     r bnKCP1G188

<400> SEQUENCE: 58

```
cttcaatgct ctgttcttga atcctggtct cctcgcaaga acatc              45
```

<210> SEQ ID NO 59
<211> LENGTH: 30
<212> TYPE: DNA
<213> ORGANISM: Artificial Sequence
<220> FEATURE:
<223> OTHER INFORMATION: forward primer for b
     nKCP1 81-215

<400> SEQUENCE: 59

```
gcgtcgacgc tagggttggc ttcattgaga                                30
```

<210> SEQ ID NO 60
<211> LENGTH: 29
<212> TYPE: DNA
<213> ORGANISM: Artificial Sequence
<220> FEATURE:
<223> OTHER INFORMATION: forward primer for entire encoding regi
     on of bnKCP1

<400> SEQUENCE: 60

```
gcgaattcat ggcaggagga ggaccaact                                 29
```

```
<210> SEQ ID NO 61
<211> LENGTH: 29
<212> TYPE: DNA
<213> ORGANISM: Artificial Sequence
<220> FEATURE:
<223> OTHER INFORMATION: reverse primer for entire coding regi
      on of bnKCP1

<400> SEQUENCE: 61
cggagctcct catcttcttc ttcttcttc                                         29

<210> SEQ ID NO 62
<211> LENGTH: 7
<212> TYPE: PRT
<213> ORGANISM: Brassica Napus
<220> FEATURE:
<223> OTHER INFORMATI
      ON: pat7 NLS

<400> SEQUENCE: 62

Pro Leu Asn Lys Lys Arg Arg
1               5

<210> SEQ ID NO 63
<211> LENGTH: 143
<212> TYPE: PRT
<213> ORGANISM: Rhizobium Elti
<220> FEATURE:
<223> OTHER INFORMATION: ROSR (ROS repressor)

<400> SEQUENCE: 63

Met Thr Asp Met Ala Thr Gly Asn Ala Pro Glu Leu Leu Val Glu Leu
1               5                   10                  15

Thr Ala Asp Ile Val Ala Ala Tyr Val Ser Asn His Val Val Pro Val
            20                  25                  30

Ser Asp Leu Ala Asn Leu Ile Ser Asp Val His Ser Ala Leu Ser Asn
        35                  40                  45

Thr Ser Val Pro Gln Pro Ala Ala Val Val Glu Lys Gln Lys Pro
    50                  55                  60

Ala Val Ser Val Arg Lys Ser Val Gln Asp Glu Gln Ile Thr Cys Leu
65                  70                  75                  80

Glu Cys Gly Gly Asn Phe Lys Ser Leu Lys Arg His Leu Met Thr His
                85                  90                  95

His Ser Leu Ser Pro Glu Glu Tyr Arg Glu Lys Trp Asp Leu Pro Thr
            100                 105                 110

Asp Tyr Pro Met Val Ala Pro Ala Tyr Ala Glu Ala Arg Ser Arg Leu
        115                 120                 125

Ala Lys Glu Met Gly Leu Gly Gln Arg Arg Lys Arg Gly Arg Gly
    130                 135                 140

<210> SEQ ID NO 64
<211> LENGTH: 142
<212> TYPE: PRT
<213> ORGANISM: Agrobacterium Radiobacter
<220> FEATURE:
<223> OTHER INFORMATION: ROSAR (ROS repressor)

<400> SEQUENCE: 64

Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Val Pro Val
```

-continued

```
                 20                  25                  30
Thr Glu Leu Pro Gly Leu Ile Ser Asp Val His Thr Ala Leu Ser Gly
             35                  40                  45

Thr Ser Ala Pro Ala Ser Val Ala Val Asn Val Glu Lys Gln Lys Pro
 50                  55                  60

Ala Val Ser Val Arg Lys Ser Val Gln Asp Asp His Ile Val Cys Leu
 65                  70                  75                  80

Glu Cys Gly Gly Ser Phe Lys Ser Leu Lys Arg His Leu Thr Thr His
                 85                  90                  95

His Ser Met Thr Pro Glu Glu Tyr Arg Glu Lys Trp Asp Leu Gln Val
             100                 105                 110

Asp Tyr Pro Met Val Ala Pro Ala Tyr Ala Glu Ala Arg Ser Arg Leu
         115                 120                 125

Ala Lys Glu Met Gly Leu Gly Gln Arg Arg Lys Ala Asn Arg
     130                 135                 140
```

```
<210> SEQ ID NO 65
<211> LENGTH: 143
<212> TYPE: PRT
<213> ORGANISM: Rhizobium Melilotti
<220> FEATURE:
<223> OTHER INFORMATION: MucR (ROS repressor)

<400> SEQUENCE: 65

Met Thr Glu Thr Ser Leu Gly Thr Ser Asn Glu Leu Leu Val Glu Leu
 1               5                  10                  15

Thr Ala Glu Ile Val Ala Ala Tyr Val Ser Asn His Val Val Pro Val
             20                  25                  30

Ala Glu Leu Pro Thr Leu Ile Ala Asp Val His Ser Ala Leu Asn Asn
             35                  40                  45

Thr Thr Ala Pro Ala Pro Val Val Pro Val Glu Lys Pro Lys Pro
 50                  55                  60

Ala Val Ser Val Arg Lys Ser Val Gln Asp Asp Gln Ile Thr Cys Leu
 65                  70                  75                  80

Glu Cys Gly Gly Thr Phe Lys Ser Leu Lys Arg His Leu Met Thr His
                 85                  90                  95

His Asn Leu Ser Pro Glu Glu Tyr Arg Asp Lys Trp Asp Leu Pro Ala
             100                 105                 110

Asp Tyr Pro Met Val Ala Pro Ala Tyr Ala Glu Ala Arg Ser Arg Leu
         115                 120                 125

Ala Lys Glu Met Gly Leu Gly Gln Arg Arg Lys Arg Arg Gly Lys
     130                 135                 140
```

```
<210> SEQ ID NO 66
<211> LENGTH: 10
<212> TYPE: DNA
<213> ORGANISM: Agrobacterium Tumefaciens
<220> FEATURE:
<223> OTHER INFORMATION: VirC/VirD DNA binding site seq (1)

<400> SEQUENCE: 66
tatatttcaa                                                        10
```

```
<210> SEQ ID NO 67
<211> LENGTH: 10
<212> TYPE: DNA
<213> ORGANISM: Agrobacterium Tumefaciens
<220> FEATURE:
<223> OTHER INFORMATION: Virc/VirD DNA binding site seq (2)
```

```
<400> SEQUENCE: 67
tatattacaa                                                              10

<210> SEQ ID NO 68
<211> LENGTH: 10
<212> TYPE: DNA
<213> ORGANISM: Agrobacterium Tumefaciens
<220> FEATURE:
<223> OTHER INFORMATION: ipt DNA binding site seq (1)

<400> SEQUENCE: 68
tataattaaa                                                              10

<210> SEQ ID NO 69
<211> LENGTH: 10
<212> TYPE: DNA
<213> ORGANISM: Agrobacterium Tumefaciens
<220> FEATURE:
<223> OTHER INFORMATION: ipt DNA binding site seq (2)

<400> SEQUENCE: 69
aatgcgacag                                                              10

<210> SEQ ID NO 70
<211> LENGTH: 10
<212> TYPE: DNA
<213> ORGANISM: Artificial Sequence
<220> FEATURE:
<223> OTHER INFORMATION: concensus DNA binding site seq

<400> SEQUENCE: 70 tatahttcaa                                                              10

<210> SEQ ID NO 71
<211> LENGTH: 215
<212> TYPE: PRT
<213> ORGANISM: Brassica Napus
<220> FEATURE:
<223> OTHER INFORMATION: bnKCP

<400> SEQUENCE: 71

Met Ala Gly Gly Gly Pro Thr Phe Ser Ile Glu Leu Ser Ala Tyr Gly
1               5                   10                  15

Ser Asp Leu Pro Thr Asp Lys Ala Ser Gly Asp Ile Pro Asn Glu Glu
            20                  25                  30

Gly Ser Gly Leu Ser Arg Val Gly Ser Gly Ile Trp Ser Gly Arg Thr
        35                  40                  45

Val Asp Tyr Ser Ser Glu Ser Ser Ser Ile Gly Thr Pro Gly Asp
    50                  55                  60

Ser Glu Glu Glu Asp Glu Glu Ser Glu Glu Asp Asn Asp Glu Glu
65                  70                  75                  80

Leu Gly Leu Ala Ser Leu Arg Ser Leu Glu Asp Ser Leu Pro Ser Lys
            85                  90                  95

Gly Leu Ser Ser His Tyr Lys Gly Lys Ser Lys Ser Phe Gly Asn Leu
            100                 105                 110

Gly Glu Ile Gly Ser Val Lys Glu Val Pro Lys Gln Glu Asn Pro Leu
        115                 120                 125

Asn Lys Lys Arg Arg Leu Gln Ile Tyr Asn Lys Leu Ala Arg Lys Ser
    130                 135                 140

Phe Tyr Ser Trp Gln Asn Pro Lys Ser Met Pro Leu Leu Pro Val His
```

```
                145                 150                 155                 160
Glu Asp Asn Asp Asp Glu Glu Gly Asp Asp Gly Asp Leu Ser Asp Glu
                    165                 170                 175

Glu Arg Gly Gly Asp Val Leu Ala Arg Arg Pro Ser Phe Lys Asn Arg
                180                 185                 190

Ala Leu Lys Ser Met Ser Cys Phe Ala Leu Ser Asp Leu Gln Glu Glu
            195                 200                 205

Glu Glu Glu Glu Glu Asp Glu
        210                 215

<210> SEQ ID NO 72
<211> LENGTH: 240
<212> TYPE: PRT
<213> ORGANISM: Arabidopsis
<220> FEATURE:
<223> OTHER INFORMATION: atKCP

<400> SEQUENCE: 72

Met Glu Leu Met Ala Lys Pro Thr Phe Ser Ile Glu Val Ser Gln Tyr
1               5                   10                  15

Gly Thr Thr Asp Leu Pro Ala Thr Glu Lys Ala Ser Ser Ser Ser Ser
                20                  25                  30

Ser Phe Glu Thr Thr Asn Glu Glu Gly Val Glu Glu Ser Gly Leu Ser
            35                  40                  45

Arg Ile Trp Ser Gly Gln Thr Ala Asp Tyr Ser Ser Asp Ser Ser Ser
        50                  55                  60

Ile Gly Thr Pro Gly Asp Ser Glu Glu Asp Glu Glu Ser Glu Asn
65                  70                  75                  80

Glu Asn Asp Asp Val Ser Ser Lys Glu Leu Gly Leu Arg Gly Leu Ala
                85                  90                  95

Ser Met Ser Ser Leu Glu Asp Ser Leu Pro Ser Lys Arg Gly Leu Ser
            100                 105                 110

Asn His Tyr Lys Gly Lys Ser Lys Ser Phe Gly Asn Leu Gly Glu Ile
        115                 120                 125

Gly Ser Val Lys Glu Val Ala Lys Gln Glu Asn Pro Leu Asn Lys Arg
    130                 135                 140

Arg Arg Leu Gln Ile Cys Asn Lys Leu Ala Arg Lys Ser Phe Tyr Ser
145                 150                 155                 160

Trp Gln Asn Pro Lys Ser Met Pro Leu Leu Pro Val Asn Glu Asp Glu
                165                 170                 175

Asp Asp Asp Asp Glu Asp Asp Glu Glu Asp Leu Lys Ser Gly Phe
                180                 185                 190

Asp Glu Asn Lys Ser Ser Asp Glu Glu Gly Val Lys Lys Val Val
            195                 200                 205

Val Arg Lys Gly Ser Phe Lys Asn Arg Ala Tyr Lys Ser Arg Ser Cys
    210                 215                 220

Phe Ala Leu Ser Asp Leu Ile Glu Glu Glu Asp Asp Asp Asp Gln
225                 230                 235                 240

<210> SEQ ID NO 73
<211> LENGTH: 214
<212> TYPE: PRT
<213> ORGANISM: Arabidopsis
<220> FEATURE:
<223> OTHER INFORMATION: atKCL1

<400> SEQUENCE: 73
```

```
Met Glu Val Leu Val Gly Ser Thr Phe Arg Asp Arg Ser Ser Val Thr
1               5                   10                  15

Thr His Asp Gln Ala Val Pro Ala Ser Leu Ser Ser Arg Ile Gly Leu
            20                  25                  30

Arg Arg Cys Gly Arg Ser Pro Pro Glu Ser Ser Ser Val Gly
        35                  40                  45

Glu Thr Ser Glu Asn Glu Glu Asp Glu Asp Asp Ala Val Ser Ser Ser
    50                  55                  60

Gln Gly Arg Trp Leu Asn Ser Phe Ser Ser Leu Glu Asp Ser Leu
65                  70                  75                  80

Pro Ile Lys Arg Gly Leu Ser Asn His Tyr Ile Gly Lys Ser Lys Ser
            85                  90                  95

Phe Gly Asn Leu Met Glu Ala Ser Asn Thr Asn Asp Leu Val Lys Val
                100                 105                 110

Glu Ser Pro Leu Asn Lys Arg Arg Leu Leu Ile Ala Asn Lys Leu
        115                 120                 125

Arg Arg Arg Ser Ser Leu Ser Ser Phe Ser Ile Tyr Thr Lys Ile Asn
        130                 135                 140

Pro Asn Ser Met Pro Leu Leu Ala Leu Gln Ser Asp Asn Glu Asp
145                 150                 155                 160

His Lys Leu Asn Asp Asp Asp Asp Asp Ser Ser Ser Asp Asp
                165                 170                 175

Glu Thr Ser Lys Leu Lys Glu Lys Arg Met Lys Met Thr Asn His Arg
            180                 185                 190

Asp Phe Met Val Pro Gln Thr Lys Ser Cys Phe Ser Leu Thr Ser Phe
        195                 200                 205

Gln Asp Asp Asp Asp Arg
    210

<210> SEQ ID NO 74
<211> LENGTH: 221
<212> TYPE: PRT
<213> ORGANISM: Arabidopsis
<220> FEATURE:
<223> OTHER INFORMATION: atKCL2

<400> SEQUENCE: 74

Met Val Gly Ser Ser Phe Gly Ile Gly Met Ala Ala Tyr Val Arg Asp
1               5                   10                  15

His Arg Gly Val Ser Ala Gln Asp Lys Ala Val Gln Thr Ala Leu Phe
            20                  25                  30

Leu Ala Asp Glu Ser Gly Arg Gly Gly Ser Gln Ile Gly Ile Gly Leu
        35                  40                  45

Arg Met Ser Asn Asn Asn Lys Ser Pro Glu Glu Ser Ser Asp Ser
    50                  55                  60

Ser Ser Ser Ile Gly Glu Ser Glu Asn Glu Glu Glu Glu
65                  70                  75                  80

Asp Asp Ala Val Ser Cys Gln Arg Gly Thr Leu Asp Ser Phe Ser Ser
            85                  90                  95

Ser Leu Glu Asp Ser Leu Pro Ile Lys Arg Gly Leu Ser Asn His Tyr
                100                 105                 110

Val Gly Lys Ser Lys Ser Phe Gly Asn Leu Met Glu Ala Ser Lys
        115                 120                 125

Ala Lys Asp Leu Glu Lys Val Glu Asn Pro Phe Asn Lys Arg Arg Arg
        130                 135                 140
```

Leu Val Ile Ala Asn Lys Leu Arg Arg Gly Arg Ser Ile Thr Tyr
145                 150                 155                 160

Glu Glu Asp His His Ile His Asn Asp Asp Tyr Glu Asp Asp Gly
                165                 170                 175

Asp Gly Asp His Arg Lys Ile Met Met Met Lys Asn Lys Lys
        180                 185                 190

Glu Leu Met Ala Gln Thr Arg Ser Cys Phe Cys Leu Ser Ser Leu Gln
        195                 200                 205

Glu Glu Asp Asp Gly Asp Gly Asp Asp Glu Asp Glu
    210                 215                 220

<210> SEQ ID NO 75
<211> LENGTH: 42
<212> TYPE: PRT
<213> ORGANISM: Brassica Napus
<220> FEATURE:
<223> OTHER INFORMATION: bnKCP Fragment

<400> SEQUENCE: 75

Gly Asp Asp Gly Asp Leu Ser Asp Glu Glu Arg Gly Gly Asp Val Leu
1               5                   10                  15

Ala Arg Arg Pro Ser Phe Lys Asn Arg Ala Leu Lys Ser Met Ser Cys
                20                  25                  30

Phe Ala Leu Ser Asp Leu Gln Glu Glu
            35                  40

<210> SEQ ID NO 76
<211> LENGTH: 42
<212> TYPE: PRT
<213> ORGANISM: Human
<220> FEATURE:
<223> OTHER INFORMATION: ATF-1

<400> SEQUENCE: 76

Asp Ser Ser Asp Ser Ile Gly Ser Ser Gln Gln Ala His Gly Ile Leu
1               5                   10                  15

Ala Arg Arg Pro Ser Tyr Arg Lys Ile Leu Lys Asp Leu Ser Ser Glu
                20                  25                  30

Asp Thr Arg Gly Arg Lys Gly Asp Gly Glu
            35                  40

<210> SEQ ID NO 77
<211> LENGTH: 42
<212> TYPE: PRT
<213> ORGANISM: Human
<220> FEATURE:
<223> OTHER INFORMATION: hyCREB

<400> SEQUENCE: 77

Glu Ser Val Asp Ser Val Thr Asp Ser Gln Lys Arg Arg Glu Ile Leu
1               5                   10                  15

Ser Arg Arg Pro Ser Tyr Arg Lys Ile Leu Asn Asp Leu Ser Ser Asp
                20                  25                  30

Ala Pro Gly Val Pro Arg Ile Glu Glu Glu
            35                  40

<210> SEQ ID NO 78
<211> LENGTH: 42
<212> TYPE: PRT
<213> ORGANISM: Human
<220> FEATURE:
<223> OTHER INFORMATION: CREB

```
<400> SEQUENCE: 78

Glu Ser Val Asp Ser Val Thr Asp Ser Gln Lys Arg Arg Glu Ile Leu
1               5                   10                  15

Ser Arg Arg Pro Ser Tyr Arg Lys Ile Leu Asn Asp Leu Ser Ser Asp
            20                  25                  30

Ala Pro Gly Val Pro Arg Ile Glu Glu Glu
        35                  40

<210> SEQ ID NO 79
<211> LENGTH: 42
<212> TYPE: PRT
<213> ORGANISM: Mouse
<220> FEATURE:
<223> OTHER INFORMATION: CREM

<400> SEQUENCE: 79

Ser Ala Asp Ser Glu Val Ile Asp Ser His Lys Arg Arg Glu Ile Leu
1               5                   10                  15

Ser Arg Arg Pro Ser Tyr Arg Lys Ile Leu Asn Glu Leu Ser Ser Asp
            20                  25                  30

Val Pro Gly Ile Pro Lys Ile Glu Glu Glu
        35                  40

<210> SEQ ID NO 80
<211> LENGTH: 42
<212> TYPE: PRT
<213> ORGANISM: Human
<220> FEATURE:
<223> OTHER INFORMATION: cCREM

<400> SEQUENCE: 80

Ala Glu Ser Glu Gly Val Ile Asp Ser His Lys Arg Arg Glu Ile Leu
1               5                   10                  15

Ser Arg Arg Pro Ser Tyr Arg Lys Ile Leu Asn Glu Leu Ser Ser Asp
            20                  25                  30

Val Pro Gly Val Pro Lys Ile Glu Glu Glu
        35                  40

<210> SEQ ID NO 81
<211> LENGTH: 461
<212> TYPE: PRT
<213> ORGANISM: Brassica Napus
<220> FEATURE:
<223> OTHER INFORMATION: BNSCL1

<400> SEQUENCE: 81

Met Lys Leu Gln Ala Ser Ser Pro Gln Asp Asn Gln Pro Ser Asn Thr
1               5                   10                  15

Thr Asn Asn Ser Thr Asp Ser Asn His Leu Ser Met Asp Glu His Ala
            20                  25                  30

Met Arg Ser Met Asp Trp Asp Ser Ile Met Lys Glu Leu Glu Val Asp
        35                  40                  45

Asp Asp Ser Ala Pro Tyr Gln Leu Gln Pro Ser Ser Phe Asn Leu Pro
    50                  55                  60

Val Phe Pro Asp Ile Asp Ser Asp Val Tyr Pro Gly Pro Asn Gln
65                  70                  75                  80

Ile Thr Gly Tyr Gly Phe Asn Ser Leu Asp Ser Val Asp Asn Gly Gly
                85                  90                  95

Phe Asp Tyr Ile Glu Asp Leu Ile Arg Val Val Asp Cys Ile Glu Ser
```

-continued

```
                100                 105                 110
Asp Glu Leu His Leu Ala His Val Val Leu Ser Gln Leu Asn Gln Arg
            115                 120                 125
Leu Gln Thr Ser Ala Gly Arg Pro Leu Gln Arg Ala Ala Phe Tyr Phe
        130                 135                 140
Lys Glu Ala Leu Gly Ser Leu Leu Thr Gly Thr Asn Arg Asn Gln Leu
145                 150                 155                 160
Phe Ser Trp Ser Asp Ile Val Gln Lys Ile Arg Ala Ile Lys Glu Phe
                165                 170                 175
Ser Gly Ile Ser Pro Ile Pro Leu Phe Ser His Phe Thr Ala Asn Gln
            180                 185                 190
Ala Ile Leu Asp Ser Leu Ser Ser Gln Ser Ser Ser Pro Phe Val His
        195                 200                 205
Val Val Asp Phe Glu Ile Gly Phe Gly Gly Gln Tyr Ala Ser Leu Met
210                 215                 220
Arg Glu Ile Ala Glu Lys Ser Ala Asn Gly Gly Phe Leu Arg Val Thr
225                 230                 235                 240
Ala Val Val Ala Glu Asp Cys Ala Val Glu Thr Arg Leu Val Lys Glu
                245                 250                 255
Asn Leu Thr Gln Phe Ala Ala Glu Met Lys Ile Arg Phe Gln Ile Glu
            260                 265                 270
Phe Val Leu Met Lys Thr Phe Glu Ile Leu Ser Phe Lys Ala Ile Arg
        275                 280                 285
Phe Val Asp Gly Glu Arg Thr Val Val Leu Ile Ser Pro Ala Ile Phe
    290                 295                 300
Arg Arg Val Ile Gly Ile Ala Glu Phe Val Asn Asn Leu Gly Arg Val
305                 310                 315                 320
Ser Pro Asn Val Val Phe Val Asp Ser Glu Gly Cys Thr Glu Thr
                325                 330                 335
Ala Gly Ser Gly Ser Phe Arg Arg Glu Phe Val Ser Ala Phe Glu Phe
            340                 345                 350
Tyr Thr Met Val Leu Glu Ser Leu Asp Ala Ala Ala Pro Pro Gly Asp
        355                 360                 365
Leu Val Lys Lys Ile Val Glu Thr Phe Leu Leu Arg Pro Lys Ile Ser
    370                 375                 380
Ala Ala Val Glu Thr Ala Ala Asn Arg Arg Ser Ala Gly Gln Met Thr
385                 390                 395                 400
Trp Arg Glu Met Leu Cys Ala Ala Gly Met Arg Pro Val Gln Leu Ser
                405                 410                 415
Gln Phe Ala Asp Phe Gln Ala Glu Cys Leu Leu Glu Lys Ala Gln Val
            420                 425                 430
Arg Gly Phe His Val Ala Lys Arg Gln Gly Glu Leu Val Leu Cys Trp
        435                 440                 445
His Gly Arg Ala Leu Val Ala Thr Ser Ala Trp Arg Phe
    450                 455                 460
```

<210> SEQ ID NO 82
<211> LENGTH: 486
<212> TYPE: PRT
<213> ORGANISM: Arabidopsis
<220> FEATURE:
<223> OTHER INFORMATION: atSCL15

<400> SEQUENCE: 82

Met Lys Ile Pro Ala Ser Ser Pro Gln Asp Thr Thr Asn Asn Asn Asn

-continued

```
1               5                   10                  15
Asn Thr Asn Ser Thr Asp Ser Asn His Leu Ser Met Asp Glu His Val
                20                  25                  30
Met Arg Ser Met Asp Trp Asp Ser Ile Met Lys Glu Leu Glu Leu Asp
                35                  40                  45
Asp Asp Ser Ala Pro Asn Ser Leu Lys Thr Gly Phe Thr Thr Thr Thr
                50                  55                  60
Thr Asp Ser Thr Ile Leu Pro Leu Tyr Ala Val Asp Ser Asn Leu Pro
65                      70                  75                  80
Gly Phe Pro Asp Gln Ile Gln Pro Ser Asp Phe Glu Ser Ser Ser Asp
                85                  90                  95
Val Tyr Pro Gly Gln Asn Gln Thr Thr Gly Tyr Gly Phe Asn Ser Leu
                100                 105                 110
Asp Ser Val Asp Asn Gly Gly Phe Asp Phe Ile Glu Asp Leu Ile Arg
                115                 120                 125
Val Val Asp Cys Val Glu Ser Asp Glu Leu Gln Leu Ala Gln Val Val
                130                 135                 140
Leu Ser Arg Leu Asn Gln Arg Leu Arg Ser Pro Ala Gly Arg Pro Leu
145                     150                 155                 160
Gln Arg Ala Ala Phe Tyr Phe Lys Glu Ala Leu Gly Ser Phe Leu Thr
                165                 170                 175
Gly Ser Asn Arg Asn Pro Ile Arg Leu Ser Ser Trp Ser Glu Ile Val
                180                 185                 190
Gln Arg Ile Arg Ala Ile Lys Glu Tyr Ser Gly Ile Ser Pro Ile Pro
                195                 200                 205
Leu Phe Ser His Phe Thr Ala Asn Gln Ala Ile Leu Asp Ser Leu Ser
                210                 215                 220
Ser Gln Ser Ser Ser Pro Phe Val His Val Val Asp Phe Glu Ile Gly
225                     230                 235                 240
Phe Gly Gly Gln Tyr Ala Ser Leu Met Arg Glu Ile Thr Glu Lys Ser
                245                 250                 255
Val Ser Gly Gly Phe Leu Arg Val Thr Ala Val Ala Glu Glu Cys
                260                 265                 270
Ala Val Glu Thr Arg Leu Val Lys Glu Asn Leu Thr Gln Phe Ala Ala
                275                 280                 285
Glu Met Lys Ile Arg Phe Gln Ile Glu Phe Val Leu Met Lys Thr Phe
                290                 295                 300
Glu Met Leu Ser Phe Lys Ala Ile Arg Phe Val Glu Gly Glu Arg Thr
305                     310                 315                 320
Val Val Leu Ile Ser Pro Ala Ile Phe Arg Arg Leu Ser Gly Ile Thr
                325                 330                 335
Asp Phe Val Asn Asn Leu Arg Arg Val Ser Pro Lys Val Val Val Phe
                340                 345                 350
Val Asp Ser Glu Gly Trp Thr Glu Ile Ala Gly Ser Gly Ser Phe Arg
                355                 360                 365
Arg Glu Phe Val Ser Ala Leu Glu Phe Tyr Thr Met Val Leu Glu Ser
                370                 375                 380
Leu Asp Ala Ala Ala Pro Pro Gly Asp Leu Val Lys Lys Ile Val Glu
385                     390                 395                 400
Ala Phe Val Leu Arg Pro Lys Ile Ser Ala Ala Val Glu Thr Ala Ala
                405                 410                 415
Asp Arg Arg His Thr Gly Glu Met Thr Trp Arg Glu Ala Phe Cys Ala
                420                 425                 430
```

```
Ala Gly Met Arg Pro Ile Gln Gln Ser Gln Phe Ala Asp Phe Gln Ala
            435                 440                 445

Glu Cys Leu Leu Glu Lys Ala Gln Val Arg Gly Phe His Val Ala Lys
        450                 455                 460

Arg Gln Gly Glu Leu Val Leu Cys Trp His Gly Arg Ala Leu Val Ala
465                 470                 475                 480

Thr Ser Ala Trp Arg Phe
                485

<210> SEQ ID NO 83
<211> LENGTH: 536
<212> TYPE: PRT
<213> ORGANISM: Lycopersicon Esculentum
<220> FEATURE:
<223> OTHER INFORMATION: lsSCR

<400> SEQUENCE: 83

Met Lys Val Pro Phe Ser Thr Asn Asp Asn Val Ser Lys Pro Leu
1               5                   10                  15

Val Asn Ser Asn Asn Ser Phe Thr Phe Pro Ala Ala Thr Asn Gly Ser
            20                  25                  30

Asn Leu Cys Tyr Glu Pro Lys Ser Val Leu Glu Leu Arg Arg Ser Pro
        35                  40                  45

Ser Pro Ile Val Asp Lys Gln Ile Ile Thr Thr Asn Pro Asp Leu Ser
50                  55                  60

Ala Leu Cys Gly Gly Glu Asp Pro Leu Gln Leu Gly Asp His Val Leu
65                  70                  75                  80

Ser Asn Phe Glu Asp Trp Asp Ser Leu Met Arg Glu Leu Gly Leu His
            85                  90                  95

Asp Asp Ser Ala Ser Leu Ser Lys Thr Asn Pro Leu Thr His Ser Glu
        100                 105                 110

Ser Leu Thr Gln Phe His Asn Leu Ser Glu Phe Ser Ala Glu Ser Asn
    115                 120                 125

Gln Phe Pro Ser Pro Asp Phe Ser Phe Ser Asp Thr Asn Phe Pro Gln
130                 135                 140

Gln Phe Pro Thr Val Asn Gln Ala Ser Phe Ile Asn Ala Leu Asp Leu
145                 150                 155                 160

Ser Gly Asp Ile His Gln Asn Trp Ser Val Gly Phe Asp Tyr Val Asp
                165                 170                 175

Glu Leu Ile Arg Phe Ala Glu Cys Phe Glu Thr Asn Ala Phe Gln Leu
            180                 185                 190

Ala His Val Ile Leu Ala Arg Leu Asn Gln Arg Leu Arg Ser Ala Ala
        195                 200                 205

Gly Lys Pro Leu Gln Arg Ala Ala Phe Tyr Phe Lys Glu Ala Leu Gln
    210                 215                 220

Ala Gln Leu Ala Gly Ser Ala Arg Gln Thr Arg Ser Ser Ser Ser Ser
225                 230                 235                 240

Asp Val Ile Gln Thr Ile Lys Ser Tyr Lys Ile Leu Ser Asn Ile Ser
                245                 250                 255

Pro Ile Pro Met Phe Ser Ser Phe Thr Ala Asn Gln Ala Val Leu Glu
            260                 265                 270

Ala Val Asp Gly Ser Met Leu Val His Val Ile Asp Phe Asp Ile Gly
        275                 280                 285

Leu Gly Gly His Trp Ala Ser Phe Met Lys Glu Leu Ala Asp Lys Ala
    290                 295                 300
```

Glu Cys Arg Lys Ala Asn Ala Pro Ile Leu Arg Ile Thr Ala Leu Val
305                 310                 315                 320

Pro Glu Glu Tyr Ala Val Glu Ser Arg Leu Ile Arg Glu Asn Leu Thr
            325                 330                 335

Gln Phe Ala Arg Glu Leu Asn Ile Gly Phe Glu Ile Asp Phe Val Leu
            340                 345                 350

Ile Arg Thr Phe Glu Leu Leu Ser Phe Lys Ala Ile Lys Phe Met Glu
            355                 360                 365

Gly Glu Lys Thr Ala Val Leu Leu Ser Pro Ala Ile Phe Arg Arg Val
370                 375                 380

Gly Ser Gly Phe Val Asn Glu Leu Arg Arg Ile Ser Pro Asn Val Val
385                 390                 395                 400

Val His Val Asp Ser Glu Gly Leu Met Gly Tyr Gly Ala Met Ser Phe
            405                 410                 415

Arg Gln Thr Val Ile Asp Gly Leu Glu Phe Tyr Ser Thr Leu Leu Glu
            420                 425                 430

Ser Leu Glu Ala Ala Asn Ile Gly Gly Gly Asn Cys Gly Asp Trp Met
            435                 440                 445

Arg Lys Ile Glu Asn Phe Val Leu Phe Pro Lys Ile Val Asp Met Ile
450                 455                 460

Gly Ala Val Gly Arg Arg Gly Gly Gly Ser Trp Arg Asp Ala Met
465                 470                 475                 480

Val Asp Ala Gly Phe Arg Pro Val Gly Leu Ser Gln Phe Ala Asp Phe
            485                 490                 495

Gln Ala Asp Cys Leu Leu Gly Arg Val Gln Val Arg Gly Phe His Val
            500                 505                 510

Ala Lys Arg Gln Ala Glu Met Leu Leu Cys Trp His Asp Arg Ala Leu
            515                 520                 525

Val Ala Thr Ser Ala Trp Arg Cys
            530                 535

<210> SEQ ID NO 84
<211> LENGTH: 26
<212> TYPE: DNA
<213> ORGANISM: Artificial Sequence
<220> FEATURE:
<223> OTHER INFORMATION: BnSCL1 sense primer

<400> SEQUENCE: 84
gatggacgaa catgccatgc gttcca                                        26

<210> SEQ ID NO 85
<211> LENGTH: 21
<212> TYPE: DNA
<213> ORGANISM: Artificial Sequence
<220> FEATURE:
<223> OTHER INFORMATION: BnSCL1 anti-sense primer

<400> SEQUENCE: 85
cgctcggatc ttctgaacaa t                                             21

<210> SEQ ID NO 86
<211> LENGTH: 21
<212> TYPE: DNA
<213> ORGANISM: Artificial Sequence
<220> FEATURE:
<223> OTHER INFORMATION: BnIAA1 sense primer

<400> SEQUENCE: 86
ccacgcgtcc ggtacgatga t                                              21

<210> SEQ ID NO 87
<211> LENGTH: 22
<212> TYPE: DNA
<213> ORGANISM: Artificial Sequence
<220> FEATURE:
<223> OTHER INFORMATION: BnIAA1 anti-sense primer

<400> SEQUENCE: 87
gaagttgaga aatggtttat ga                                             22

<210> SEQ ID NO 88
<211> LENGTH: 21
<212> TYPE: DNA
<213> ORGANISM: Artificial Sequence
<220> FEATURE:
<223> OTHER INFORMATION: BnIAA12 sense primer

<400> SEQUENCE: 88
acgctggtgc ttctcctcct c                                              21

<210> SEQ ID NO 89
<211> LENGTH: 24
<212> TYPE: DNA
<213> ORGANISM: Artificial Sequence
<220> FEATURE:
<223> OTHER INFORMATION: BNIAA12 anti-sense primer

<400> SEQUENCE: 89
aaaacccatt agaagaacca agaa                                           24

<210> SEQ ID NO 90
<211> LENGTH: 33
<212> TYPE: DNA
<213> ORGANISM: Artificial Sequence
<220> FEATURE:
<223> OTHER INFORMATION: forward primer for BnSCL1, BnSCL1 1-358,
      BnSCL1 1-261, BnSCL1 1-217 and BnSCL1 1-145 for pET-28b vector

<400> SEQUENCE: 90
gcaagcttat ggacgaacat gccatgcgtt cca                                 33

<210> SEQ ID NO 91
<211> LENGTH: 29
<212> TYPE: DNA
<213> ORGANISM: Artificial Sequence
<220> FEATURE:
<223> OTHER INFORMATION: reverse primer for BnSCL1 for pET-28b vector

<400> SEQUENCE: 91
cgctcgagaa agcgccacgc tgacgtggc                                      29

<210> SEQ ID NO 92
<211> LENGTH: 29
<212> TYPE: DNA
<213> ORGANISM: Artificial Sequence
<220> FEATURE:
<223> OTHER INFORMATION: reverse primer for BnSCL1 1-358 for pET-28b
      vector

<400> SEQUENCE: 92
cgctcgagcg cggagatctt cggacgtaa                                      29

<210> SEQ ID NO 93

<210> SEQ ID NO 93
<211> LENGTH: 29
<212> TYPE: DNA
<213> ORGANISM: Artificial Sequence
<220> FEATURE:
<223> OTHER INFORMATION: reverse primer for BnSCL1 1-261 for pET-28b vector

<400> SEQUENCE: 93
cgctcgagcc taatcgcctt gaaagataa        29

<210> SEQ ID NO 94
<211> LENGTH: 29
<212> TYPE: DNA
<213> ORGANISM: Artificial Sequence
<220> FEATURE:
<223> OTHER INFORMATION: reverse primer for BnSCL1 1-217 for pET-28b vector

<400> SEQUENCE: 94
cgctcgagcg ccacaaccgc cgtgactct        29

<210> SEQ ID NO 95
<211> LENGTH: 29
<212> TYPE: DNA
<213> ORGANISM: Artificial Sequence
<220> FEATURE:
<223> OTHER INFORMATION: reverse primer for BnSCL1 1-145 for pET-28b vector

<400> SEQUENCE: 95
cgctcgagcg ctcggatctt ctgaacaat        29

<210> SEQ ID NO 96
<211> LENGTH: 34
<212> TYPE: DNA
<213> ORGANISM: Artificial Sequence
<220> FEATURE:
<223> OTHER INFORMATION: forward primer for BnSCL1, BnSCL1 1-358, BnSCL1 1-261, BnSCL1 1-217 and BnSCL1 1-145 for PC86 vector

<400> SEQUENCE: 96
gcgtcgacga tggacgaaca tgccatgcgt tcca        34

<210> SEQ ID NO 97
<211> LENGTH: 30
<212> TYPE: DNA
<213> ORGANISM: Artificial Sequence
<220> FEATURE:
<223> OTHER INFORMATION: forward primer for BnSCL1 146-358 for PC86 vector

<400> SEQUENCE: 97
gcgtcgacga ttaaggagtt ttccggtata        30

<210> SEQ ID NO 98
<211> LENGTH: 30
<212> TYPE: DNA
<213> ORGANISM: Artificial Sequence
<220> FEATURE:
<223> OTHER INFORMATION: forward primer for BnSCL1 218-434 for PC86 vector

<400> SEQUENCE: 98
gcgtcgacgg aggattgcgc cgtcgagacg        30

<210> SEQ ID NO 99
<211> LENGTH: 31

```
<212> TYPE: DNA
<213> ORGANISM: Artificial Sequence
<220> FEATURE:
<223> OTHER INFORMATION: reverse primer for BnSCL1 and BnSCL1 218-434
      for PC86 vector

<400> SEQUENCE: 99
gcgcggccgc aaagcgccac gctgacgtgg c                               31

<210> SEQ ID NO 100
<211> LENGTH: 31
<212> TYPE: DNA
<213> ORGANISM: Artificial Sequence
<220> FEATURE:
<223> OTHER INFORMATION: reverse primer for BnSCL1 1-358 for PC86 vector

<400> SEQUENCE: 100
gcgcggccgc cgcggagatc ttcggacgta a                               31

<210> SEQ ID NO 101
<211> LENGTH: 31
<212> TYPE: DNA
<213> ORGANISM: Artificial Sequence
<220> FEATURE:
<223> OTHER INFORMATION: reverse primer for BnSCL1 1-261 for PC86 vector

<400> SEQUENCE: 101
gcgcggccgc cctaatcgcc ttgaaagata a                               31

<210> SEQ ID NO 102
<211> LENGTH: 31
<212> TYPE: DNA
<213> ORGANISM: Artificial Sequence
<220> FEATURE:
<223> OTHER INFORMATION: reverse primer for BnSCL1 1-217 for PC86 vector

<400> SEQUENCE: 102
gcgcggccgc cgccacaacc gccgtgactc t                               31

<210> SEQ ID NO 103
<211> LENGTH: 31
<212> TYPE: DNA
<213> ORGANISM: Artificial Sequence
<220> FEATURE:
<223> OTHER INFORMATION: reverse primer of BnSCL1 1-145 for PC86 vector

<400> SEQUENCE: 103
gcgcggccgc cgctcggatc ttctgaacaa t                               31

<210> SEQ ID NO 104
<211> LENGTH: 5
<212> TYPE: PRT
<213> ORGANISM: Brassica Napus
<220> FEATURE:
<223> OTHER INFORMATION: LXXLL motif (148LGSLL152)

<400> SEQUENCE: 104

Leu Gly Ser Leu Leu
1               5
```